United States Patent
McGuigan et al.

(10) Patent No.: US 6,638,919 B2
(45) Date of Patent: Oct. 28, 2003

(54) ANTIVIRAL PURINE DERIVATIVES

(75) Inventors: Christopher McGuigan, Whitchurch (GB); Jan Balzarini, Haverice (BE)

(73) Assignees: University College Cardiff Consultants Limited, Cardiff (GB); Rega Foundation, Leuven (BE)

( * ) Notice: Subject to any disclaimer, the term of this patent is extended or adjusted under 35 U.S.C. 154(b) by 0 days.

(21) Appl. No.: 09/825,554

(22) Filed: Mar. 27, 2001

(65) Prior Publication Data

US 2001/0031745 A1 Oct. 18, 2001

(51) Int. Cl.[7] .................. A61K 31/675; C07F 9/6561; A61P 31/18; A61P 31/20
(52) U.S. Cl. .......................... 514/81; 544/244
(58) Field of Search ................ 514/81; 544/244

(56) References Cited

U.S. PATENT DOCUMENTS 6,455,513 B1 * 9/2002 McGuigan et al. ........... 514/81

FOREIGN PATENT DOCUMENTS

| EP | 0 319 228 | 11/1988 |
|----|-----------|---------|
| EP | 0369409 A | 11/1989 |
| EP | 0434450 A | 12/1990 |
| EP | 0468866 A | 7/1991 |
| WO | PCT 92/06102 WO | 4/1992 |
| WO | 94/22882 | 10/1994 |
| WO | PCT 95/07920 WO | 3/1995 |
| WO | PCT 96/29336 WO | 9/1996 |
| WO | 98/16184 | 4/1998 |

OTHER PUBLICATIONS

Kahn et al, J. Infectious Diseases 183: 707 (2001).*
Foster R.H. & Faulds D. Drugs 1998 55 729–736.

* cited by examiner

*Primary Examiner*—Mark L. Berch
(74) *Attorney, Agent, or Firm*—Mathews, Collins, Shepherd & McKay, P.A.

(57) ABSTRACT

Compounds of the formula

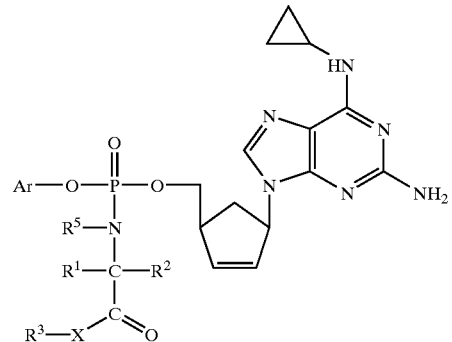

wherein Ar is aryl, $R^1$ and $R^2$ are hydrogen alkyl, alkyl substituted with phenyl, and aryl, O, NH, $NR^4$ and S, $R^5$ is hydrogen, alkyl or aryl or alkylene when taken with $R^1$, and $R^3$ is hydrogen, alkyl, alkyl substituted with phenyl, aryl, a heterocyclic group or a polycyclic group, are antiviral agents. A typical embodiment is (1S,4R)-4-[2-amino-6-(cyclopropylamino)-9H-purin-9-yl]-2-cyclopentene-1-methanol O-[phenyl-(methoxy-L-alaninyl)]phosphate.

19 Claims, No Drawings

ANTIVIRAL PURINE DERIVATIVES

The present invention relates to a chemical compound. In particular the present invention relates to a chemical compound suitable for use as an anti-viral agent. The present invention also relates to the therapeutic use of the present chemical compound, to a pharmaceutical composition containing the present compound and to use of the present compound in the manufacture of a medicament.

Since the recognition of human acquired immunodeficiency syndrome (AIDS) much interest and research activity has been directed to its understanding and to attempting to provide a means of treatment. The human immunodeficiency virus (HIV) has been identified as the presumed aetological agent in AIDS. A large literature now exists related to the use of a wide variety of chemical compounds having as their object a demonstration of anti-viral activity with respect to HIV, hepatitus B virus (HBV), herpes and other viruses.

A class of compounds which has demonstrated anti-viral activity and which has been the subject of a large amount of research are nucleoside analogues.

An example of such a compound is "Abacavir" which is a substituted adenine analogue (Foster R. H. & Faulds D. Drugs 1998 55 729–736). This compound has entered clinical use due to the potential activity and stability of the compound displayed in preliminary work.

PCT/GB96100580 relates to a class of nucleoside analogues said to be highly active with respect to HIV. In particular PCT/GB96/00580 addresses the problem of providing compounds which are said to be highly potent in vitro viral inhibitors in both TK⁻ and TK⁺ cells. The compounds disclosed in PCT/GB96/00580 are phosphoramidates of purine or pyrimidine nucleoside analogues. Such compounds can however display chemical, for example acid, or biological, for example nucleoside phosphorylase, instability towards glycoside bond cleavage. Consequential deactivation may limit their potential clinical efficacy.

A compound however to be potentially useful in a clinical setting needs to exhibit a number of other properties as well as demonstrating, at least in in vitro tests, a sufficient and desired anti-viral activity. Primarily, these other properties comprise good pharmacokinetic properties, sufficient stability in the compound to permit its ease of handling and supply, and sufficiently low toxicity to permit its administration with an acceptable level of side effects to a patient in need of treatment for the viral infection in question.

In practice however it is frequently found that attempts to modify a compound demonstrating anti-viral activity in vitro, in order to improve its other properties, can have a detrimental effect on the anti-viral activity it displays. Ideally moreover any compound proposed for clinical trials needs also to have a ready means of administration and to be prepareable by an economically viable route.

It is an object of the present invention to provide a novel class of compounds exhibiting potent anti-viral, in particular anti HIV and/or HBV activity, in combination with good pharmacokinetic and stability properties and exhibiting sufficiently low toxicity so as to provide a compound having beneficial properties for clinical use.

According to the present invention there is provided a compound according to the following formula (1):

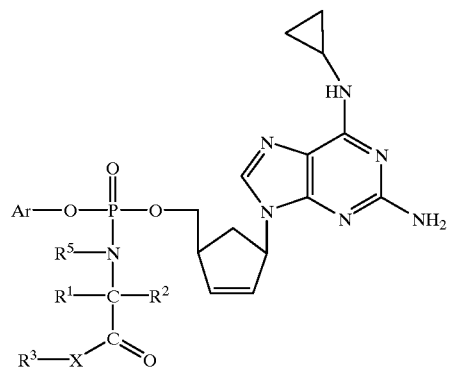

wherein
Ar is an aryl group,
$R^1$ and $R^2$ are independently selected from the group comprising H, alkyl and aryl groups;
X is selected from the group comprising O, NH, $NR^4$ and S wherein $R^4$ is selected from the group comprising alkyl and aryl groups;
$R^5$ is selected from the group comprising H, alkyl and aryl groups, wherein when $R^1$ and $R^5$ are each alkyl they may be linked to form a 5- or 6-membered ring;
and $R^3$ is selected from the group comprising H, al, aryl, heterocyclic and polycyslic groups,
or a pharmaceutically acceptable derivative or metabolite thereof.

The present invention includes salts and physiologically functional derivatives of the presently defined compounds.

Reference in the present specification to an alkyl group means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{16}$, more preferably $C_1$ to $C_6$, more preferably methyl or ethyl.

Reference in the present specification to an aryl group means an aromatic group, such as phenyl or naphthyl, or a heteroaromatic group containing one or more, preferably one, heteroatom for example O, N and/or S, such as pyridyl, pyrrolyl, furanyl and thiophenyl. Preferably, the aryl group comprises phenyl or substituted phenyl.

The alkyl and aryl groups may be substituted or unsubstituted, preferably unsubstituted. Where substituted, there will generally be 1 to 3 substituents present, preferably 1 substituent. Substituents may include halogen atoms and halomethyl groups such as $CF_3$ and $CCl_3$; oxygen containing groups such as oxo, hydroxy, carboxy, carboxyalkyl, alkoxy, alkoyl, alkoyloxy, aryloxy, aryloyl and aryloyloxy; nitrogen containing groups such as amino, alkylamino, dialkylamino, cyano, azide and nitro; sulphur containing groups such as thiol, alkylthiol, sulphonyl and sulphoxide, heterocyclic groups which may themselves be substituted; alkyl groups, which may themselves be substituted; and aryl groups, which may themselves be substituted, such as phenyl and substituted phenyl. Alkyl includes substituted and unsubstituted benzyl. Reference in the present specification to alkoxy and aryloxy groups means alkyl-O— and aryl-O— groups, respectively. Reference to alkoyl and aryloyl groups means alkyl-CO— and aryl-CO—, respectively.

Reference in the present specification to heterocyclic groups means groups containing one or more, optionally bridged, rings containing 1 to 6 heteroatoms in total. Each ring in the group may contain 3 to 12, preferably 1 to 6, atoms in total. At least one ring present contains 1 to 2 heteroatoms. Where two or more rings are present they may be fused or unfused. The rings can contain unsaturation. Heteroatoms includes 0, S and N. Examples of such heterocyclic groups containing one or more pyrrolyl, imidazolyl, pyrazolyl, thiazolyl, isothiazolyl, oxazolyl, pyrrolidinyl, pyrrolinyl, imidazolidinyl, imidazolinyl, yrazolidinyl, tetrahydrofuranyl, pyranyl, pyronyl, pyridyl, pyrazinyl, pyridazinyl, piperidyl, piperazinyl, morpholinyl, thionaphthyl, benzofuiranyl, isobenzofiyl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxadinyl, chromenyl, chromanyl, isochromanyl and carbolinyl.

References in the present specification to polycyclic groups means a group comprising two or more non-aromatic carbocyclic or heterocyclic rings which may themselves be substituted. Preferably the group contains 2 to 4 fused or non-fuised rings, each ring suitably containing 3 to 12 atoms, more suitably 4 to 10, more suitably 5 to 7, and even more suitably 5 to 6 atoms. The definitions of cyclic alkyl and heterocyclic rings given above also apply to the rings in the polycyclic groups.

Reference in the present specification to halogen means a fluorine, chlorine, bromine or iodine radical, preferably fluorine or chlorine radical.

The group Ar comprises a substituted or unsubstituted aryl group, wherein the term "aryl group" and the possible substitution of said group is as defined above. Preferably, Ar is a substituted or unsubstituted phenyl group. Particularly preferred substituents are electron withdrawing groups such as halogen (preferably chlorine or fluorine), trihalomethyl (preferably trifluoromethyl), cyano and nitro groups. Preferably, Ar is phenyl, 3,5-dichloro-phenyl, p-trifluoromethyl-phenyl, p-cyano-phenyl, or p-nitrophenyl.

$R^3$ is selected from hydrogen, alkyl, aryl, heterocyclic and polycyclic groups.

Preferably, $R^3$ is a substituted or unsubstituted alkyl group. Preferably, $R^3$ is a substituted or unsubstituted $C_{1-6}$ alkyl group, more preferably an ethyl or methyl group.

Preferably, at least one of $R^1$ and $R^2$ is hydrogen. It will be appreciated that if $R^1$ and $R^2$ are different, the carbon atom to which they are bonded is an asymmetric centre. Preferably this carbon atom is chiral. When this carbon atom is chiral, the stereochemistry at this site may be D or L or mixed, with L-stereochemistry being preferred. $R^5$ and $R^1$ can be linked to form an alkylene bridge comprising 3 to 4 carbon atoms so as to form a 5- or 6-membered ring. Preferably $R^5$ is hydrogen.

It will be appreciated that the group —NH—$CHR^1$—$CO_2R^3$ corresponds to a carboxy-protected α-amino acid. Preferably, the group $R^1$ corresponds to the side chain of a naturally occurring amino acid such as Alanine, Arginine, Asparagine, Aspartic Acid, Cysteine, Cystine, Glycine, Glutanic Acid, Glutamine, Histidine, Isoleucine, Leucine, Lysine, Methionine, Phenylalanine, Proline, Serine, Threonine, Tryptophan, Tyrosine, Valine. Preferably, $R^1$ is Me or $PhCH_2$ corresponding to the side chain of alanine or phenylalanine, respectively. Preferably, the stereochemistry at the asymmetrc centre —$CHR^1$— corresponds to an L-amino acid.

It is a feature of the aryl ester phosphate compounds of the present invention that they exhibit significantly enhanced anti-viral efficacy in in vitro tests, in comparison to their corresponding nucleoside analogue, (1S,4R)-4-[2-anino-6-(cyclopropylamino)-9H-purin-9-yl]-2-cyclopentene-1-methanol, which is known as Abacavir and which has the following structural formula:

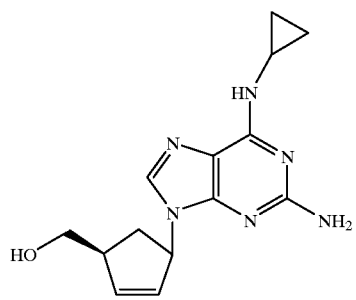

According to a further aspect of the present invention there is provided a compound of formula (II):

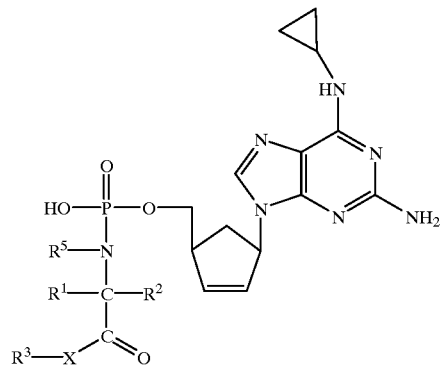

wherein $R^1$, $R^2$, $R^3$, $R^5$ and X are as defined above, or a pharmaceutically acceptable derivative or metabolite thereof. Preferably X is O.

The intracellular generation of such anti-viral metabolites is an important feature of the invention for several reasons. In cases where the nucleoside is not a good substrate for host nucleotide kinases, activation will be poor and anti-viral efficacy low, even if the triphosphate is an excellent RT inhibitor. In such cases, the generation of the present metabolites may lead to a very significant enhancement in anti-viral action.

By "a pharmaceutically acceptable derivatives" is meant any pharmaceutically acceptable salt, ester or salt of such ester or any other compound which upon administration to a recipient is capable of providing (directly or indirectly) a compound of the present formula or present metabolite. Preferred "pharmaceutically acceptable derivatives" include sodium, succinate, fumarate, glutarate and D-tartrate salts.

By "pharmaceutically acceptable metabolite" is meant a metabolite or residue of a compound of the present formula or present metabolite which gives rise to reverse transcriptase inhibition exhibited by the present compounds.

According to a further aspect of the present invention there is provided a compound according to the present invention for use in a method of treatment, preferably in the prophylaxis or treatment of viral infection.

According to a further aspect of the present invention there is provided use of a compound according to the present invention in the manufacture of a medicament for the prophylaxis or treatment of viral infection.

According to a further aspect of the present invention there is provided a method of prophylaxis or treatment of viral infection comprising administration to a patient in need of such treatment an effective dose of a compound according to the present invention.

The viral infection may comprise any viral infection such as HIV and herpes vinis, including HSV I and HSV 2, CMV, VZV, EBV, HAV, HBV, HCV, HDV, HHV6, HHV7, HHV8, papilloma, adenoviruses, rabies and influenza.

Preferably, the viral infection comprises HIV or HBV infection, more preferably HIV-I or HIV-II. It is a feature of the present invention that the compounds exhibit good activity against HIV-I and HIV-II, and HBV.

According to a further aspect of the present invention there is provided a pharmaceutical composition comprising a compound of the present invention in combination with a pharmaceutically acceptable excipient.

According to a further aspect of the present invention there is provided a method of preparing a pharmaceutical composition comprising the step of combining a compound of the present invention with a pharmaceutically acceptable excipient.

Compounds of the present invention can demonstrate significant stability towards acid-mediated hydrolytic decomposition. The present compounds can thus be particularly suitable for oral administration under typical dosing conditions in humans as they can retain stability under the highly acidic environment of the stomach.

As the purine in compounds of formula (I) is a weak base (pKa=5.0) and the compounds of formula (a) demonstrate stability to acids, salts can be formed of compounds of formula (1) with acids, such as carboxlic acids and dicarboxlic acids. Such salts can be stable, crstalline solids, which can be beneficial in terms of improved shelf-life and ease of handling during manufacture into pharmaceutical compositions. Preferred carboxylic and dicarboxylic acids include malonic, succinic, glutaric, fumaric and tartaric acids. In contrast to the salts of compounds of formula (I), the free bases of compounds of formula (I) can be in a non-crystalline amorphous form which can be hygroscopic.

The P-OH group of compounds of formula (II) is a weak acid and can therefore form monobasic salts with bases to give, for example, sodium, potassium, ammonium, and triethylanmmonium salts. In. compounds of fonnula (II) when X is OH, dibasic salts can be formed. Such dibasic salts can be in the form of stable solids, which can provide benefits of improved shelf-life and ease of handling during manufacture into pharmaceutical compositions.

Compounds of the present invention can also demonstrate enhanced stability in biological media, for example, in human plasma. The increased half-life of compounds embodying the present invention in media such as human plasma may permit a pharamacokinetic advantage in dosing in humans in need of treatment.

The medicament employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouing agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.01 to 10 mg per kilogram body weight of the recipient per day, preferably in the range of 0.2 to 1.0 mg per kilogram body weight per day. The desired dose is preferably presented once daily, but may be dosed as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

According to a further aspect of the present invention there is provided a process for the preparation of the present compound comprising reaction of a compound of formula

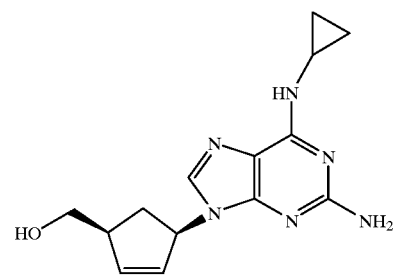

with a compound of formula

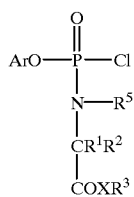

wherein $R^1$, $R^2$, $R^3$, $R^5$ and X have the meanings given above.

The reaction may be carried out under dry conditions at ambient temperature in tetrahydrofuran in the presence of N-methylimidazole, or by using t-butyl magnesium chloride and an excess of the appropriate phosphorochlorideate reagent.

Compounds embodying the present invention wherein Ar is replaced by H may be prepared from the acid form by treatment of the ester with an aqueous base.

Compounds wherein X is NH or $NR_4$ can be prepared by treating the acid form (X=O and $R^3$=H) with amine.

The above starting material, (1S, 4R)-4-[2-amino-6-(cyclopropylamino)-9H-purin-9-yl]-2-cyclopentenel-methanol, is known as Abacavir and may be made by any procedure known in the art, for example by procedures described in European Patent Specification Number 0434450, PCT Patent Application No. PCT/GB95/02014, and PCT Patent Application No. PCT/EP98/02835, all of which are incorporated by reference thereto.

The invention will now be described with reference to the following Examples. It will be appreciated that what follows is by way of example only and that modifications to detail may be made whilst still falling within the scope of the invention.

EXPERIMENTAL PROCEDURES

General Methods

The following anhydrous solvents and reagents were bought dry from Aldrich with sure seal stoppers: Dichloromethane (DCM), diethyl ether ($Et_2O$), tetrahydrofuran (A), N-methyl imidazole (NMI), methanol (MeOH), dimethylformamide (DMF), pyridine (pyr), dioxane, and tBuMgCl. Triethylamine ($NEt_3$) was dried by refluxing over $CaH_2$ for several hours and then distilled off for immediate use.

Chromatography

Thin layer chromatography (tlc) was performed on commercially available Merck Kieselgel $60F_{254}$ plates and the separated components were visualised using ultra violet light (254 nm and 366 nm), or by treatment with a 5% ethanolic solution of dodeca-molybdo-phosphoric acid (MPA) followed by heating. Column chromatography was performed using Woelm silica (32–63 mm) as the stationary phase.

Spectral Characterisation

All NMR spectral data, unless otherwise stated, were obtained in $CDCl_3$. Proton and Carbon-13 nuclear magnetic resonance were recorded on a Bruker Avance DPX300 spectrometer with operating frequencies of 300 MHz and 75 MHz respectively. Phosphorous-31 NMR spectra were recorded on a Bruker Avance DPX300 spectrometer operating at 121 MHz, and are reported in units of δ relative to 85% phosphoric acid as the external standard, positive shifts are downfield. The following abbreviations are used in the assignment of NMR signals: s (singlet), d (doublet), t (triplet), q (quartet), m (multiplet), bs (broad signal), dd (double of doublets), dt (double of triplets).

Low resolution mass spectra were run on a VG Platform II Fisons instrument (Fisons, Altrincham, UK) (atmospheric pressure ionization, electrospray mass spectrometry) in either negative or positive ion mode.

High Performance Liquid Chromatography (HPLC) was performed on an SSODS2 reverse phase column with an eluent of water/acetonitrile. 100% water (0 mins), 20% water (35 mins), 20% water (45 mins), 100% water (55 mins), with a flow rate of I ml/min and detection by UV at 254 mn. Standards: acetone ($t_R$ 4.54 mins), toluene (tR 10.21 mins). Final products showed purities >99%, with undetectable amounts of the parent nucleoside.

Nomenclature and Numbering of Compounds

IUPAC nomenclature is used where possible, but for ease some compounds are abbreviated. Numbering is by conventional nucleoside numbering.

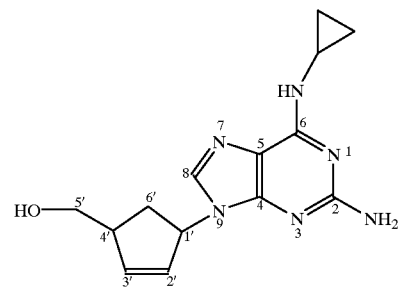

Standard Procedures

For practical purposes, standard procedures are given where applicable.

Standard Procedure 1

To a stirring solution of anhydrous alcohol (10 mol eq) was added thionyl chloride (2 mol eq) dropwise at 0° C., and the resulting solution stirred for Ihr. Upon rising to room temperature, the appropriate amino acid (1 mol eq) was added and the reaction heated at reflux for 6–16 hrs. Removal of the solvent and recrystallisation from methanol:ether gave the amino ester hydrochloride salts.

Standard Procedure 2

The appropriate amino acid (1 mol eq), para-toluene sulfonic acid (1.1 mol eq) and the appropriate alcohol (Imol eq) were heated under reflux in toluene (100 ml), under Dean and Stark conditions, for 6–16 hrs. On cooling to room temperature the solvent was removed under reduced pressure to give an oil. This was solubilised in dichloromethane (50 ml) and washed with 10% $K_2CO_3$ (50 ml), and water (50 ml), filtered and the filtrate reduced to dryness to give an oil. This was solubilised in the minimum amount of acetone and neutralised with 2M HCl, and then lyophilised to give the amino acid ester hydrochloride salts.

Standard procedure 3

Phenyl dichlorophosphate (1 mol eq) and the appropriate amino acid ester hydrochloride salt (1 mol eq) were suspended in anhydrous dichloromethane (30–60 ml). Anhydrous triethylamine (2 mol eq) in anhydrous dichloromethane (30 ml) was added dropwise at −80° C., and the reaction left to rise to room temperature overnight. The solvent was removed under reduced pressure, and under nitrogen, to give white solids. This was washed with anhydrous ether (2×25 ml), filtered and the filtrate reduced to dryness to give the products as crude oils. These were stored in anhydrous THF and used without any further purification.

Standard Procedure 4

(1 S,4R)-4-(2-amino-6-cyclopropylamino-9H-purin-9-yl)-2-cyclopentene-1-methanol (1 mol eq) was dried by azeotroping with anhydrous pyridine (3×5 ml), and then suspended in anhydrous THF (5–30 ml). To the suspension was added tBuMgCl (1–2 mol eq, 1.0M solution in THF) dropwise, and the resulting suspension stirred for 10 mins. The phosphorochloridate species (3 mol eq, solution in THF) was then added dropwise and the resulting solution stirred at room temperature for 24–96 hrs. The reaction was then quenched by the addition of sat.NC$_4$Cl (0.1 ml), and after 10 mins the solvent was removed under reduced pressure. The crude product was purified by silica column chromatography.

L-Alanine methyl ester hydrochloride.
$C_4H_{10}O_2N_1Cl_1$, MW=139.38.

This was synthesised according to Standard Procedure 1, using anhydrous methanol (34 ml, 0.84 mol), thionyl chloride (8.2 ml, 0.112 mol) and L-alanine (5.0 g, 0.056 mol). The product was isolated as a white solid (2.87 g, 36.7%).
$^1$H NMR (D$_2$O): δ4.074.00 (1H,q,CH,J=7.22 Hz), 3.83 (3H,s,OCH$_3$), 1.39–1.37 (3H,t,CH$_3$).
$^{13}$C NMR (D2O): δ171.5 (CO), 53.9 (O CH$_3$), 49.1 (CH), 15.4 (CH$_3$).

Phenyl-(methoxy-L-alaninyl)-phosphorochloridate.
$C_{10}H_{13}O_4N_1Cl_1P_1$, MW=277.65.

This was synthesised according to Standard Procedure 3, using L-Alanine methyl ester hydrochloride (2.0 g, 14.34 mmol), phenyl phosphorodichloridate (3.02 g, 2.14 ml, 14.34 mmol) and anhydrous triethylamine (2.90 g, 4.0 ml, 28.68 mmol). The product (3.91 g, 98.2%) was isolated as a colourless crude oil which was stored in anhydrous THF (40 ml) to give a 0.47M solution.
$^{31}$p NMR: δ9.28, 8.97 (1:1).
$^1$H NMR: δ7.39–7.34 (2H,m,'o'-Ph), 7.29–7.20 (3H,m,'m'+'p'-Ph), 4.494.37 (1H,q,NHala), 4.27–4.09 (1H,m,CHala), 3.78 (3H,d,OCH$_3$), 1.52–1.49 (3H,dd,CH$_3$).
$^{13}$C NMR: 173.6 (CO), 150.1 ('ipso'-Ph), 130.25 ('m'-Ph), 126.4 ('p'-Ph), 120.9 ('o'-Ph), 53.2 (OCH$_3$), 51.0 (CH), 20.9 (CH$_3$ala).

(1S,4R)-4-(2-amino-6-cyclopropylamino-9H-purin-9-yl)-2-cyclopentene-1-methanol O-[phenyl-(methoxy-L-alaninyl)]-phosphate. Cf1490.
$C_{24}H_{30}O_5N_7P_1$, MW=527.53.

This was synthesised according to Standard Procedure 4, using (1S,4R)-4-(2-amino-6-cyclopropylamino-9H-purin-9-yl)-2-cyclopentene-1-methanol (500 mg, 1.75 mmol), tBuMgCl (1.0M solution in THF) (1.75 ml, 1.75 mmol) and phenyl-(methoxy-L-alaninyl)-phosphorochloridate (0.47M solution in THF) (1 1.17 ml, 5.24 mmol), in THF (30 ml) and stirring at room temperature for 70 hrs. The crude product was purified by column chromatography eluting with 3% MeOH in DCM and then 2% MeOH in DCM to give the product as a white foam (442 mg, 48%).
$^{31}$P NMR (MeOH-d$_4$): δ3.97, 3.88.
$^1$H N: δ7.41 (1H,d,C8), 7.24–7.19 (2H,m,'o'-Ph), 7.13–7.03 (3H,m,'m'+'p'-Ph), 6.08 (1H,bs,NH), 5.98 (1H,q,H2'), 5.78 (t,H3'), 5.44 (1H,t,H1'), 5.09 (2H,bs,NH$_2$), 4.22–4.02 (3H,m,NHala+H5'), 3.99–3.87 (1H,m,CHala), 3.59 (3H,t,OCH$_3$), 3.05 (1H,d,H4'), 2.92 (1H,bs,CHcPr), 2.73–2.62 (1H,m,'o'H6'), 1.62–1.53 (1H,m,'o'H6'), 1.30–1.25 (3H,t,CH$_3$ala), 0.78–0.71 (2H,q,2H of CH$_2$cPr), 0.54–0.49 (2H,t, 2H of CH$_2$cPr).
$^{13}$C NMR: δ174.6 LCO), 160.3 (C2), 156.6 (C4), 151.3 (C6), 151.1 ('ipso'-Ph), 136.8 (C8), 135.9 (C2'), 131.5 (C3'), 130.0 ('m'-Ph), 125.2 ('p'-Ph), 120.5 ('o'-Ph), 115.0 (C5), 69.2 (C5'), 59.2 (C1'), 52.8 (OCH$_3$), 50.5 (CHala), 46.0 (C4'), 34.9 (C6'), 24.2 (CHcPr), 21.2 (CH$_3$ala), 7.7 (CH$_2$cPr).
MS ES$^+$: m/z 527.86 (100%) (M)$^+$, 546.84 (M+K)$^+$.
MS FAB: For $C_{24}H_{31}O_5N_7P$, requires 528.212431, found 528.213848.
HPLC: tR 30.33 (100%)-(100% water (0 mins), 20% water (35 mins), 20% water (45 mins), 100% water (55 mins)).
IR: 3328.6 (N-Hstr.), 2922.1, 2862.9 (C-Hstr.), 1734.4 (C-Ostr.), 1590.9 (aromatic C-Cstr.), 1462.9 (C-Hdef), 1376.8 (-CH$_3$syM.def.), 1207.1 (P-O-aryl), 1154.0 (C-Ostr.), 1027.7 (P-O-alkyl), 933.4 (olefiric C-Hdef.), 721.8 (monosub.aromatic C-Hdef.).

Phenyl-(methoxy-D-alaninyl)-phosphorochloridate.
$C_{10}H_{13}O_4N_1Cl_1P_1$, MW=277.65.

This was synthesised according to Standard Procedure 3, using D-alanine methyl ester hydrochloride (1.0 g, 7.17 mmol), PhOP(O)Cl$_2$ (1.51 g, 1.07 ml, 7.17 mmol) and NEt$_3$ (1.45 g, 2.0 ml, 14.0 mmol) to yield 1.66 g (83.4%) of crude product that was stored in anhydrous THF (10 ml), to give a 0.60 mmol/ml solution that was used without further purification.
$^{31}$P NMR: δ9.38, 9.18 (1:1).
$^1$H NMR: δ7.39–7.30 (2H,t,'o'-Ph), 7.29–7.09 (3H,m,'m'+'p'-Ph), 4.85–4.80 (1H,d,NHala), 4.19–4.11 (1H,m,CHala), 3.75 (3H,d,OCH$_3$), 1.52–1.49 (3H,dd,CH$_3$ala).
$^{13}$C NMR: δ173.6 (CO), 150.1 ('ipso'-Ph), 130.3 ('o'-Ph), 126.4 ('p'-Ph), 120.9 ('m'-Ph), 53.2 (OCH$_3$), 50.9 (CHala), 21.0 (CH$_3$ala).

(1 S,4R)-4-(2-amino-6-cyclopropyiamino-9H-purin-9-yl)-2-cyclopentene-1-methanol O-[phenyl-(methoxy-D-alaninyl)]-phosphate. Cf1583.
$C_{24}H_{30}O_5N_7P_1$, MW=527.53.

This was synthesised according to Standard Procedure 4, using (1S,4R)1(2-amino-6-cyclopropylamino-9H-purin-9-yl)-2-cyclopentene-1-methanol (400 mg, 1.4 mmol), tBuMgCl (1.0M solution in THF) (2.1 ml, 2.1 mmol), and phenyl-(methoxy-D-alaninyl)-phosphorochloridate (0.6M solution in THF) (7.0 ml, 4.19 mmol) in THF (25 ml) stirring at room temperature for 36 hrs. The crude product was purified by eluting with 3% MeOH in CHCl$_3$ and then 2.5% MeOH in CHCl$_3$ to give the product as a white foam (318.6 mg, 43.2%).
$^{31}$p NR: 3.93, 3.70.
$^1$H NMR: δ7.56+7.51 (1H,d,H8), 7.37–7.32 (2H,m,'o'-Ph), 7.29 (1H,d,'p'-Ph), 7.25–7.15 (2H,m,'m'-Ph), 6.10 (1H,t,J= 5.28 Hz,H2'), 6.03 (1H,bs,NHcPr), 5.94–5.89 (1H,m,H3'), 5.54 (1H,bs,H1'), 5.01 (2H,bs,NH$_2$), 4.26–3.83 (4H,m, CHala,NHala+H5'), 3.72 (3H,d,OCH$_3$), 3.18 (1H,s,CHcPr), 3.02 (1H,bs,H4'), 2.86–2.75 (1H,m,1 of H6'), 1.78–1.64 (1H,m,1 of H6'), 1.39–1.36 (3H,dd,CH$_3$ala), 0.90–0.83 (2H, q,J=6.13 Hz,2H of CH$_2$cPr), 0.63 (2H,bs, 2H of CH$_2$cPr).
$^{13}$C NMR: δ174.5 (CO), 160.3 (C2), 156.6 (C4) 151.2 (C6), 151.0 ('ipso'-Ph), 13608 (C2'), 136.1 (C8), 131.5 (C3'), 130.0 ('m'-Ph), 125.3 ('p'-Ph), 120.5 ('o'-Ph), 115.2 (C5), 69.3 (C5'), 59.3 (C1'), 52.9 (CHala), 50.5 (OCH$_3$), 46.0 (C4'), 34.9 (C6'), 24.1 (CHcPr), 21.4 (CH$_3$ala), 7.8 (CH$_2$cPr).
MS ES$^+$: m/z 527.86 (100%) (M)$^+$, 546.84 (M+K)$^+$.

MS FAB: For $C_{24}H_{31}O_5N_7P$ requires 528.212431, found 528.211505.
HPLC: tR 29.807 (100%)-(100% water (0 mins), 20% water (35 mins), 20% water (45 mins), 100% water (55 mins)).
IR: 3333.6 (N-Hstr.), 2923.4, 2853.4 (C-Hstr.), 1734.1 (C=Ostr.), 1591.1 (aromatic C-Cstr.), 1458.3 (C-Hdef.), 1376.7 (-$CH_3$syM.def.), 1208.3 (P-O-aryl), 1153.3 (C-Ostr.), 1026.9 (P-O-alkyl), 931.9 (olefinic C-Hdef), 721.6 (monosub.aromatic C-Hdef).
Phenyl-(methoxy-L-phenylalaninyl)-phosphorochloridate. $C_{16}H_{17}O_4N_1Cl_1, P_1$, MW=353.74.

This was synthesised according to Standard Procedure 3, using L-phenylalanine methyl ester (1.0 g, 4.64 mmol), PhOP(O)$Cl_2$ (0.98 g, 0.70 ml, 4.64 mmol) and $NEt_3$ (0.94 g, 1.30 ml, 9.28 mmol) to yield 1.45 g (88.4%) of crude product as an oil that was stored in anhydrous THF (10 ml), to give a 0.41 mmol/ml solution that was used without farther purification. 31p NMR: 6 9.37, 9.23 (1:1).
$^1$H NMR: δ7.60–7.16 (10H,m,2xPh), 4.704.49 (1H,m, CHala), 4.38–4.16 (1H,m,NHala), 3.89 (3H,d,$OCH_3$), 3.23 (2H,m,CHPh).
(1,S,4R)-4-(2-amino-6-cyclopropylamino-9H-purin-9-yl)-2-cyclopentee-1-methain O-[phenyl-(methoxy-L-phenylalaninyl)]-phosphate. Cf 1585.
$C_{31}H_{34}O_5N_7P$, MW=603.6.

This was synthesised according to Standard Procedure 4, using (1S,4R)-4-(2-amino-6-cyclopropylamino-9H-purin-9-yl)-2-cyclopentene-1-methanol (300 mg, 1.05 mmol), tBuMgCl (1.0M solution in THF) (1.57 ml, 1.57 mmol) and phenyl-(methoxy-L-phenylalaninyl)-phosphorochloridate (0.41M solution in THF) (7.66 ml, 3.14 mmol) in THF (20 ml) stirring at room temperature for 48 hrs. The crude product was purified by eluting with 3% MeOH in $CHCl_3$ and then 2.5% MeOH in $CHCl_3$ to give the product as a white foam (272.9 mg, 43.15%).
$^{31}$p NMR: δ3.91, 3.80.
$^1$H NMR: δ7.47+7.43 (1H,d,H8), 7.31–7.06 (IOH,m,2xPh), 6.25 (1H,d,NHcPr), 6.00–5.95 (1H,q,H2'), 5.87–5.81 (1H,t, H3'), 5.49 (1H,s,H1'), 5.19 (2H,bs,$NH_2$), 4.31–3.92 (4H,m, CHala,NHala+H5'), 3.64 (3H,d,$OCH_3$), 3.02–2.89 (4H,m, $CH_2$Ph,CHcPr+H4'), 2.78–2.63 (1H,m,1 of H6'), 1.63–1.49 (1H,m,l of H6'), 0.86–0.80 (2H,q,J=6.24 Hz,2H of $CH_2$cPr), 0.60 (2H,d,2H of $CH_2$cPr).
$^{13}$C NMR: δ74.3 (CO), 161.5 (C2), 157.7 (C4), 152.4 (C6) 152.1 ('ipso'-OPh), 137.7 ('ipso'-Bn), 137.1 (C2'), 136.9 (C8), 132.4 (C3'), 130.9 ('o'+'m'-Bn), 129.9 ('m'-mOPh), 128.4 ('p'-Bn), 126.2 ('p'-OPh), 121.5 ('o'-OPh), 116.1 (C5), 70.1 (C5'), 60.1 (Cl'), 57.2 (CHala), 53.6 ($OCH_3$), 46.9 (C6'), 41.7 (C4'), 35.9 ($CH_2$Ph), 25.1 (CHcPr), 8.7 ($CH_2$cPr).
MS ES$^+$: m/z 603.8 (100%, M+), 604.8 (35%, M+H$^+$), 625.7 (15%, M+Na$^+$).
MS FAB: For $C_{31}H_{34}O_5N_7P$ requires 604.243731, found 604.242585.
HPLC: $t_R$ 34.707, 35.020 (100%)-(100% water (0 mins), 20% water (35 mins), 20% water (45 mins), 100% water (55 mins)).
IR: 3331.7 (N-Hstr.), 3007.2, 2952.2 (C-Hstr.), 1741.1 (C=Ostr.), 1595.6, 1487.7 (aromatic C-Cstr.), 1455.0 (C-Hdef), 1393.9 (—$CH_3$sym.def.), 1252.5 (P=O), 1214.3 P-0-myl), 1125.3 (C-Ostr.), 1025.6 (P-O-alkyl), 935.8 (olefinic C-Hdef.), 754.8 (monosub.aromatic C-Hdef.).
Phenyl-(methoxyglycinyl)-phosphorochloridate. $C_9H_{11}O_4N_1Cl_1,P_1$, MW=263.62.

This was synthesised according to Standard Procedure 3, using glycine methyl ester (1.5 g, 11.9 mmol), PhOP(O)$Cl_2$ (2.52 g, 1.79 ml, 11.9 mmol) and $NEt_3$ (2.42 g, 3.33 ml, 23.9 mmol) to yield 3.07 g (97.15%) of crude product as an oil that was stored in anhydrous THF (15 ml), to give a 0.774 mmol/ml solution that was used without further purification.
$^{31}$p NMR: δ10.43.
$^1$H NMR: δ7.43–7.38 (2H,m,'o'-Ph), 7.31–7.25 (3H,m, 'm'+'p'-Ph), 4.67 (1H,bs,NHala), 3.94 (2H,dd,$CH_2$), 3.83 (3H,s,$OCH_3$).
$^{13}$C NMR: δ170.4 (CO), 150.1 ('ipso'Ph), 130.2 ('m'-Ph), 126.4 ('p'-Ph), 120.8 ('o'-Ph), 53.1 ($OCH_3$), 43.4 ($CH_2$).
(1 S,4R)-4-(2-amino-6-cyclopropylamino-9H-purin-9-yl)-2-cyclopentene-1-methanol O-[phenyl-(methoxy-glycinyl)]-phosphate. Cf1588.
$C_{23}H_{28}O_5N_7P_1$, MW=513.49.

This was synthesised according to Standard Procedure 4, using (1S,4R)-4-(2-amino-6-cyclopropylamino-9H-purin-9-yl)-2-cyclopentene-1-methanol (300 mg, 1.05 mmol), tBuMgCl (1.0M solution in THF) (1.57 ml, 1.57 mmol) and phenyl-(methoxy-glycinyl)-phosphorochloridate (0.774M solution in THF) (4.06 ml, 3.14 mmol) in THF (20 ml) stirring at room temperature for 96 hrs. The crude product was purified by eluting with 3% MeOH in $CHCl_3$ and then with 2.5% MeOH in $CHCl_3$ to give the product as a white foam (82.6 mg, 15.4%).
$^{31}$p NMR: δ4.79, 4.67 (1:1).
$^1$H NMR: δ7.40+7.36 (1H,dH8), 7.24–7.19 (2H,t,'o'-Ph), 7.15–7.10 (2H,t,'m'-Ph), 7.07–7.02 (1H,t,'p'-Ph), 6.00–5.96 (2H,m,H2'+NHcPr), 5.80–5.76 (1H,m,H3'), 5.45–5.41 (1H,tH1'), 4.99 (2H,bs,$NH_2$), 4.14–4.00 (3H,m, NHala+H5'), 3.62 (3H,s,$OCH_3$), 3.03 (1H,d,H4'), 2.91 (1H, d,CHcPr), 2.73–2.62 (1H,m,1of H6'), 1.62–1.51 (1H,m,1 of H6'), 1.45–1.43 (6H,t,2x$CH_3$), 0.78–0.71 (2H,q,2H of $CH_2$cPr), 0.54–0.49 (2H,t,2H of $CH_2$cPr).
$^{13}$C NMR: δ172.1 ($\underline{C}$O), 160.2 (C2), 156.6 (C4), 152.0 (C6), 151.7 ('ipso'-Ph), 137.7 (C8), 137.1 (C2'), 132.0 (C3'), 130.8 ('m'-Ph), 126.0 ('p'-Ph), 121.2 ('o'-Ph), 115.5 (C5), 69.9 (C5'), 60.0 (Cl'), 53.5 ($OCH_3$), 46.7 (C4'), 43.9 ($CH_2$), 35.4 (C6'), 25.0 (CHcPr), 8.5 ($CH_2$cPr).
MS ES$^+$: m/z 513.9 (100%, M$^+$), 514.8 (25%, M+H$^+$), 535.8 (40%, M+Na$^+$).
MS FAB: For $C_{23}H_{29}O_5N_7P$ requires 514.196781, found 514.195321.
HPLC: $t_R$ 28.419 (99.9%)-(100% water (0 mins), 20% water (35 mins), 20% water (45 mins), 100% water (55 mins)).
IR: 3342.0 (N-Hstr.), 1749.8 (C=Ostr.), 1596.2, 1488.4 (aromatic C-Cstr.), 1451.9 (C-Hdef.), 1394.7 (-$CH_3$sym.def.), 1259.6 (P=O), 1212.1 (P-O-aryl), 1151.6 (C-Ostr.), 1026.8 (P-O-alkyl), 937.8 (olefinic C-Hdef), 760.7 (monosub.aromaiic C-Hdef.).
Methyl-2-amino-2-methylpropanoate hydrochloride $C_5H_{12}O_2N_1Cl$, MW=153.61.

This was synthesised according to Standard Procedure 1, using 2-amino-isobutyric acid (4 g, 0.039 mol) with thionyl chloride (5.66 ml, 0.078 mol) and anhydrous methanol (23.5 ml, 0.58 mol). This gave the product as a white solid (5.805 g, 97.4%)
$^1$H NMR (DMSO): δ8.85 (3H,s,NH+Cl), 3.72 (3H,s,OMe), 1.48 (6H,s,2xMe).
$^{13}$C NMR (DMSO): δ172.8 ($\underline{C}$OOMe), 56.6 (OMe), 53.9 ($\underline{C}Me_2$), 24.1 (2xMe).
MS ES$^+$: m/z 117.71 M+H$^+$, 142.88 M+Na$^+$.
Phenyl-(methyl-2-amino-2-methylpropanoate)-phosphorochloridate.
$C_{11}H_{15}O_4N_1Cl_1P_1$, MW=291.67.

This was synthesised according to Standard Procedure 3, using 2-amino-isobutate methyl ester hydrochloride (1.0 g, 6.51 mmol), PhOP(O)$Cl_2$ (1.37 g, 0.97 ml, 6.51 mmol) and $NEt_3$ (1.32 g, 1.18 ml, 13.02 mmol), to yield 1.73 g (91%)

of the crude product as an oil. This was stored in anhydrous THF (10 ml) to give a solution of 0.593 mmol/ml, and used without further purification.

$^{31}$P NMR: δ6.86.

1H NMR: δ7.43–7.38 (2H,t,'o'-Ph), 7.32–7.21 (3H,m,'m'+'p'-Ph), 4.84 (1H,d,NHala), 3.83 (3H,s,OCH$_3$), 1.72 (6H,d, 2xCH$_3$).

$^{13}$C NMR: δ175.7 (CO), 150.3 ('ipso'-Ph), 130.3 ('m'-Ph), 126.3 ('p'-Ph), 121.0 ('o'-Ph), 58.8 (OCH$_3$), 53.6 ( C[CH$_3$]$_2$), 27.3+27.0 (2xCH$_3$).

(1S,4R)-4-(2-amino-6-cyclopropylamino-9H-purin-9-yl)-2-cyclopentene-1-methanol O-[phenyl-(methoxy-α,adimethylglycinyl)]-phosphate. Cf 1584.

C$_{25}$H$_{32}$O$_5$N$_7$P$_1$, MW=542.23.

This was synthesised according to Standard Procedure 4, using (1S,4R)-4-(2-amino-6-cyclopropylamino-9H-purin-9-yl)-2-cyclopentene-1-methanol (300 mg, 1.05 mmol), tBuMgCl (1.0M solution in THF) (1.57 ml, 1.57 mmol) and phenyl-(methoxy-dimethylglycinyl)-phosphorochloridate (0.59M solution in THF) (5.3 ml, 3.14 mmol) in THF (20 ml) stirring at room temperature for 96 hrs. The crude product was purified by eluting with 3% MeOH in CHCl$_3$ and then with 2.5% MeOH in CHCl$_3$ to give the product as a white foam (193.7 mg, 34.14%).

$^{31}$p NMR: δ2.49. $^1$H NMR: δ7.40+7.36 (1H,d,H8), 7.24–7.19 (2H,t,'o'-Ph), 7.15–7.10 (2H,t,'m'-Ph), 7.07–7.02 (1H,t,'p'-Ph), 6.00–5.96 (2H,m,H2'+NHcPr), 5.80–5.76 (1H,m,H3'), 5.45–5.41 (1H,t,H1'), 4.99 (2H,bs, NH$_2$), 4.14–4.00 (3H,m,NHala+H5'), 3.62 (3H,s,OCH$_3$), 3.03 (1H,d,H4'), 2.91 (1H,d,CHcPr), 2.73–2.62 (1H,m,1 of H6'), 1.62–1.51 (1H,m,1of H6'), 1.45–1.43 (6H,t,2xCH$_3$), 0.78–0.71 (2H,q,2H of CH$_2$cPr), 0.54–0.49 (2H,t,2H of CH$_2$cycl.).

MS ES$^+$: m/z 541.9 (100%, M$^+$), 563.8 (30%, M+Na$^+$).

MS FAB: For C$_{25}$H$_{33}$O$_5$N$_7$P requires 542.228081, found 542.228428.

HPLC: $t_R$ 28.347 (100%)-(100% water (0 mins), 20% water (35 mins), 20% water (45 mins), 100% water (55 mins)).

IR: 3346.0 (N-Hstr.), 2923.0, 2853.5 (C-Hstr.), 1734.0 (C=Ostr.), 1590.2 (aromatic C-Cstr.), 1458.4 (C-Hdef.), 1376.8 (-CH$_3$syn.def.), 1261.3 (P=O), 1152.7 (C-Ostr.), 1028.0 (P-O-alkyl), 936.0 (olefinic C-Hdef.), 721.7 (monosub.aromatic C-Hdef.).

L-Aspartic acid dimethyl ester hydrochloride.

C$_6$H$_{12}$O$_4$N$_1$C$_1$, MW=197.62.

This was synthesised according to Standard Procedure 1, using L-asparagine (2.5 g, 0.019 mol) with thionyl chloride (3.67 ml, 0.042 mol) and anhydrous methanol (12.86 ml, 0.32 mol). This gave L-aspartic acid dimethyl ester hydrochloride in 3.70 g, 99% yield. $^1$H NMR (MeOH-d$_4$): 5 4.53–4.50 (1H,t,CH), 3.94 (3H,s,OCH$_3$), 3.85 (3H,s,OCH$_3$), 3.18 (2H,d,CH$_2$).

$^{13}$C NMR (MeOH-d): δ170.4, 168.4 (CO), 53.0+52.0 (2xOMe), 49.4 (CH), 33.8 (CH$_2$).

Phenyl-(dimethoxy-L-aspartyl)-phosphorochloridate.

C$_{12}$H$_{15}$O$_6$N$_1$C$_1$P$_1$, MW=335.68.

This was synthesised according to Standard Procedure 3, using L-Aspartic acid dimethyl ester (1.0 g, 5.04 mmol), PhOP(O)Cl$_2$ (1,06 g, 0.75 ml, 5.04 mmol) and NEt$_3$ (1.02 g, 1.40 ml, 10.1 mmol) to yield 0.55 g (32.4%) of crude product as an oil that was stored in anhydrous THF (5 ml), to give a 0.33 mmol/ml solution that was used without further purification.

$^{31}$P NMR: δ9.74,9.59 (1:1).

(1S,4R)-4-(2-amino-6-cyclopropylamin9H-purin-9-yl)-2-cyclopentene-1-methanol O-[phenyl-(L-asparic acid dimethyl ester)]-phosphate. Cf1589.

C$_{24}$H$_{30}$O$_5$N$_7$P), MW=527.53.

This was synthesised according to Standard Procedure 4, using (1S,4R)-4-(2-amino-6-cyclopropylamino-9H-purin-9-yl)-2-cyclopentene-1-methanol (250 mg, 0.87 mol), tBuMgCl (1.0M solution in THF) (0.87 ml, 0.87 mmol) and phenyl-(L-aspartic acid dimethyl ester)-phosphorochloridate (0.50M solution in THF) (5.20 ml, 2.62 mmol) in THF (15 ml) and stirring at room temperature for 48 hrs. The crude product was purified by eluting with 2.5% MeOH in CHCl$_3$ ((2) to give the product as a pale yellow foam (163.5 mg, 32.0%).

$^{31}$p NMR: δ4.19, 3.76 (1:1).

$^1$H NMR: δ 7.40 (1H,d,H8), 7.24–7.19 (2H,t,'o'-Ph), 7.12–7.03 (3H,m,'m'+p-Ph), 6.05–5.95 (2H,m,H2'+NHcPr), 5.79 (1H,d,H3'), 5.44 (1H,s,H'), 5.02 (2H,bs,NH$_2$), 4.384.07 (4H,m,H5',NHala+CHala), 3.61 (3H,s,OCH$_3$), 3.54 (3H,d,OCH$_3$), 3.05–2.52 (5H,m,CH$_2$aa,H4',CHcPr,+ 1of H6'), 1.64–1.52 (1'H,m,1of H6'), 0.77–0.73 (2H,t,J=5.49 Hz,2Hof CH$_2$cPr), 0.51 (2H,bs,2Hof CH$_2$CPr).

$^{13}$C NMR: δ173.3 (CO), 172.4 (CO), 161.5 (C2), 157.7 (C4), 152.3 (C8), 152.1 ('ispo'-Ph), 137.8 (C2'), 137.0 (C6), 132.6 (C3'), 131.1 ('m'-Ph), 126.4 ('p'-Ph), 121.6 ('o'-P3), 116.2 (C5), 70.5 (C5'), 60.3 (Cl'), 54.3 (OCH$_3$), 53.5 (OCH$_3$), 52.6 (CHala), 47.1 (C4'), 39.7 (CH$_2$ala), 36.0 (C6'), 25.1 (CHcPr), 8.8 (CH$_2$cPr).

MS ES$^+$: m/z 585.8 (100%, M$^+$), 607.7 (30%, M+Na$^+$.

MS FAB: For C$_{26}$H$_{33}$O$_5$N$_7$P requires 586.217910, found 586.217510.

HPLC: $t_R$ 29.261 (100%)-(100% water (0 mins), 20% water (35 mins), 20% water (45 mins), 100% water (55 mins)).

IR: 3347.5 (N-Hstr.), 2850.7 (C-Hstr.), 1739.9 (C=Ostr.), 1596.1 (aromatic C-Cstr.), 1461.9 (C-Hdef.), 1376.6 (—CH$_3$sym.def.), 1262.4 (P=O), 1211.2 (P-O-aryl), 1158.3 (C-Ostr.), 1027.0 (P-O-alkyl), 935.6 (olefinic C-Hdef), 761.5, 722.0 (monosub.aromatic C-Hdef.).

3-cyclohexyl-L-alanine methyl ester hydrochloride salt

C$_9$H$_{19}$N$_1$O$_2$Cl$_1$, MW=221.75

This was synthesised according to Standard Procedure 1, using 3-cyclohexyl-L-alanine (3.0 g, 17.5 mmol), methanol (30 ml), and thionyl chloride (2.56 ml, 35 mmol). The product was isolated as a white solid (3.23 g, 83.9%).

$^1$H NMR (MeOH-d$_4$): δ4.124.07 (3H,t,CHala), 3.85 (3H,s, OCH$_3$), 1.741.68 (6H,m,CH$_{2+o}$-CH$_2$), 1.56–1.43 (1H,m, CH), 1.36–1.15 (4H,m,m-CH$_2$), 1.05–0.90 (2H,q,p-CH$_2$)

$^{13}$C NMR: δ170.15 (CO), 52.7 (OCH$_3$), 50.8 (CHala), 38.2 (CH$_2$), 33.6 (CH), 33.0+32.7 (2xCH$_2$-o), 26.3 (p-CH$_2$), 26.0+25.9 (2xCH$_2$-m).

Phenyl-(methoxy-3-cyclohexyl-L-alaninyl)-phosphorochloridate

C$_{16}$H$_{23}$N$_1$O$_4$P$_1$Cl$_1$, MW=359.82

This was synthesised according to Standard Procedure 3, using 3-Cyclohexyl-L-alanine methyl ester hydrochloride salt (0.7 g, 316 mmol), PhOP(O)Cl$_2$ (0.47 ml, 3.16 mmol), triethylamine (0.88 ml. 6.31 mmol) in DCM (60 ml). The usual workup yielded the crude product as a yellow oil (1.18 g, 100%), which was stored in THF (7 ml) to give a 0.45M solution.

$^{31}$p NMR: δ9.79, 9.49 (1:1).

$^1$H NMR: δ7.49–7.43 (2H,m,'o'-Ph), 7.37–7.19 (3H,m,'m'+'p'-Ph), 4.464.35 (1H,q,NHala), 4.32–4.20 (1H,m,CHala), 3.88–3.85 (3H,dd,OCH$_3$), 1.94–1.90 (1H,d,CHcHx), 1.76–1.60

(1S,4R)-4-(2-amino-6-cyclopropylamino-9H-purin-9-yl)-2-cyclopentene-1-methanol O-Phenyl-(methoxy-3-cyclohexane-L-alaninyl)-phosphate. Cf1709.
$C_{30}H_{40}N_7O_5P_1$, MW=609.66

This was synthesised according to Standard Procedure 4, using (1S,4R)-4-(2-amino-6-cyclopropylamino-9H-purin-9-yl)-2-cyclopentene-1-methanol (150 mg, 0.52 mmol), tBuMgCl (1.05 ml, 1.05 mmol, of a 1.0M solution in THF), in THF (4 ml) and phenyl-(methoxy-3-cyclohexane-L-alaninyl)-phosphorochloridate (3.5 ml, 1.57 mmol, of a 0.45M solution in THF), at room temperature for 24 hrs. After 24 hrs, additional phenyl-(methoxy-3-cyclohexane-L-alaninyl)-phosphorochloridate (2.5 ml, 1.12 mmol, of a 0.45M solution in THF) was added and the reaction stirred for another 24 hrs. The crude product was purified by eluting with 3% MeOH in $CHCl_3$, and then 2.5% MeOH in $CHCl_3$ to give the pure product as a pale yellow foamy solid (79.6 mg, 24.9%).
31P NMR: δ4.14, 3.98 (1:1).
$^1$H NMR: δ7.50 (1H,d,H8), 7.34–7.13 (5H,t,OPh), 6.20 (1H,s,NHcPr), 6.08 (1H,t,H2'), 5.89 (1H,q,H3'), 5.53 (1H, bs,H1'), 5.16 (2H,bs,$NH_2$), 4.24–3.84 (4H,m,H5',NHala+CHala), 3.66 (3H,s,$OCH_3$), 3.34 (1H,bs,), 3.11 (1H,d, ), 3.03 (1H,bs, ), 2.84–2.72 (1H,m,1of H6'), 1.98–1.36 (8H,m, ), 1.11 (3H,bs, ), 0.89–0.83 (4H,m,2Hof cPr+$4CH_2$-'p'), 0.63 (2H,d,2Hof cPr).
$^{13}$C NMR: δ174.8CO 160.2 (C2), 156.5 (C4), 151.3 (C6), 151.2 ('ipso'-Ph), 136.8 (C2'), 135.9 (C8), 131.5 (C3'), 130.0 ('m'-Ph), 125.2 ('p'-Ph), 120.5 ('o'-Ph), 115.1 (C5), 69.4 (C5'), 59.3 (Cl'), 52.7 (CHala), 46.1 (C4'), 42.5 ($CH_2$), 34.9 (C6'), 33.8 (CHcHx), 32.7 ($CH_2$-'o'), 26.7 ($CH_2$-'m'), 26.4 ($CH_2$-p'), 24.2 (CHcPr), 7.8 ($CH_2$cPr).
MS ES$^+$: m/z 610.3 (40%, M$^+$), 632.3 (100%, M+Na$^+$), 633.3 (25%, M+H+Na$^+$).
MS FAB: For $C_{30}H_{40}O_5N_7NaP$ requires 632.2726, found 632.2727.
HPLC: $t_R$ 42.154 (100%)-(100% water (0 mins), 20% water (35 mins), 20% water (45 mins), 100% water (55 mins)).

(1S,4R)-4-(2-amino-6-cyclopropylamino-9H-purin-9-yl)-2-cyclopentene-1-methanol O-(L-alaninyl)-phosphate diammonium salt Cf1540.
(1S,4R)-4-(2-amino-6-cyclopropylamino-9H-purin-9-yl)-2-cyclopentene-1-methanol O-[phenyl-(methoxy-L-alaninyl)]-phosphate (125 mg, 0.24 mmol) was stirred in $H_2O$: $NEt_3$ (10 ml, 1:1 v/v), at 25–35° C. for 5 hrs. The reaction mixture was extracted with DCM (8×20 ml), and the aqueous layer reduced to dryness. The resulting solid was solubilised in isopropanol and purified by flash column chromatography, gradient eluting with i-PrOH:$H_2O$: $NH_3$ (11:1:1 to 9:1:2). The appropriate fractions were reduced to dryness and freeze dried to give the pure product as a white foamy solid (106 mg, 95%).
$^{31}$P NMR ($D_2O$): δ8.62 (s).
$^1$H N $D_2O$:-δ7.79 (1H,s,H8), 6.08 (1H,d,H12'), 5.77 (1H, dH3'), 5.35 (1H,t,HI'), 3.71–3.58 (2H,m,H5'), 3.41–3.32 (1H,m,CHa.a), 3.02–2.94 (1H,m,NHCH), 2.70–2.59 (2H,m, H4'+1 of $CH_2$), 1.57–1.49 (1H,dt,l of $CH_2$), 1.10 (3H,d, $CH_3$), 0.83–0.76 (2H,q,1 of $CH_2$cyclo.), 0.61–0.56 (2H,q, 1 of $CH_2$cyclo.).
MS ES$^+$: m/z 437.9 (100%, M$^+$).
MS FAB: calculated m/z 438.165481, found m/z 438.163790.
(1S,4R)-4-(2-amino-6-cyclopropylamino-9H-purin-9-yl)-2-cyclopentene-1-methanol O-(D-alaninyl)-phosphate diammonium salt.

(1S,4R)-4-(2-amino-6-cyclopropylamino-9H-purin-9-yl)-2-cyclopentene-1-methanol O-[phenyl-(methoxy-D-alaninyl)]-phosphate (100 mg, 0.19 mmol) was stirred in $H_2O$: $NEt_3$ (8 ml, 1:1 v/v), for l 6 hrs. The reaction mixture was extracted with DCM (5×20 ml), and the aqueous layer reduced to dryness. The resulting solid was solubilised in isopropanol and purified by flash column chromatography, gradient eluting with i-PrOH:$H_2O$:$NH_3$ (11:1:1 to 9:1:2). The appropriate fractions were reduced to dryness and freeze dried to give the pure product as a white foamy solid (88%).
$^{31}$p NMR (MeOH):-δ7.81 (s).
$^1$H NMR:-δ7.74 (1H,s,H8), 6.12 (1H,d,J=5.53 Hz,H2'), 5.78 (1H,t,H3'), 5.44 (1H,d,J=6.21 Hz,H1'), 3.74 (2H,t,J=5.42 Hz,H5'), 3.70–3.60 (1H,m,CHala), 3.01 (1H,bs,H4'), 2.84 (1H,d,J=3.28 Hz,CHcPr), 2.73–2.63 (1H,dt,J=8.66 Hz+5.17 Hz,1of H6'), 1.67–1.58 (1H,m,l of $CH_2$), 1.21 (3H,d,J=7.01 Hz,$CH_3$ala), 0.79–0.73 (2H,q,J=6.68 Hz,2H of $CH_2$cPr), 0.53 (2H,t,2H of $CH_2$cPr).
$^{13}$C NMR: δ179.8 (CO), 161.2 (C2), 157.1 (C4), 151.1 (C6), 139.5 (C2'), 137.8 (C8), 130.7 (C3'), 114.6 (CS), 68.0 (C5'), 60.5 (Cl'), 51.9 (CHala), 47.6 (C4'), 35.9 (C6'), 24.4 (CHcPr), 21.7 ($CH_3$ala), 7.6 ($CH_2$cPr).
MS ES$^+$: m/z 437.9 (100%, M$^+$).
MS FAB: calculated m/z 438.165481, found m/z 438.167842.
Phenyl-(ethoxy-L-alaninyl)-phosphorochloridate.
$C_{11}H_{15}O_4N_1Cl_1P_1$, MW=291.67.

This was synthesised according to Standard Procedure 3, using L-Alanine ethyl ester hydrochloride (1.0 g, 6.51 mmol), PhOP(O)$Cl_2$ (1.37 g, 0.97 ml, 6.51 mmol) and $NEt_3$ (1.32 g, 1.81 ml, 13.0 mmol) to yield 1.85 g (97.4%) of crude product as an oil that was stored in anhydrous THF (10 ml), to give a 0.63 mmol/ml solution that was used without further purification.
$^{31}$P NMR: δ9.41, 9.16 (1:1).
$^1$H NMR: δ7.42–7.35 (2H,dd, 'o'-Ph), 7.31–7.25 (3H,m, 'm'+'p'-Ph), 4.71 (1H,d,NHala), 4.314.13 (3H,m,$OCH_2$+CHala), 1.55–1.52 (3H,dd,OCH $CH_3$), 1.33–1.30 (3H,dd, $CH_3$ala).
$^{13}$C NMR: δ173.1 (CO), 150.2 ('ipso'-Ph), 130.3 ('m'-Ph), 126.4 ('p'-Ph), 120.9 ('o'-Ph), 62.3 ($OCH_2$), 51.0 (CHala), 20.9 ($CH_2CH_3$), 14.5 ($CH_3$ala).
(1S,4R)-4-(2-amino-6cyclopropylamino-9H-purin-9-yl)-2-cyclopentene-1-methaanol O-[phenyl-(ethoxy-L-alaninyl)]-phosphate. Cf1587.
$C_{24}H_{30}O_5N_7P_1$, MW=527.53.

This was synthesised according to Standard Procedure 4, using (1S,4R)-42-amino-6-cyclopropylamino-9H-purin-9-yl)-2-cyclopentene-1-methanol (300 mg, 1.4 mmol), tBuMgCl (1.0M solution in THF) (1.57 ml, 1.57 mmol), and phenyl-(ethoxy-L-alaninyl) phosphorochloridate (0.49M solution in THF) (6.45 ml, 3.14mmol) in anhydrous THF (20 ml), and stirring at room temperature for 24 hrs. The crude product was purified by column chromatography eluting with 2.5% MeOH in $CHCl_3$ to give the product as a pale yellow foam (290 mg, 51.1%).
$^{31}$p NMR: δ4.04, 3.96 (1:1).
$^1$H N: δ7.39 (1H,d,J=7.56 Hz,H8), 7.23–7.18 (2H,t,J=7.90 Hz,'o'-Ph), 7.12–7.10 (2H,t,'m'-Ph), 7.06–7.01 (1H,t,J= 7.13 Hz,'p'-Ph), 6.18 (1H,bs,NHcPr), 5.97–5.95 (1H,tH2'), 5.79–5.75 (1H,t,J=5.55 Hz,H3'), 5.43 (1H,s,H1'), 5.13 (2H, bs,$NH_2$), 4.30–4.14 (1H,m,NHala), 4.064.00 (4H,m,H5'+$OCH_2$), 3.96–3.84 (1H,m,CHala), 3.03 (1H,d,J=5.74 Hz,H4'), 2.92 (1H,bs,CHcPr), 2.71–2.61 (1H,m,1of H6'), 1.60–1.51 (1H,m, 1of H6'), 1.29–1.24 (3H,tJ=6.64 Hz,$CH_3$ala), 1.18–1.11 (3H,m,$CH_2\underline{CH_3}$), 0.75–0.71 (2H,q, J=6.76 Hz,2H of $CH_2$cPr), 0.50 (2H,bs,2H of $CH_2$cPr).
$^{13}$C NMR: δ173.35 (CO), 159.8 (C2), 156.0 (C4), 150.6 (C6) 150.4('ipso'-Ph), 136.1 (C2'), 135.1 (C8), 130.8 (C3'), 129.3 ('m'-Ph), 124.5 ('p'-Ph), 119.8 ('o'-Ph), 114.4 (C5), 68.6 (C5'), 61.2 (OCH$_2$), 58.5 (Cl'), 50.0 (CHala), 45.3 (C4'), 34.3 (C6'), 23.4 (CcPr), 20.6 (CH$_3$ala), 13.8 (CH$_2$CH$_3$), 7.0 (CH$_2$cPr).
MS ES$^+$: m/z 541.9 (100%, M$^+$), 546.84 (28%, M+H$^+$), 563.8 (25%, M+Na$^+$).
MS FAB: For C$_{25}$H$_{33}$O$_5$N$_7$P, requires 542.228081, found 542.228131.
HPLC: t$_R$ 31.76, 32.03 (100%)-(100% water (0 mins), 20% water (35 mins), 20% water (45 mins), 100% water (55 mins)).
IR: 3334.1 (N-Hstr.), 1734.5 (C=Ostr.), 1595.9, 1488.0 (aromatic C-Cstr.), 1450.3 (C-Hdef.), 1394.2 (-CH$_3$sym.def.), 1252.8 (P=O), 1210.4 (P-O-aryl), 1153.3 (C-Ostr.), 1026.0 (P-O-alkyl), 934.8 (olefinic C-Hdef.), 759.0 (monosub.aromatic C-Hdef.).
Phenyl-(benzoxy-L-alaninyl)-phosphorochloridate.
C$_{16}$H$_{17}$O$_4$N$_1$Cl$_1$P$_1$, MW=353.74.
This was synthesised according to Standard Procedure 3, using L-alanine benzyl ester hydrochloride (1.0 g, 4.64 mmol), PhOP(O)Cl$_2$ (0.98 g, 0.69 ml, 4.64 mmol) and NEt$_3$ (0.94 g, 1.29 ml, 9.27 mmol) to yield 1.61 g (98.2%) of crude product that was stored in anhydrous THF (10ml), to give a 0.46 mmol/ml solution that was used without further purification.
$^{31}$p NMR: δ9.41, 9.23 (1:1).
$^1$H NMR: δ7.41–7.21 (10H,m,2xPh), 5.24 (2H,d,CH$_2$Ph), 4.95–4.88 (1H,t,NHala), 4.36–4.15 (1H,m,CHala), 1.56 (3H,t,CH$_3$ala).
$^{13}$C NMR: δ172.9 (CO), 150.2 ('ipso'-OPh), 135.5 ('ipso'-CH$_2$Ph), 130.3 ('m'-OPh), 129.0 ('o'-CH$_2$Ph), 128.7 ('m'+ 'p'-CH$_2$Ph), 126.4 ('p'-OPh), 121.0 ('o'-OPh), 68.0 (OCH$_2$), 51.1 (CHala), 20.8 (CH$_3$ala).
(1S,4R)-4-(2-amino-6-cyclopropylamino-9H-purin-9-yl)-2-cyclopentene-1-methanol O-[phenyl-(enzoxy-L-alaninyl)]-phosphate. Cf1582.
C$_{30}$H$_{35}$O$_5$N$_7$P$_1$, MW=603.6.
This was synthesised according to Standard Procedure 4, using (1S,4R)-4-(2-amino-6-cyclopropylamino-9H-purin-9-yl)-2-cyclopentene-1-methanol (400 mg, 1.44 mmol), tBuMgCl (1.0M solution in THF) (2.1 ml, 2.1 mmol), and phenyl-(benzoxy-L-alaninyl)-phosphorochloridate (0.46M solution in THF) (9.2 ml, 4.19 mmol) in anhydrous THF (20 ml), and stirring at room temperature for 64 hrs. The crude product was purified by column chromatography eluting with 3% MeOH in CHCl$_3$, and then 2.5% MeOH in CHCl$_3$ to give the product as a white foam (82.2 mg, 9.75%).
A second synthesis was undertaken with (1S,$^4$R)-$^4$-(2-amino-6-cyclopropylamino-9H-purin-9-yl)-2-cyclopentene-1-methanol (200 mg, 0.7 mmol), tBuMgCl (2.43 ml of a 1.0M soln in THF, 2.43 mmol), and phenyl-(benzoxy-L-alaninyl)-phosphorochloridate (2.2 ml of a 0.46M soln in THF, 2.1 mmol) in THF (2.5 ml). Purification by column chromatography eluting with 3% MeOH in CHCl$_3$ gave the pure product as a white foamy solid (90 mg, 21.3%).
$^{31}$P NMR: 8 3.82, 3.72 (1:1). $^1$H NMR: δ7.51 (1H,d,H8), 7.37–7.15 (IOH,m,OPh+CH$_2$Eh), 6.10–6.04 (1H,m,H2'), 5.96 *(H,bs,NHcPr), 5.89 (1H,dd,J=5.36 HzH3'), 5.54 (1H, t,H1'), 5.16 (2H,bs,NH$_2$), 4.96 (2H,bs,CH Ph), 4.234.05 (3H,m,NHala+H5'), 3.89–3.70 (1H,dt,CHala), 3.16–3.12 (1H,t,H4'), 3.03 (1H,bs,CHcPr), 2.85–2.71 (1H,m,1of H6'), 1.74–1.64 (1H,m,1of H6'), 1.44–1.39 (3H,t,J=7.84 Hz,CH$_3$ala), 0.88 (2H,q,J=6.75 Hz,2H of CH$_2$cPr), 0.64 (2H,m,2H of CH$_2$cPr).
13C NMR: δ173.3 (CO), 159.7 (C2), 156.0 (C4), 150.9 (C6), 150.7 ('ipso'-OPh), 136.4 (C2'), 135.7 ('ipso'-Bn), 135.2 (CS), 131.0 (C3'), 129.6 ('o'-Bn), 128.6 ('m'-Bn), 128.5 ('p'-Bn), 128.2 ('m'-OPh), 124.9 ('p'-OPh), 120.1 ('o'-OPh), 114.8 (C5), 68.8 (C5'), 67.2 CH$_2$Ph), 58.9 (Cl'), 50.3 (CHala), 45.6 (C4'), 34.4 (C6'), 23.7 (CHcPr), 21.0 (CH$_3$ala), 7.4 (CH$_2$cPr).
MS ED$^+$: m/z 603.8 (100%, M$^+$), 604.8 (30%, M+H$^+$), 625.7 (20%, M+Na$^+$).
MS FAB: For C$_{30}$H$_{35}$O$_5$N$_7$P requires 604.243731, found 604.241775.
HPLC: tR 33.39 (99.7%)-(100% water (0 mins), 20% water (35 mins), 20% water (45 mins), 100% water (55 mins)).
IR: 3355.9 (N-Hstr.), 2923.3, 2853.7 (C-Hstr.), 1734.1 (C=Ostr.), 1595.6 (aromatic C-Cstr.), 1458.4 (C-Hdef.), 1376.5 (-CH$_3$sym.def.), 1154.4 (C-Ostr.), 1028.2 (P-O-alkyl), 935.8 (olefinic C-Hdef.), 721.7 (monosub.aromatic C-Hdef).
L-Alanine n-propyl ester hydrochloride salt.
C$_6$H$_{14}$N$_1$O$_2$Cl$_1$, MW=167.634
This was synthesised according to Standard Procedure 1, using anhydrous propan-1-ol (42.0 ml, 0.56 mol), thionyl chloride (8.2 ml, 0.112 mol) and L-alanine (5.0 g, 0.056 mol). The product was isolated as a white solid (8.88 g, 94.3%).
$^1$H NMR (MeOH-d$_4$): δ4.344.26 (2H,m,OCH$_2$), 4.244.17 (1H,q,CHala), 1.88–1.78 (2H,m,CH$_2$), 1.65 (3H,d,J=7.24 Hz,CH$_3$ala), 1.10–1.05 (3H,t,CH$_2$CH$_3$). $^{13}$C NMR: δ170.1 (CO), 68.0 (OCH$_2$), 48.9 (CHala), 21.9 (CH$_2$), 15.3 (CH$_3$ala), 9.5 (CH$_2$CH$_3$)
Phenyl-(n-propoxy-L-alaninyl)-phosphorochloridate
C$_{12}$H$_{17}$N$_1$O$_4$P$_1$Cl$_1$, MW=305.79
This was synthesised according to Standard Procedure 3, using L-Alanine n-propyl ester hydrochloride salt (0.5 g, 2.98 mmol), PhOP(O)Cl$_2$ (0.45 ml, 2.98 mmol), triethylamine (0.83 ml. 5.97 mmol) in DCM (70 ml). The usual workup yielded the crude product as a yellow oil (0.84 g, 92.1%), which was stored in THF (5 ml) to give a 0.55M solution.
$^{31}$P NMR: δ9.41, 9.17 (1:1).
$^{13}$C NMR: δ173.1 (CO), 150.1 ('ipso'-Ph), 130.0 ('m'-Ph), 126.4 ('p'-Ph), 121.0 ('o'-Ph), 67.9 (OCH$_2$), 51.0 (CHala), 22.3 (CH$_2$CH$_3$), 21.0 (CH$_3$ala), 10.7 (CH$_2$CH$_3$).
(1S,4R)-4-(2-amino-6-cyclopropylamino-9H-purin-9-Sl)-2-cyclopentene-1-methanol O-Phenyl-(n-propoxy-L-alaninyl)-phosphate. Cf1646.
C$_{26}$H$_{34}$N$_7$O$_5$P, MW=555.57
This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (3 ml) and phenyl-(n-propyl-L-alaninyl)-phosphorochloridate (1.9 ml, 1.05 mmol, of a 0.55M solution in THF), at room temperature for 24 hrs. The crude product was purified by eluting with 3% MeOH in CHCl$_3$ to give the pure product as a pale yellow foamy solid (123 mg, 63.4%).
$^{31}$P NMR: δ4.06, 3.98 (1:1).
$^1$H NMR: δ7.40 (1H,d,J=7.99 HzH8), 7.23–7.18 (2H,dd,'o'-Ph), 7.12–7.02 (3H,m,'m'+'p'-Ph), 6.16 (1H,bs,H3'), 5.96 (1H,tH2'), 5.78 (1H,d,J-5.83 Hz,NHcycl), 5.44 (1H,bs,H1'), 5.15 (2H,bs,NH$_2$), 4.33–4.18 (1H,m,CHala), 4.15–4.04 (2H, m,OCH$_2$), 4.01–3.88 (2H,m,H5'), 3.65 (1H,bs,NHala), 3.03 (1H,d,H4'), 2.92 (1H,bs,CHcycl), 2.72–2.62 (1H,m,1of H6'), 1.60–1.47 (3H,m,1of H6'+CH$_2$CH$_3$), 1.30–1.26 (3H,t, CH$_3$ala), 0.84–0.80 (3H,m,CHCH:), 0.73 (2H,d,J=6.8 Hz,1of CH$_2$cycl), 0.51 (2H,bs,1 of CH$_2$cycl).
$^{13}$C NMR: δ174.ICO 160.4 (C2), 156.6 (C4), 151.1 (C6+ 'ipso'-Ph), 136.8 (C2'), 135.9 (C8), 131.5 (C3'), 130.0 ('m'-Ph), 125.2 ('p'-Ph), 120.5 ('o'-Ph), 115.0 (C5), 69.2

(C5'), 67.4 (OCH$_2$), 59.2 (Cl'), 50.6 (CHala), 46.0 (C4'), 35.0 (C6'), 24.2 (CHcPr), 22.3 (CH$_2$CH$_3$), 21.5 (CH$_3$ala), 10.7 (CH$_2$CH$_3$), 7.7 (CH$_2$cycl).

MS ED$^+$: m/z 555.8 (100%, M$^+$), 557.0 (30%, M+H$^+$).

MS FAB: For C$_{26}$H$_{35}$O$_5$N$_7$P requires 556.2437, found 556.2438.

HBLC: t$_R$ 34.708 (100%)-(100% water (0 mins), 20% water (35 mins), 20% water (45 mins), 100% water (55 mins)).

L-Alanine n-butyl ester hydrochloride salt.

C$_7$H$_{16}$N$_1$O$_2$Cl$_1$, MW=181.661

This was synthesised according to Standard Procedure 1, using anhydrous butan-1-ol (51.4 ml, 0.56 mol), thionyl chloride (8.2 ml, 0.1 12 mol) and L-alanine (5.0 g, 0.056 mol). The product was isolated as a white solid (8.86 g, 86.9%).

$^1$H NMR (MeOH-d$_4$): δ4.29–4.17 (2H,m,OCH$_2$), 4.13–4.06 (1H,q,CHala), 1.71–1.62 (2H,m,OCH$_2$CH$_2$), 1.53 (3H,d,J= 7.25 Hz,CH$_3$ala), 1.47–1.34 (2H,m,CH$_2$CH$_3$), 0.96–0.91 (3H,t,CH CH).

$^{13}$C NMR: δ170.1 (CO), 66.2 (OCH$_2$), 48.9 (CHala), 30.6 (OCH$_2$CH$_2$), 19.0 (CH$_2$CH$_3$), 15.3 (CH$_3$ala), 13.0 (CH$_2$CH$_2$).

Phenyl-(n-butoxy-L-alaninyl)-phosphorochloridate

C$_{13}$H$_{19}$N$_1$O$_4$P$_1$Cl$_1$, MW=337.82

This was synthesised according to Standard Procedure 3, using L-Alanine n-butyl ester 15 hydrochloride salt (0.5 g, 2.75 mmol), PhOP(O)Cl$_2$ (0.41 ml, 2.75 mmol), triethylamine (0.77 ml.5.5 mmol) in DCM (80 ml). The usual workup yielded the crude product as a yellow oil (0.84 g, 94.5%), which was stored in THF (5 ml) to give a 0.525M solution.

$^{31}$P NMR: δ9.39, 9.10 (1:1).

$^1$H NMR: δ7.43–7.15 (5H,m,Ph), 4.68–4.59 (1H,q,CHala), 4.27–4.05 (3H,m,OCH$_2$+NHala), 1.73–1.59 (2H,m,OCH$_2$CH$_2$), 1.56–1.53 (2H,dd,CH$_2$CH$_3$), 1.46–1.37 (3H,m, CH$_3$ala), 1.00–0.92 (3H,m,CH$_2$CH$_3$).

$^{13}$C NMR: δ173.2 (CO), 150.1 ('ipso'-Ph), 130.3 ('m'-Ph), 126.4 ('p'-Ph), 121.0 ('o'-Ph), 66.2 (OCH$_2$), 51.0 (CHala), 30.9 (OCH$_2$CH7), 21.0 (CH$_3$ala), 19.4 (CH$_2$CH$_3$), 14.1 (CH$_2$CH$_3$).

(1S,4R)-4-(2-amino-6-cyclopropylamino-9H-purin-9-yl)-2-cyclopentene-1-methanol O-Phenyl-(n-butoxy-L-alaninyl)-phosphate. Cf1647.

C$_{27}$H$_{36}$N$_7$O$_5$P$_1$, MW=569.597

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (3 ml) and phenyl-(n-butyl-L-alaninyl)-phosphorochloridate (2.0 ml, 1.05 mmol, of a 0.525M solution in THF), at room temperature for 24 hrs. The crude product was purified by eluting with 3% MeOH in CHCl$_3$ to give the pure product as a pale yellow foamy solid (157 mg, 78.9%).

$^{31}$P NMR: δ4.01, 3.95 (1:1).

$^1$H NMR: δ7.40 (1H,d,J=7.32 Hz,H8), 7.23–7.18 (2H,t,'o'-Ph), 7.11 (2H,t,'m'-Ph), 7.04 (1H,t,'p'-Ph), 6.02 (1H,bs, H3'), 5.97 (1H,t,H2'), 5.78 (1H,bs,NHcycl), 5.44 (1H,bs, H1'), 5.06 (2H,bS,NH$_2$), 4.22–3.88 (6H,m,CHala,OCH$_2$, H5'+NHala), 3.05 (1H,d,H4'), 2.93 (1H,bs,CHcycl), 2.72–2.62 (1H,m,1of H6'), 1.61–1.47 (3H,m,1of H6'+ OCH$_7$CH ), 1.30–1.26 (5H,t,CH$_3$ala+CH$_2$CH$_3$), 0.85–0.80 (3H,t,CH CH), 0.74 (2H,d,J=6.45 Hz,1of CH$_2$cycl), 0.51 (2H,bs,1of CH$_2$cycl).

$^{13}$C NMR: δ174.1(CO), 160.4 (C2), 156.7 (C4), 151.2 (C6), 151.1 ('ipso'-Ph), 136.7 (C2'), 135.8 (C8), 131.5 (C3'), 130.0 ('m'-Ph), 125.2 ('p'-Ph), 120.5 ('o'-Ph), 115.0 (C5), 69.3 (C5'), 65.8 (OCH$_2$), 59.2 (Cl'), 50.6 (CHala), 46.0 (C4'), 35.0 (C6'), 30.9 (OCH$_2$CH$_2$), 24.1 (CHcPr), 21.5 (CH$_3$ala), 19.4 (CH$_2$CH$_3$), 14.1 (CH$_2$CH$_3$), 7.8 (CH$_2$Cycl).

MS ES$^+$: m/z 569.9 (70%, M$^+$), 570.9 (20%, M+H$^+$), 591.8 (100%, M+Na$^+$), 607.8 (20%, M+K$^+$).

HPLC: tR 388.27 (100%)-(100% water (0 mins), 20% water (35 mins), 20% water (45 mins), 100% water (55 mins)).

L-Alanine i-propyl ester bydrochloride salt.

C$_6$H$_{14}$N$_1$O$_2$Cl$_1$, MW=167.634

This was synthesised according to Standard Procedure 1, using anhydrous propan-2-ol (43.0 ml, 0.56 mol), thionyl chloride (8.2 ml, 0.1 12 mol) and L-alanine (5.0 g, 0.056 mol). The product was isolated as a semicrystalline solid (8.86 g, 86.9).

$^1$H NMR (MeOH-d$_4$): δ5.16–5.08 (1H,m,CHala), 4.11–4.04 (1H,q,OCH(Me)$_2$), 1.55 (3H,d,J-7.2 1 Hz,CH$_3$ala), 1.34–1.31 (6H,dd,CH(Me)$_2$). $^{13}$C NMR: 6 169.5 (CO), 70.8 (COCH(Me)$_2$), 48.9 (CHala), 20.8 (CH$_3$ala), 15.3 (CH( Me)$_2$).

Phenyl-(i-propoxy-L-alaninyl)-phosphorochloridate

C$_{12}$H$_{17}$N$_1$O$_4$P$_1$Cl$_1$, Mw=305.79

This was synthesised according to Standard Procedure 3, using L-Alanine i-propyl ester hydrochloride salt (0.5 g, 2.98 mmol), PhOP(O)Cl$_2$ (0.45 ml, 2.98 mmol), triethylamine (0.83 ml. 5.97 mmol) in DCM (70 ml). The usual workup yielded the crude product as a yellow oil (1.12 g, >100%), which was stored in THF (5 ml) to give a 0.597M solution.

$^{31}$P NMR: δ9.45, 9.17 (1:1).

$^{13}$C NMR: δ172.6 (CO), 150.2 ('ipso'-Ph), 130.3 ('m'-Ph), 126.4 ('p'-Ph), 121.0 ('o'-Ph), 70.1 (OCH), 51.1 (CHala), 22.1 (CH(CH$_3$)$_2$), 20.9 (CH$_3$ala).

(1S,4R)-4-(2-amino-6-cyclopropylamino-9H-purin-9-yl)-2-cyclopentene-1-methanol O-Phenyl-(i-propoxy-L-alaninyl)-phosphate Cf1661.

C$_{26}$H$_{34}$N$_7$O$_5$P$_1$, MW=555.57

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (3 ml) and phenyl-(i-propyl-L-alaninyl)-phosphorochloridate (1.76 ml, 1.05 mmol, of a 0.597M solution in THF), at room temperature for 72 hrs. The crude product was purified by eluting with 3% MeOH in CHCl$_3$ (x2) to give the pure product as a pale yellow foamy solid (106.8 mg, 54.8%).

$^{31}$P NMR: δ4.02, 3.98 (1:1).

$^1$H NMR: δ7.41 (1H,d,J=8.12 Hz,H8), 7.24–7.19 (2H,m,'o'-Ph), 7.13–7.03 (3H,m,'m'+'p'-Ph), 6.37 (1H,bs,CHcPr), 5.98 (1H,t,H3'), 5.80–5.76 (1H,m,H2'), 5.43 (H,bs,H1'), 5.21 (2H,bs,NH$_2$), 4.944.86 (1H,m,OCH), 4.15–3.98 (2H, m,H5'), 3.92–3.83 (1H,m,CHala), 3.59 (1H,bs,NHala), 3.06–2.98 (1H,m,H4'), 2.93 (1H,bs,CHCPr), 2.74–2.63 (1H, m,1of H6'), 1.62–1.53 (1H,m,1of H6'), 1.34–1.18 (3H,m, CH$_3$ala), 1.15–1.11 (6H,m,CH(CH$_3$)$_2$), 0.79–0.73 (2H,q, 2Hof CH$_2$cPr), 0.53 (2H,bs,2Hof CH$_2$cPr).

$^{13}$C NMR: δ173.5(CO) 159.8 (C2), 156.2 (C4), 151.1 (C6), 151.0 ('ipso'-Ph), 136.9 (C2'), 136.1 (C8), 131.3 (C3'), 130.0 ('m'-Ph), 125.3 ('p'-Ph), 120.5 ('o'-Ph), 115.0 (C5), 69.6 (C5'), 69.2 (OCH), 59.3 (Cl'), 50.7 (CHala), 46.0 (C4'), 34.9 (C6'), 24.2 (CHcPr), 22.0 (CH(CH$_3$)$_2$)2), 21.4 (CH$_3$ala), 7.8 (CH$_2$cycl).

□S ES$^+$: m/z 555.9 (100%, M$^+$), 556.9 (30%, M+H$^+$).

MS MALD/I TOF: For C$_{26}$H$_{35}$O$_5$N$_7$P found 555.575.

HPLC: $t_R$ 35–85 (100%)-(100% water (0 mins), 20% water (35 mins), 20% water (45 mins), 100% water (55 mins)).
Phenyl-tertbutyloxy-L-alaninyl phosphorochloridate.
$C_{16}H_{17}O_4N_1Cl_1P_1$, MW=353.74.

This was synthesised according to Standard Procedure 3, using L-alanine tert-butyl ester hydrochloride (0.5 g, 2.75 mmol), PhOP(O)Cl$_2$ (0.41 ml, 2.75 mmol) and NEt$_3$ (0.77 ml, 5.5 mmol) to yield 0.77 g (87.5%) of crude product that was stored in anhydrous THF (5 ml), to give a 0.48 mmol/ml solution that was used without further purification.
$^{31}$P NMR: δ9.53, 9.20 (1:1).
$^1$H NMR: δ7.44–7.39 (2H,t,'o'-Ph), 7.32–7.26 (3H,m,'m'+'p'-Ph), 4.4714.34 (1H,m,NHala), 4.17–4.04 (1H,m,CHala), 1.53 (9H,3s,3xCH$_3$).
$^{13}$C NMR: δ170.7 (CO), 148.7 ('ipso'-Ph), 128.9 ('o'-Ph), 124.9 ('p'-Ph), 119.5 ('m'-Ph), 81.65 (CMe$_3$), 50.0 (CHala), 26.9 (3xCH$_3$).
(1S,4R)-4-(2-amino-6-cyclopropylamino-9H-purin-9-yl)-2-cyclopentene-1-methanol O-(phenyl-tertbutyloxy-L-alaninyl)-phosphate. Cf1645.
$C_{24}H_{30}O_5N_7P_1$, MW=603.6.

This was synthesised according to Standard Procedure 4, using (1S,4R)-4-(2-amino-6-cyclopropylamino-9H-purin-9-yl)-2-cyclopentene-1-methanol (140 mg, 0.52 mmol), tBuMgCl (1.05 ml, 1.05 mmol of a 1.0M solution in THF), and phenyl-(tertbutyloxy-L-alaninyl)-phosphorochloridate (3.3 ml, 1.57 mmol, of a 0.48M solution in THF), in anhydrous THF (4 ml) stirring at room temperature for 48 hrs. The crude product was purified by eluting with 3% MeOH in CHCl$_3$ to give the pure product as white foamy solid (192.3 mg, 69.0%).
$^{31}$P NMR: δ4.15 (s).
$^1$H NMR: δ7.40 (1H,d,J=8.35 Hz,H8), 7.23–7.18 (2H,t,'m'-Ph), 7.12 (2H,d,'o'-Ph), 7.06–7.02 (1H,t,'p'-Ph), 6.09 (1H, bs,H2'), 5.97 (1H,bs,H3'), 5.77 (1H,d,NHcPr), 5.44 (1H,bs, HI'), 5.10 (2H,bs,NH$_2$), 4.144.05 (3H,m,H5'+NHala), 3.85–3.77 (1H,q,CHala), 3.04 (1H,bs,H4'), 2.93 (1H,bs, CHcPr), 2.72–2.62 (1H,m,1of H6'), 1.58–1.53 (1H,t,1of H6'), 1.34 (9H,d,CMe$_3$), 1.27–1.23 (3H,t,CH$_3$ala), 0.73 (2H, d,2Hof CH$_2$cPr), 0.51 (2H,bs,2Hof CH$_2$cPr).
$^{13}$C NMR: δ173.2 (CO), 160.4 (C2), 156.7 (C4), 151.2 (C6+'ipso'-Ph), 136.8 (C2'), 135.9 (C8), 131.5 (C3'), 130.0 ('m'-Ph), 125.2 ('p'-Ph), 120.6 ('o'-Ph), 115.2 (C5), 82.3 (C[H$_3$]$_3$), 69.3 (C5'), 59.1 (Cl'), 46.0 (C4'), 35.0 (C6'), 28.3 (3xCH$_3$), 24.2 (CHCPr), 1.5 (CH$_3$ala), 7.8 (CH$_2$cPr).
S ES$^+$: m/z 570.0 (100%, M$^+$), 570.9 (32%, M+H$^+$).
MS FAB: For $C_{27}H_{37}O_5N_7P$ requires 570.2594, found 570.2598.
HPLC: $t_R$ 36.158 (100%)-(100% water (0 mins), 20% water (35 mins), 20% water (45 mins), 100% water (55 mins)).
L-Alanine n-pentyl ester hydrochloride salt
$C_8H_{16}N_1O_2Cl_1$, MW=195.69

This was synthesised according to Standard Procedure 1, using pentanol (36.3 ml, 0.337 mol), thionyl chloride (4.92 ml, 67.4 mmol) and L-Alanine (3.0 g, 33.7 mmol). The product was isolated as a white solid pure product (4.86 g, 73.7%).
$^1$H NMR (MeOH-d$_4$): δ4.324.20 (2H,m,OCH$_2$), 4.16–4.08 (1H,m,CHala), 1.77–1.68 (2H,m,OCH$_2$CH$_2$), 1.56 (3H,d,J=7.22 Hz,CH$_3$ala), 1.42–1.36 (4H,m,CH$_2$CH$_2$CH$_3$), 0.97–0.93 (3H,m,CH$_2$CH$_3$).
$^{13}$C NMR: δ170.1 (CO), 66.5 (OCH$_2$), 48.8 (CHala), 28.2 (OCH$_2$CH$_2$), 28.0 (CH$_2$CH$_2$CH$_3$), 22.3 (CH$_2$CH$_3$), 15.2 (CH$_3$ala), 13.3 (CH$_2$CH$_3$).
Phenyl-(n-pentoxy-L-alaninyl)-phosphorochloridate
$C_{14}H_{21}N_1O_4P_1Cl_1$, MW=333.78

This was synthesised according to Standard Procedure 3, using L-Alanine n-pentyl ester hydrochloride salt (0.5 g, 2.56 mmol), PhOP(O)Cl$_2$ (0.38 ml, 2.56 mmol), triethylamine (0.71 ml. 5.11 mmol) in DCM (60 ml). The usual workup yielded the crude product as a yellow oil (0.79 g, 92.6%), which was stored in THF (5 ml) to give a 0.47M solution.
$^{31}$P NMR: δ9.39, 9.12 (1:1).
$^1$H NMR: δ7.43–7.38 (2H,m,'o'-Ph), 7.32–7.25 (3H,m,'m'+'p'-Ph), 4.63 (1H,bd,NHala), 4.244.11 (3H,m,OCH$_2$+CHala), 1.73–1.65 (2H,m,OCH$_2$CH$_2$), 1.57–1.53 (3H,dd, CH$_3$ala), 1.42–1.35 (4H,m,2xCH$_2$), 0.97–0.91 (3H,m,CH$_2$CH$_3$).
$^{13}$C NMR: δ173.1 (CO), 150.1 ('ipso'-Ph), 130.3 ('m'-Ph), 126.4 ('p'-Ph), 121.0 ('o'-Ph), 66.5 (OCH$_2$), 51.0 (CHala), 28.6 (CH$_2$-C2), 28.3 (CH$_2$-C3), 22.7 (CH$_2$-C4), 21.0 (CH$_3$ala), 14.1 (CH$_3$-C5).
(1S,4R)-4-(2-amino-6-cyclopropylamino-9H-purin-9-yl)-2-cyclopentene-1-methanol O-Phenyl-(n-pentyloxy-L-alaninyl)-phosphate. Cf1706.
$C_{28}H_{38}N_7O_5P_1$, MW=583.7

This was synthesised according to Standard Procedure 4, using (1S,4R)-4-(2-amino-6-cyclopropylamino-9H-purin-9-yl)-2-cyclopentene-1-methanol (10 mg, 0.35 mmol), tBuMgCl (0.7 ml, 0.7 mmol, of a 10M solution in THF), in THF (3 ml) and phenyl-n-pentyl-L-alaninyl)-phosphorochloridate (2.22 ml, 1.05 mmol, of a 0.47M solution in THF), at room temperature for 24 hrs. The crude product was purified by eluting with 2.5–3.0% MeOH in CHCl$_3$ (x2) to give the pure product as a pale yellow foamy solid (143.2 mg, 70.2%).
$^{31}$P NMR: δ3.99, 3.95 (1:1).
$^1$H NMR: δ7.41 (1H,d,J=7.18 Hz,H8), 7.24–7.19 (2H,m,'o'-Ph), 7.12–7.02 (3H,m,'m'+'p'-Ph), 6.09 (1H,bs,NHcPr), 5.98 (1H,d,H2'), 5.79 (1H,bs,H3'), 5.44 (1H,bs,H1'), 5.09 (2H,bs,NH$_2$), 4.16–3.88 (6H,m,CHala,OCH$_2$,H5'+NHala), 3.05 (1H,bs,H4'), 2.94 (1H,bs,CHcPr), 2.73–2.63 (1H,m,1of H6'), 1.62–1.51 (3H,m,1of H6'+OCH$_2$CH$_2$), 1.31–1.21 (7H, t,CH$_3$ala+2xCH$_2$), 0.81–0.74 (5H,m,CH$_{3+2}$Hof CH$_2$cPr), 0.52 (2H,bs,2Hof CH$_2$cPr).
$^{13}$C NMR: δ174.1(CO), 160.1 (C2), 156.5 (C4), 151.2 (C6), 151.1 ('ipso'-Ph), 136.8 (C2'), 136.1 (C8), 131.5 (C3'), 130.0 ('m'-Ph), 125.2 (5'p'-Ph), 120.5 ('o'-Ph), 115.1 (C5), 69.3 (C5'), 66.1 (OCH$_2$), 59.3 (Cl'), 50.7 (CHala), 46.0 (C4'), 34.9 (C6'), 28.6 (CH$_2$-C2), 28.3 (CH$_2$-C3), 24.2 (CHcPr), 22.6 (CH$_2$-C4), 21.5 (CH$_3$ala), 14.3 (CH$_3$-C5), 7.8 (CH$_2$cPr).
MS ES$^+$: m/z 584.2 (100%, M$^+$), 585.2 (25%, M+H$^+$).
MS FAB: For $C_{28}H_{39}O_5N_7P$ requires 584.2750, found 584.2757.
BPLC: $t_R$ 40.294 (99.3%)-(100% water (0 mins), 20% water (35 mins), 20% water (45 mins), 100% water (55 mins)).
L-Alanine in-hexyl ester hydrochloride salt
$C_9H_{20N1}O_2Cl_1$, MW=209.75

This was synthesised according to Standard Procedure 2, using L-Alanine (2.0 g, 22.5mmol), hexan-1-ol (2.82 ml, 22.5 mmol), p-toluene sulfonic acid monohydrate (4.7 g, 24.7 mmol), and toluene (100 ml). L-alanine n-hexyl ester hydrochloride was isolated as a white powdery solid (3.32 g, 70.5%).
$^1$H NMR (MeOH-d$_4$): 5 4.31–4.18 (2H,m,OCH$_2$), 4.17–4.09 (1H,q,CHala), 1.75–1.66 (2H,m,OCH$_2$CH$_2$), 1.57 (3H,d,J=7.20 Hz,CH$_3$ala), 1.45–1.35 (6H,m,[CH$_2$]$_3$CH$_3$), 0.94–0.89 (3H,t,CH$_2$CH$_3$).
$^{13}$C NMR: δ170.1 (CO), 66.5 (OCH$_2$), 48.9 (CHala), 31.6 (OCH$_2$CH$_2$), 28.6 (O[CH$_2$]CH$_2$), 25.6 (CH$_2$CH$_2$CH$_3$), 22.6 (CH$_2$CH$_3$), 15.4 (CH$_3$ala), 13.4 (CH$_2$CH$_3$)
Phenyl-(n-b exyloxy-L-alaninyl)-phosphorochloridate
$C_{15}H_{23}N_1O_4P_1Cl_1$, MW=347.81

This was synthesised according to Standard Procedure 3, using L-Alanine n-hexyl ester hydrochloride salt (0.5 g, 2.38 mmol), PhOP(O)Cl$_2$ (0.36 ml, 2.38 mmol), triethylanine (0.66 ml. 4.77 mmol) in DCM (60 m1). The usual workup yielded the crude product as a yellow oil (0.69 g, 83.2%), which was stored in THF (4 ml) to give a 0.496M solution.
$^{31}$NMR: δ9.40, 9.1 0(1:1).
$^1$H NMR: δ7.44–7.14 (5H,m,OPh), 4.25 (1H,bs,NHala), 4.23–4.03 (3H,m,OCH$_2$+CHala), 1.70–1.63 (2H,m,CH$_2$-2), 1.57–1.54 (2H,m,CH$_2$-3), 1.47–1.32 (7H,m,CH$_3$ala+2CH$_2$-4,5), 0.93–0.91 (3H,dd,CH$_3$-6).
$^{13}$C NMR: δ173.2 (CO), 150.1 ('ipso'-Ph), 130.3 ('m'-Ph), 126.4 ('p'-Ph), 120.9 ('o'-Ph), 66.4 (OCH$_2$), 51.0 (CHala), 31.7 (CH$_2$-C2), 28.9 (CH$_2$-C3), 25.8 (CH$_2$-C4), 22.9 (CH$_2$-C5), 21.0 (CH$_3$ala), 14.4 (CH$_3$-C6).
(1S,4R)-4-(2-amino-6-cyclopropylamino-9H-purin-9-yl)-2-cyclopentene-1-methanol O-Phenyl-(n-hexyloxy-L-alaninyl)-phosphate.
C$_{29}$H$_{40}$N$_7$O$_5$P$_1$, MW=597.651

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (3 ml) and phenyl-(n-hexoxy-L-alaninyl)-phosphorochloridate (2.11 ml, 1.05 mmol, of a 0.496M solution in THF), at room temperature for 24 hrs. Additional phenyl-(n-hexoxy-L-alaninyl)-phosphorochloridate (1.5 ml, 0.68 mmol, of a 0.496M solution in THF), was added and the reaction stirred for a further 24 hrs. The crude product was purified by eluting with 3.0% MeOH in CHCl$_3$ (x2) to give the pure product as a pale yellow foamy solid
$^{31}$P NMR: δ3.94, 3.91 (1:1).
$^1$H NMR: δ7.52 (1H,d,J=8.00 Hz,H8), 7.36–7.31 (2H,m,'o'-Ph), 7.25–7.15 (3H,m,'m'+'p'-Ph), 6.26 (1H,bs,NHcPr), 6.13–6.08 (1H,m,H2'), 5.93–5.88 (1H,m,H3'), 5.58–5.53 (1H,m,H1'), 5.14 (2H,bs,NH$_2$), 4.28–3.89 (6H,m,CHala, OCH$_2$,H5'+NHala), 3.17 (1H,t,H4'), 3.04 (1H,bs,CHcPr), 2.87–2.75 (1H,m,1of H6'), 1.74–1.61 (3H,m,1of H6'+OCH$_2$CH$_2$), 1.43–1.31 (9H,t,CH$_3$ala+3xCH$_2$), 0.92–0.85 (5H,m, CH$_3$+2Hof CH$_2$cPr), 0.68–0.63 (2H,q,2Hof CH$_2$cPr).
$^{13}$C NMR: δ174.1C0, 160.1 (C2), 156.5 (C4), 151.2 (C6), 151.1 ('ipso'-Ph), 136.9 (C2'), 136.0 (C8), 131.4 (C3'), 130.0 ('m'-Ph), 125.3 ('p'-Ph), 120.5 ('o'-Ph), 115.0 (C5), 69.2 (C5'), 66.1 (OCH$_2$), 59.3 (Cl'), 50.7 (CHala), 46.0 (C4'), 34.9 (C6'), 31.7 (OCH$_2$CH$_2$), 28.8 (CH$_2$-ester), 25.8 (CH$_2$-ester), 24.2 (CHcPr), 21.9 (CH$_2$-ester), 21.5 (CH$_3$ala), 14.4 (CH$_3$-ester), 7.8 (CH$_2$cPr).
L-Alanine cyclo-hexyl ester hydrochloride salt
C$_9$H$_{16}$N$_1$O$_2$Cl$_1$J, MW=205.71

This was synthesised according to Standard Procedure 2, using L-Alanine (2.0 g, 22.5 mmol), cyclohexanol (2.34 ml, 22.5 mmol), p-toluene sulfonic acid monohydrate (4.7 g, 24.7 mmol), and toluene (100 ml). The p-toluene sulfonate salt was isolated as a pale orange solid (1.45 g).

The reaction was repeated using L-Alanine (3.0 g, 33.7 mmol), cyclohexanol (5.26 ml, 50.6 mmol),p-toluene sulfonic acid monohydrate (9.62 g, 50.6 mmol), and toluene (100 ml). L-alanine cyclohexyl ester hydrochloride salt was isolated as a white solid (3.15 g, 45.45%).
$^1$H NMR (MeOH-d$_4$): δ4.90 (1Hm,OCH), 4.12–4.04 (1H, q,CHala), 1.92–1.81 (2H,m,OCHCH$_2$), 1.80–1.63 (2H,m, OCHCH$_2$), 1.55 (3H,d,J=7.23 Hz,CH$_3$ala), 1.49–1.33 (6H, m,[CH$_2$]$_3$).
$^{13}$C NMR: δ169.5 (CO), 75.4 (OCH), 48.9 (CHala), 31.3 (2xCH$_2$-o), 25.2 (2xCH$_2$-M), 23.5 (p-CH$_2$), 15.3 (CH$_3$ala).
Phenyl-(c-hexyloxy-L-alaninyl)-phosphorochloridate
C$_{15}$H$_{21}$N$_1$O$_4$P$_1$Cl$_1$, MW=345.79

This was synthesised according to Standard Procedure 3, using L-Alanine c-hexyl ester hydrochloride salt (0.7 g, 3.4 mmol), PhOP(O)Cl$_2$ (0.51 ml, 3.4 mmol), triethylamine (0.95 ml 6.8 mmol) in DCM (60 ml). The usual workup yielded the crude product as a yellow oil (1.12 g, 95.2%), which was stored in THF (7 ml) to give a 0.46M solution.
31P NMR: δ9.43, 9.07 (1:1).
$^1$H NMR: δ7.44–7.33(2H,m,'o'-Ph), 7.32–7.20 (3Hm,'m'+'p'-Ph), 4.924.83 (1H,m,OCH), 4.55–4.42 (1H,m,NHala), 4.28–4.15 (1H,m,CHala), 1.89 (2H,bd,CH$_2$-'o'), 1.76 (1H, bd,CH$_2$-'o'), 1.54 (3H,d,CH$_3$ala), 1.49–1.32 (6H,m, CH$_2$3CH$_2$-'m'+'p').
$^{13}$C NMR: δ172.5 (CO), 150.1 ('ipso'-Ph), 130.3 ('m'-Ph), 126.4 ('p'-Ph), 121.0 ('o'-Ph), 74.9 (OCH), 51.1 (CHala), 31.8 (CH$_2$-'o'), 25.6 (CH$_2$-'p'), 21.0 (CH$_3$ala).
(1S,4R)-4-(2-amino-6-cyclopropylamino-9H-purin-9-yl)-2-cyclopeniene-1-methanol O-Phenyl-(c-hexyloxy-L-alaninyl)-phosphate. Cf 1707.
C$_{29}$H$_{38}$N$_7$O$_5$P$_1$, MW=595.635

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (3 ml) and phenyl-(c-hexoxy-L-alaninyl)-phosphorochloridate (2.28 ml, 1.05 mmol, of a 0.46M solution in THF), at room temperature for 24 hrs. The crude product was purified by eluting with 3–4% MeOH in CHCl$_3$, and then 2.5–3.0% MeOH in CHCl$_3$ to give the pure product as a pale yellow foamy solid (199 mg, 95.7%).
$^{31}$P NMR: δ4.06, 3.99 (1:1).
$^1$H NMR: δ7.42 (1H,d,J=8.15 Hz,H8), 7.23–7.18 (2H,n,'o'-Ph), 7.12–7.02 (3H,m,'m'+'p'-Ph), 6.31 (1H,bs,NHcPr), 5.98 (1H,bs,H2'), 5.78 (1H,bs,H3'), 5.43 (1H,bs,H1'), 5.21 (2H,bs,NH2), 4.66 (1H,bs,OCH), 4.17–4.02 (3H,m,H5'+NHala), 3.95–3.85 (1H,m,CHala), 3.05–2.94 (2H,m,H4'+CHcPr), 2.73–2–63 (1H,m,1of H6'), 1.69 (2H,bs,CH$_2$-'o'), 1.62–1.53 (2H,m,CH$_2$-'o'), 1.45–1.18 (9H,m,CH$_3$ala+3xCH$_2$-'m'+'p''), 0.76 (2H,d,2Hof CH$_2$cPr), 0.53 (2H,bs, 2Hof CH$_2$cPr).
$^{13}$C NMR: δ172.OCO, 158.4 (C2), 154.8 (C4), 149.7 (C6), 149.6 ('ipso'-Ph), 135.5 (C2'), 134.7 (C8), 130.0 (C3'), 128.6 ('m'-Ph), 123.8 ('p'-Ph), 119.1 ('o'-Ph), 113.1 (CS), 72.9 (OCH), 67.8 (C5'), 57.9 (Cl'), 59.4 (CHala), 44.7 (C4'), 34.5 (C6'), 30.3 (CH$_2$-'o'), 24.2 (CH$_2$-'m'), 22.8 (CHcPr), 22.5 (CH$_2$-'p'), 20.1 (CH$_3$ala), 6.4 (CH$_2$cPr).
MS ES$^+$: m/z 596.2 (100%, M$^+$), 597.3 (20%, M+H$^+$).
MS FAB: For C$_{29}$H$_{39}$O$_5$N$_7$P requires 596.2750, found 596.2750.
HPLC: t$_R$ 40.502 (99.8%)-(100% water (0 mins), 20% water (35 mins), 20% water (45 mins), 100% water (55 mins)).
L-alanine cyclobexane-methyl ester hydrochloride
C$_{10}$H$_{20}$N$_1$O$_2$Cl$_1$, MW=221.75

This was synthesised according to Standard Procedure 2, using L-Aianine (3.0 g, 33.7 mmol), cyclohexane methanol (4.15 ml, 33.7 mmol), p-toluene sulfonic acid monohydrate (7.05 g, 37.1 mmol), and toluene (100 ml). 9.2 g of the the PTSA salt was solubilised in DCM (50 ml), and washed with 10% K$_2$CO$_3$ (50 ml), and water (2×50 ml), dried over MgSO$_4$, filtered and the filtrate reduced to dryness to give a yellow oil. This was neutralised with 2M HCl, stirred for 2 hrs, and then freeze-dried to give the hydrochloride salt as a white solid (4.32 g, 75.8%).
$^1$H NMR (MeOH-d$_4$): δ4.194.01 (3H,m,OCH+CHala), 1.79–1.69 (5H,m,CH+o-CH$_2$), 1.58 (3H,d,J=7.21 Hz,CH$_3$ala), 1.37–1.20 (4H,m,m-CH$_2$), 1.09–0.98 (2H,q,p-CH$_2$).
$^{13}$C NMR: δ170.1 (CO), 71.3 (OCH$_2$), 48.9 (CHala), 37.3 (CH), 29.5 (2xCH$_2$-o), 26.4 (p-CH$_2$), 25.7 (2xCH$_2$-m), 15.4 (CH$_3$ala).

Phenyl-(cyclohexane-methoxy-L-alaninyl) phosphorochloridate
$C_{16}H_{23}N_1O_4P_1Cl_1$, MW=359.82

This was synthesised according to Standard Procedure 3, using L-Alanine cyclohexane-methyl ester hydrochloride salt (0.7 g, 3.16 mmol), PhOP(O)Cl$_2$ (0.47 ml, 3.16 mmol), triethylamine (0.88 ml. 6.31 mmol) in DCM (70 ml). The usual workup yielded the crude product as a yellow oil (1.10 g, 96.8%), which was stored in THF (6 ml) to give a 0.51M solution.

$^{31}$P NMR: δ9.35, 9.05 (1:1).
$^1$H NMR: δ4.61.4.50 (1H,q,NHala), 4.28-4.13 (1H,m,CHala), 4.04-4.00 (2H,q,OCH$_2$), 1.78–1.74 (7H,t,CH$_2$Hx+'o'-CH$_2$), 1.57–1.54 (3H,dd,CH$_3$ala), 1.06–0.96 (2H,q,'p'-CH$_2$).
$^{13}$C NMR: δ173.1 (CO), 150.1 ('ipso'-Ph), 130.3 ('m'-Ph), 126.4 ('p'-Ph), 121.0 ('o'-Ph), 71.4 (OCH$_2$), 51.0 (CHala), 37.4 (CHcHx), 29.9 (CH$_2$-'o'), 26.7 (CH$_2$-'m'), 25.9 (CH$_2$-'p'), 21.1 (CH$_3$ala).

(1S,4R)-4-(2-amino-6-cyclopropylamino-9H-purin-9-yl)-2cyclopentene-1-methanol O-Phenyl-(cyclohexane-methoxy-L-alaninyl)-phosphate. Cf1708.
$C_{30}H_{40}N_7O_5P_1$, MW=609.66

This was synthesised according to Standard Procedure 4, using (1S,4R)-4-(2-amino-6-cyclopropylamino-9H-purin-9-yl)-2-cyolopentene-1-methanol (100 mg, 0.35 mmol), tBuMgCl (0.7 mn, 0.7 mmol, of a 1.0M solution in THF), in THF (5 ml) and phenyl-(cyclohexane-methoxy-L-alaninyl)-phosphorochloridate (2.06 ml, 1.05 mmol, of a 0.51M solution in THF), at room temperature for 48 hrs. The crude product was purified by eluting with 4–6% MeOH in DCM, and then 3% MeOH in CHCl$_3$ to give the pure product as a pale yellow foamy solid (161.1 mg, 75.6%).

31p NMR: δ3.99,3.92 (1:1).
$^1$H NMR: δ7.40 (1H,d,J=7.07 Hz,H8), 7.24–7.19 (2H,t,'o'-Ph), 7.13–7.03 (3H,m,'m'+'p'-Ph), 6.00–5.96 (2H,m,H2'+NHcPr), 5.79 (1H,qJH3'), 5.45 (1H,d,H1'), 5.05 (2H,bs, NH$_2$), 4.16–4.01 (3H,m,OCH$_2$+NHala), 3.98–3.88 (1H,m, CHala), 3.86–3.74 (2Hm,H5'), 3.07–3.00 (1H,t,H4'), 2.94 (1H,bs,CHcPr), 2.74–2.63 (1H,m,1of H6'), 1.88–1.50. (7H, m,CHcHx+2CH$_2$-'o'), 1.31–1.27 (3H,t,CH$_3$ala), 1.21–0.99 (4H,m,2CH$_2$-'m'), 0.89–0.79 (2H,q,CH$_2$-'p'), 0.75 (2H,d, 2Hof CH$_2$cPr), 0.54–0.50 (2H,t,2Hof CH$_2$cPr).
$^{13}$C NMR: δ174.1(CO), 160.2 (C2), 156.4 (C4), 151.2 (C6), 151.1 ('ipso'-Ph), 136.7 (C$_2$'), 136.0 (C8),131.5 (C3'), 130.0 ('m'-Ph), 125.2 ('p'-Ph), 120.5 ('o'-Ph), 115.1 (C5), 71.0 (OCH$_2$), 69.3 (C5'), 59.3 (Cl'), 50.7 (CHala), 46.1 (C4'), 37.4 (CHcHx), 34.9 (C6'), 29.9 (CH$_2$-'o'), 26.6 (CH$_2$-'m'), 25.9 (CH$_2$-'p'), 24.2 (CHcPr), 21.5 (CH$_3$ala), 7.8 (CH$_2$cPr).
MS ES$^+$: miz 610.3 (50%, M+l$^+$), 632.3 (100%, M+Na$^+$), 633.3 (M+H+Na$^+$).
MS FAD: For $C_{30}H_{40}O_5N_7NaP$ requires 632.2726, found 632.2710.
HPLC: $t_R$ 42.859 (100%)-(100% water (0 mins), 20% water (35 mins), 20% water (45 mins), 100% water (55 mins)).

4-Chlorophenyl-phosphorodichloridate
$C_6H_4O_2P_1Cl_3$, MW=246.43

Phosphorus oxychloride (2 ml, 21.5mmol) was stirred with anhydrous diethylether (70 ml) in a 250 ml RBF. To this was added, dropwise, a solution of 4-chlorophanol (2.1 ml, 21.5 mmol), and anhydrous triethylamine (3.0 ml, 21.5 mmo) in anhydrous diethylether (30 ml) at –80° C. This was stirred vigorously at –80° C. for 1 hr and left to rise to room temperature over 16 hrs. The triethylamine hydrochloride salt was filtered off, and the filtrate reduced to dryness to give the crude product as a yellow oil (4.61 g, 87.2%).
$^3$P NMR: δ4.99 (s).
$^{s3}$C NMR: δ148.4 ('ipso'-PhX, 133.2 ('p'-Ph), 130.7 ('m'-Ph), 122.4 ('o'-Ph).

4-Chlorophenyl-(methoxy-L-alaninyl)-phosphorochloridate
$C_{10}H_{12}N_1O_4P_1Cl_2$, MW=246.43

This was synthesised according to Standard Procedure 3, using L-Alanine methyl ester hydrochloride (2.61 g, 18.7 mmol) and p-chlorophenyl phosphorodichloridate (4.61 g, 18.7 mmol) and triethylamine (5.21 ml, 37.4 mmol) in anhydrous DCM (100 ml). The usual workup yielded the crude product as a colourless crude oil (3.76 g, 64.4%) which was stored in anhydrous THF (20 ml) to give a 0.6M solution that was used without further purification.
$^{31}$ P NMR: δ9.48, 9.25 (1:1).
$^1$H NMR: δ7.36 (2H,d,J=8.20 Hz,'o'-Ph), 7.32–7.22 (2H, m,'m'-Ph), 4.69 (1H,d,NHala), 4.27-4.15 (1H,m,CHala), 3.82 (3H,d,OCH$_3$), 1.56–1.53 (3H,dd,J=7.04 Hz,CH$_3$ala).
$^{13}$C NMR: δ173.4 (CO), 148.6 ('ipso'-Ph), 131.9 ('p'-Ph), 130.3 ('m'-Ph), 122.3 ('o'-Ph), 53.2 (OCH$_3$), 50.9 (CHala), 20.9 (CH$_3$ala).

(1S,4R)-4-(2-amino-6-cyclopropylamino-9H-purin-$^9$-yl)-2-cyclopentene-1-methanol O-[4-chlorophenyl-(methoxy-L-alaninyl)]-phosphate. Cf 1620.
$C_{24}H_{29}N_7O_5P_1Cl_1$, MW=562.02

This was synthesised according to Standard Procedure 4, using (1S,4R)-4-(2-amino-6-cyclopropylamino-9H-purin-9-yl)-2-cyclopentene-1-methanol (250 mg, 0.87 mmol), tBuMgCl (1.75 ml, 1.75 mmol of a 1.0M solution in THF), and 4-chlorophenyl-(methoxy-L-alaninyl)-phosphorochloridate (4.37 ml, 2.62 mmol, of a 0.6M solution in THF), in anhydrous THF (13 ml) stirring at room temperature for 24 hrs. The crude product was purified by eluting with 3% MeOH in CHCl$_3$ to give the pure product as white foamy solid (364.5 mg, 74.50/%).
$^{31}$P NMR: δ4.01 (s).
$^1$H NMR: δ7.42 (1H,d,HS), 7.22–7.17 (2H,m,'m'-Ph), 7.09–7.03 (2H,t,'o'-Ph), 5.99 (1H,d,H2'), 5.93 (1H,s,H3'), 5.83 (1H,bs,NHcPr), 5.45 (1H,bs,H1'), 4.96 (2H,bs,NH$_2$), 4.11 (2H,bs,H5'), 4.03–3.86 (1H,m,CHala), 3.62 (3H,s, OCH$_3$), 3.07 (1H,d,J=5.9 Hz,H4'), 25 2.92 (1H,bs,CHcPr), 2.76–2.64 (1H,m,1of H6'), 1.64–1.59 (1H,t,1of H6'), 1.32–1.26 (3H,q,CH$_3$ala), 0.76 (2H,d,J=6.40 Hz,2Hof CH$_2$cPr), 0.53 (2H,bs,2Hof CH$_2$cPr).
$^{13}$C NMR: δ174.4 (CO), 160.4 (C2), 156.7 (C4), 151.3 (C6), 149.7 ('ipso'-Ph), 136.7 (C2'), 135.9 (C8), 131.6 (C3'), 130.5 ('p'-Ph), 130.0 ('m'-Ph), 121.9 ('o'-Ph), 115.2 (C5), 69.4 (C5'), 59.25 (Cl'), 52.9(OCH$_3$), 50.6 (CHala), 46.0 (C4'), 34.9 (C6'), 24.1 (CHCPr), 30 21.4 (CH3ala), 7.8 (CH$_2$cPr).
HPLC: $t_R$ 32.693, 33.012 (100%)-(100% water (0 mins), 20% water (35rains), 20% water (45 mins), 100% water (55 mins)).

4-Bromophenyl-phosphorodichloridate
$C_6H4O_2Cl_2Br_1$, MW=289.87

This was synthesised by a method analogous to that of 4-chlorophenyl-phosphorodichloridate, except using: Phosphorus oxychloride (3.29 g, 2 ml, 21.5 mmol), and 4-bromophenol (3.71 g, 21.5 mmol) in anhydrous diethylether (70 ml), and anhydrous triethylamine (2.71 g, 3 ml, 21.5 mmol) in anhydrous diethylether (30 ml). The reaction was stirred at –80° C. to room temperature for 1 6 hrs. After filtration, and removal of the solvent, the product was obtained as a clear liquid (5.14 g, 82.6%).
$^{31}$P NMR: δ4.88 (s).
1H NMR: δ7.63 (2H,d,J=8.14 Hz,'o'-Ph), 7.28 (2H,t,'m'-Ph),
$^{13}$C NMR: δ149.0('ipso'-Ph), 133.7 ('m'-Ph), 122.6 ('o'-Ph), 120.9 ('p'-Ph).

4-Bromophenyl-(methoxy-L-alaninyl)-phosphorochloridate
$C_{10}H_{12}N_1O_4P_1Cl_1Br_1$, MW=356.55

This was synthesised according to Standard Procedure 3, using L-alanine methyl ester hydrochloride salt (10 g, 7.1 6 mmol), 4-bromophenyl-phoshorodichloridate (0.82 g, 7.16 mmol), triethylamine (2 ml. 14.3 mmol) in DCM (70 ml). The usual workup yielded the crude product as a yellow oil (2.24 g, 87.7%), which was stored in THF (12 ml) to give a 0.524M solution.

31P NMR: δ9.16, 9.10 (1:1).

$^{13}$C NMR: δ173.4(CO), 150.1 ('ipso'-Ph), 133.3 ('m'-Ph), 122.7 ('o'-Ph), 119.6 ('p'-Ph), 53.3 (OCH$_3$), 51.0 (CHala), 20.9 (CH$_3$ala).

(1S,4R)-4-(2-amino-6-cyclopropylamino-9H-purin-9-yl)-2-cyclopentene-1-methanol O-[4-bromophenyl-(methoxy-L-alaninyl)]-phosphate. Cf1710.

$C_{24}H_{29}N_7O_5P_1Br_1$, MW=606.42

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (5 ml) and 4-bromophenyl-(methoxy-L-alaninyl)-phosphorochloridate (2.0 ml, 1.05 mmol, of a 0.524M solution in THF), at room temperature for 24 hrs. The crude product was purified by eluting with 4–6% MeOH in DCM, and then in 4% MeOH in DCM, to give the pure product as a white foamy solid (115.2 mg, 54.4%).

$^{31}$p NMR: δ3.96 (s).

$^1$H NMR: δ7.42 (1H,d,H8), 7.34–7.30 (2H,dd,J=8.73 Hz,'o'-Ph), 7.03–6.97 (2H,t,J=8.68 Hz,'m'-Ph), 6.02–5.97 (2H,m,H2'+NHcPr), 5.83–5.79 (1H,m,H3'), 5.43 (1H,t,H1'), 5.06 (2H,bs,NH$_2$), 4.28–4.04 (3H,m,H5'+NHala), 4.02–3.85 (1H,m,CHala), 3.61 (3H,d,OCH$_2$), 3.05 (1H,d,J=6.09 Hz,H4'), 2.94 (1H,d,CHcPr), 2.75–2.66 (1H,m,1of H6'), 1.66–1.56 (1Hm,1of H6'), 1.31–1.25 (3H,dd,CH$_3$ala), 0.79–0.72 (2H,q,2Hof CH$_2$cPr), 0.54–0.49 (2H,t,2Hof CH$_2$cPr).

$^{13}$C NMR: δ174.4(CO), 160.3 (C2), 156.6 (C4), 151.3 (C6) 150.2 ('ipso'-Ph), 136.7 (C2'), 136.0 (C8), 133.0 ('m'-Ph), 131.6 (C3'), 122.4 ('o'-Ph), 118.1 ('p'-Ph), 115.2 (C5), 69.4 (C5'), 59.3 (Cl'), 52.9 (OCH$_3$), 50.6 (CHala), 46.0 (C4'), 34.8 (C6'), 24.2 (CHcPr), 21.3 (CH$_3$ala), 7.8 (CH$_2$cPr).

MS ES$^+$: m/z 606.13 (40%, M$^+$), 628.1065 (100%, 79-M+Na$^+$), 630.0967 (95%, 81-M+Na$^+$).

MS FAB: For $C_{24}H_{29}O_5N_7NaPBr$ requires 628.1049, found 628.1058, and $C_{24}H_{29}O_5N_7NaP$ $^8$1Br requires 630.1028, found 630.1042.

HPLC: $t_R$ 35.882 (100%)-(100% water (0 mins), 20% water (35 mins), 20% water (45 mins), 100% water (55 mins)).

4-Fluorophenyl-phosphorodichlondate $C_6H_4O_2P_1Cl_2F_1$, MW=228.97

This was synthesised by a method analogous to that of 4-chlorophenyl-phosphorodichloridate, except using: Phosphorus oxychloride (3.29 g, 2 ml, 21.5 mmol), and 4-fluorophenol (2.41 g, 21.5 mmol) in anhydrous diethylether (70 ml), and anhydrous triethylamine (2.71 g, 3 ml, 21.5 mmol) in anhydrous diethylether (30 ml). The reaction was stirred at –80° C. for 4 hrs, and then at room temperature for 2 hrs. After filtration, and removal of the solvent, the product was obtained as a clear liquid (4.08 g, 83.0%).

$^{31}$P NMR: δ5.50 (s).

$^1$H NMR: δ7.29–7.24 (2H,m,'o'-Ph), 7.09 (2H,t,J=8.29 Hz,'m'-Ph), $^3$C NMR: δ159.7('ipso'-Ph), 145.8 ('m'-Ph), 122.6 ('o'-Ph), 117.5 ('p'-Ph).

4-Fluorophenyl-(methoxy-L-alaninyl)-phosphorochloridate $C_{10}H_{12}N_1O_4P_1Cl_1F_1$, MW=295.65

This was synthesised according to Standard Procedure 3, using L-alanine methyl ester hydrochloride salt (1.0 g, 7.16 mmol), 4-fluorophenyl-phoshorodichloridate (1.64 g, 7.6 mmol), triethylamine (2 ml. 14.3 mmol) in DCM (70 ml). The usual workup yielded the crude product as a yellow oil (1.97 g, 93.0%), which was stored in THF (12 ml) to give a 0.56M solution.

31P NMR: δ9.84, 9.60 (1:1).

$^1$H NMR: δ7.32–7.23(2H,m,'o'-Ph), 7.12–7.06 (2H,m,'m'-Ph), 4.69 (1H,bs,NHala), 4.22 (1H,bs,CHala), 3.82 (3H,d,OCH$_3$), 1.57–1.53 (3H,m,CH$_3$ala).

$^{13}$C NMR: δ173.5(CO), 161.6 ('ipso'-Ph), 145.9 ('m'-Ph), 122.5 ('o'-Ph), 117.0 ('p'-Ph), 53.2 (OCH$_3$), 50.9 ((Hala), 20.9 (CH$_3$ala).

(1S,4R4-(2-amino-6-cyclopropylamino-9H-purin-9-yl)-2-cyclopentene-1-methanol O-[(4-fluoropheny]-(methoxy-L-alaninyl)]-phosphate. Cf1737.

$C_{24}H_{29}N_7O_5P_1F_1$, MW=545.57

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (5 ml) and 4-fluorophenyl-(methoxy-L-alaninyl)-phosphorochloridate (1.89 ml, 1.05 mmol, of a 0.56M solution in THF), at room temperature for 24 hrs. The solvent was removed under reduced pressure and the residue columned in 2.5–5% methanol in chloroform, and then in 3% methanol in chloroform, to give the pure product as a pale yellow foamy solid (62.0 mg, 32.5%).

$^{31}$P NMR: δ4.24, 4.23, 4.20, 4.19.

$^1$H NMR: δ7.52 (1H,d,H8), 7.21–7.14 (2H,m,'o'-Ph), 7.03–6.97 (2H,m,'m'-Ph), 6.16 (1H,bs,NHcPr), 6.10–6.07 (1H,q,H2'), 5.93–5.89 (1H,q,H3'), 5.44 (1H,d,H1'), 5.14 (2H,bs,NH$_2$), 4.23–3.98 (4H,m,H5',NHala+CHala), 3.72 (3H,d,OCH$_2$), 3.16 (1H,d,J=6.03 Hz,H4'), 3.03 (1H,d, CHcPr), 2.86–2.74 (1H,m,1of H6'), 1.76–1.66 (1H,m,1of H6'), 1.42–1.35 (3H,dd,CH$_3$ala), 0.89–0.83 (2H,q,2Hof CH$_2$cPr), 0.65–0.60 (2H,t,2Hof CH$_2$cPr).

$^{13}$C NMR: δ174.4(CO), 161.5 (C2), 160.3+156.6 ('p'-Ph), 156.6 (C4), 151.3 (C6) 150.2 ('ipso'-Ph), 136.8 (C2'), 136.0 (C8), 131.6 (C3'), 121.9 ('o'-Ph), 115.1 (C5), 69.3 (C5'), 59.3 (Cl'), 52.9 (OCH$_3$), 50.6 (CHala), 46.0 (C4'), 34.9 (C6'), 24.2 (CHcPr), 21.3 (CH$_3$ala), 7.8 (CH$_2$cPr).

HPLC: $t_R$ 31.536 (100%)-(100% water (0 mins), 20% water (35 mins), 20% water (45 mins), 100% water (55 mins)).

4-Iodophenyl-phosphorodichloridate $C_6H_4O_2P_1Cl_2I_1$, MW=336.07

This was synthesised by a method analogous to that of 4-chlorophenyl-phosphorodichloridate, except using: Phosphorus oxychloride (3.29 g, 2 ml, 21.5 mmol), and 4-iodophenol (4.72 g, 21.5 mmol) in anhydrous diethylether (60 ml), and anhydrous triethylamine (2.71 g, 3 ml, 21.5 mmol) in anhydrous diethylether (20 ml). The reaction was stirred at –80° C. for 4 hrs, and then at room temperature for 2 hrs. After filtration, and removal of the solvent, the product was obtained as a clear liquid (6.2 g, 85.8%).

$^{31}$P NMR: δ4.72 (s).

$^1$H NMR: δ7.71 (2H,d,J=8.59 Hz,'o'-Ph), 7.06–7.02 (2H, dd,J=8.80 Hz,'m'-Ph), $^1$C NMR: δ149.9('ipso'-Ph), 139.8 ('m'-Ph), 122.9 ('o'-Ph), 91.9 ('p'-Ph).

4-Iodophenyl-(methoxy-L21alaninyl)-phosphorochloridate $C_{10}H_{12}N_1O_4P_1Cl_1I_1$, MW=403.55

This was synthesised according to Standard Procedure 3, using L-alanine methyl ester hydrochloride salt (1.0 g, 7.16 mmol), 4-iodophenyl-phoshorodichloridate (2.41 g, 7.16 mmol), triethylamine (2 ml. 14.3 mmol) in DCM (70 ml). The usual workup yielded the crude product as a yellow oil (3.59 g, >100%), which was stored in THF (14 ml) to give a 0.51M solution.

$^{31}$P NMR. δ9.31, 9.08 (1:1).
$^{1}$H NMR: 7.74–7.69(2H,m,'o'-Ph), 7.32–7.05 (2H,m,'m'-Ph), 4.73 (1H,bs,NHala), 4.20 (1H,bs,CHala), 3.81 (3H,d, OCH$_3$), 1.56–1.53 (3H,dd,J=7.06 Hz,CH$_3$ala).
$^{13}$C NMR: δ173.4(CO), 149.9 ('ipso'-Ph), 139.5 ('m'-Ph), 123.0 ('o'-Ph), 90.4 ('p'-Ph), 53.3 (OCH$_3$), 50.9 (CHala), 20.9 (CH$_3$ala).
(1S,4R)-4-(2-amino6-cyclopropylamino-9H-purin-9-yl)-2-cyclopentene-1-methanol O-[4-iodophenyl-(methoxy-L-alaninyl)]-phosphate. Cf1738.
C$_{24}$H$_{29}$N$_7$O$_5$P$_1$I$_1$, MW=653.48

This was synthesised according to Standard Procedure 4, using (1S,4R)-4-(2-amino-6-cyclopropylamino-9H-purin-9-yl)-2-cyclopentene-1-methanol (100 mg, 0.35 mmol), tBuMgCl (0.7 ml, 0.7 mmol, of a 1.0M solution in THF), in THF (5 ml) and 4-iodophenyl-(methoxy-L-alaninyl)-phosphochloridate (2.05 ml, 1.05 mmol, of a 0.51M solution in THF), at room temperature for 48 hrs. The solvent was removed under reduced pressure and the residue columned in 3–6% methanol in chloroform, and then in 3% methanol in chloroform, to give the pure product as a white foamy solid (82.0 mg, 29.9%).
$^{31}$ P NMR: δ3.92 (s).
$^{1}$H NMR: δ7.63–7.59 (2H,dd,J=8–65 Hz,'m'-Ph), 6.98 (2H, t,J-8.20 Hz'o'-Ph), 6.25 (1H,bs,NHcPr), 6.09 (1H,t,H2'), 5.91 (1H,t,H3'), 5.54 (1H,d,H1'), 5.21 (2H,bs,NH$_2$), 4.35–4.16 (3H,m,H5',NHala), 4.07–3.95 (1H,m,CHala), 3.71 (3H,d,OCH$_3$ala), 3.15 (1H,d,J=7.23 Hz,H4'), 3.03 (1H, bs,CHcPr), 2.85–2.74 (1H,m,1of H6'), 1.761.65 (1H,m,1of H6'), 1.43–1.35 (3H,t,CH$_3$ala), 0.89–0.83 (2H,q,2Hof CH$_2$cPr), 0.63 (2H,bs,2Hof CH$_2$cPr).
$^{13}$C NMR: δ174.4(CO) 160.2 (C2), 156.5 (C4), 151.1 (C6) 151.0 ('ipso'-Ph), 139.0 (C2'), 136.8 ('m'-Ph), 136.0 (C8), 131.5 (C3'), 122.8 ('o'-Ph), 115.0 (C5), 88.9 ('p'-Ph), 69.4 (C5'), 59.3 (C1'), 52.9 (OCH$_3$), 50.6 (CHala), 46.0 (C4'), 34.8 (C6'), 24.2 (CHcPr), 21.3 (CH$_3$ala), 7.8 (CH$_2$cPr).
HPLC: t$_R$ 33.848 (100%)-(100% water (0 mins), 20% water (35 mins), 20% water (45 mins), 100% water (55 mins)).
L-Alanine (3-pentyl) ester hydrochloride salt

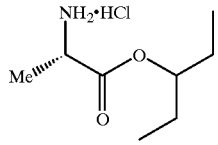

Tionyl chloride (1.6 ml, 0.022 M) was added dropwise to a stirred solution of 3-pentanol (18.2 ml, 0.17 M) at 0° C. under nitrogen. The mixture was stirred for 30 minutes, then allowed to warm to room temperature. L-Alanine (pre-dried at 60° C. over P$_2$O$_5$ for 4 hrs: 1.0 g, 0.011 M) was added and the resulting suspension was heated at reflux overnight (the reaction mixture became a clear, colourless solution). The solvent was removed under reduced pressure to leave an oil which was repeatedly triturated and coevaporated with diethyl ether, then petrol (60/80) to remove traces of 3-pentanol. The resulting oily residue solidified on drying under high vacuum to give a peach-coloured solid (1.96 g, 10 mmol, 89%).
δ$_H$ (d$_4$-CH$_3$OH, 300 MHz) 0.94 (t, 6H, O-CH(CH$_2$CH$_3$)$_2$, J =7), 1.57 (d, 3H, CH$_3$-ala, J=7), 1.67 (m, 4H, O-CH (CH$_2$CH$_3$)$_2$, J=7), 4.12 (q, 1H, CH-ala, J =7), 4.88 [m, 1H, O-CH(C$_2$H$_2$)$_2$]; δ$_C$(d$_4$-CH$_3$OH, 75 MHz) 8.87 [O-CH (CH$_2$CH$_3$)$_2$], 15.38 (CH$_3$-ala), 26.39, 26.44 [O-CH (CH$_2$CH$_3$)$_2$], 48.82 (CH-ala), 79.88 [O-CH(C$_2$H)$_2$], 170.03 (C=O).

Phenyl (3-pentyloxy-L-alaninyl)phosphorochloridate

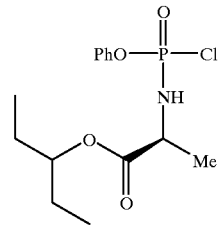

Prepared according to Standard Procedure 3, from phenyl dichlorophosphate (0.45 ml, 3.0 mmol), dry triethylamine (0.8 ml, 6.0 mmol), L-alanine (3-pentyl) ester hydrochloride salt 1a (0.583 g, 3.0 mmol) and dry DCM (60 ml total). The crude product was obtained as a clear, pale yellow oil (1.055 g, >100%)
δ$_P$ (CDCl$_3$, 121 Mz) 8.99, 9.37
The product was redissolved in dry THF 5 ml) and used as a 0.211 g/ml solution.
(1S,4R)-4-(2-amino-6-cyclopropylamino-9H-purin-9-yl)-2-cyclopentene-1-methanol O-[phenyl (3-pentyloxy-L-alaninyl)phosphate [Cf 1685]

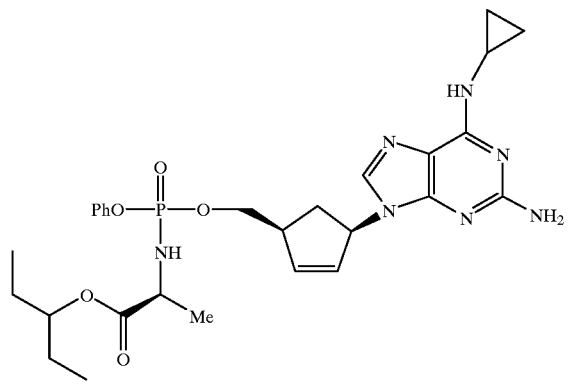

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol), phenyl(3-pentyloxy-L-alaninyl)phosphorochloridate 1b (3.3 ml of 0.211 g/ml solution 4 2.1 mmol) and dry THF (8 ml). TLC (8% MeOH in CHCl$_3$) showed the reaction to be complete after 1.5 hrs. The crude residue was purified twice by column chromatography, using (i) MeOH:CHCl$_3$ (4:96) and (ii) MeOH:CHCl$_3$ (3:97) as eluent, to give the product as a clear, colourless oil, which solidified to a white foam after trituration and coevaporation with diethyl ether (0.202 g, 0.35 mmol, 50%). δ$_P$ (CDCl$_3$, 121 MHz) 3.89; 31 (CDCl$_3$, 300 MHz) 0.66 (m, 2H, CH$_2$-CPr), 0.90 [m, 8H CH$_2$-cPr and CH(CH$_2$CH$_3$)$_2$], 1.43 (m, 3H, CH$_3$-ala), 1.58 [m, 4H, CH(CH$_2$CH$_3$)$_2$], 1.72 (m, 1H, 6$^1$H.), 2.82 (m, 1H, $^{6'}$H$_b$), 3.05 (m, 1H, C1H-cPr), 3.20 (m, 1H, 4'H), 3.77 (m, 1H, CH-ala), 4.05 (m, 1H, NH-ala), 4.22 (m, 2H, 5$^1$H), 4.80 (m, 1H, O-CH—), 4.89 (s, 2 M, NH$_2$), 5.56 (m, 1H, 1'H), 5.78 (bs, 1H, NH-cPr), 5.93 (m, 1H, 3$^1$H), 6.12 (m, 1H, 2$^1$H), 7.26 (m, 5H, ArH), 7.51 (d, 1H, 8H); δ$_C$ (CDCl$_3$, 75 MHz) 6.37 (CH$_2$-cPr), 8.50 [CH(CH$_2$CH$_3$)$_2$], 20.28 (CH3-ala), 22.68 (CH-cPr), 25.28, 25.38 [CH(CH$_2$CH$_3$)$_2$], 33.51, 33.60 (6° C.), 44.59, 44.69 (4° C.), 49.40 (CH-ala), 57.79, 57.83 (1° C.), 67.90 (5° C.), 7729 (OCH), 113.86 (5C), 119.10–119.18 (o-Ph), 123.84 (p-Ph), 128.61 (m-Ph), 130.09, 130.16 (3'C), 134.45, 134.56 (8C), 135.27, 135.41 (2'C), 149.66–149.93 (6C and ipso-Ph), 155.26 (4C), 158.95 (2C), 172.32, 172.44 (C=O); m/z (FAB) 584.2751 (MW, $C_{28}H_{39}N_7O_5P$ requires 584.2750).

L-Alanine (3,3-dimethyl-1-butyl) ester hydrochloride salt

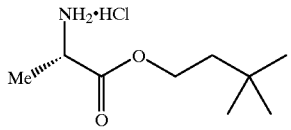

Prepared according to Standard Procedure 2, from L-alanine (1.6 g, 18 mmol), PTSA monohydrate (3.8 g, 20 mmol), 3,3-dimethyl butan-1-ol (2.2 ml, 18 mmol) and toluene (100 ml). Conversion to the hydrochloride salt: the p-toluene sulfonate salt was redissolved in $CHCl_3$ and washed with 10% potassium carbonate solution and water. The organuc layer was dried ($MgSO_4$), filtered and the solvent was removed under reduced pressure to give the crude product as an oil. Aq. HCl (1 M), was added and the solution stirred for 30 minutes at room temperature. The solution was freeze-dried to give the hydrochloride salt as a white solid (3.31 g, 15.8 mmol, 88%).

$\delta_H$ ($d_4$-$CH_3OH$, 300M ) 0.93 [s, 9H, O—$(CH_2)_2(CH_3)_3$], 1.50 (d, 3H, $CH_3$-ala, J=7), 1.59 (t, 2H, O-$CH_2CH_2$, J=7), 4.05 (q, 1I, CH-ala, J 7), 4.25 (m, 2H, O—$CH_2$); 8c ($d_4$-$CH_3OH$, 75 MHz) 15.18 ($CH_3$-ala), 28.91 [$C(CH_3)_3$], 29.54 [$C(CH_3)_3$], 41.62 (O—$CH_2CH_2$—), 48.85 (CH-ala), 64.11 ()—$CH_2CH_2$—), 170.03 (C=O).

Phenyl(3,3-dimethyl-1-butoxy-L-alaninyl) phosphorochloridate

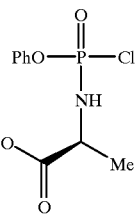

Prepared according to Standard Procedure 3, from phenyl dichlorophosphate (0.45 ml, 3.0 mmol), dry triethylamine (0.8 ml, 6.0 mmol), L-alanine (3,3-dimethyl-1-butyl) ester hydro-chloride salt 2a (0.632 g, 3.0 mmol) and dry DCM (60 ml total). The crude product was obtained as a clear, pale yellow oil (1.038 g, 99%).

$\delta_p$ ($CDCl_3$, 121 MHz) 8.94, 9.30

The product was redissolved in dry THF (5 ml) and used as a 0.208 g/ml solution (1S,4R)-4-(2-amino6cyclopropylamino-9H-purin-9-yl)-2-cyclopentene-1-methanol O-[phenyl(3,3-dimethyl-]-butoxy-L-alaninyl)phosphate [Cf 1687]

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol), phenyl (3,3-dimethyl-1-butoxy-L-alaninyl) phosphorochloridate 2b (3.5 ml of 0.208 g/ml solution, 2.1 mmol) and dry THF (8 ml). TLC (8% MeOH in $CHCl_3$) showed the reaction to be complete after 1.5 hrs. The crude residue was purified twice by column chromatography, using MeOH:$CHCl_3$ (4:96) as eluent, to give the product as a clear, colourless oil, which solidified to a white foam after trituration and coevaporation with diethyl ether (0.287 g, 0.5 mmol, 69%). 5? ($CDCl_3$, 121 M) 3.83; 5H ($CDCl_3$, 300 M) 0.66 (m, 2H, $CH_2$,-cPr), 0.90 (m, 2H, $CH_2$cPr), 0.97 [s, 9H, $C(CH_3)_3$]1.41 (m, 3H1, $CH_3$-ala), 1.57 (m, 2H, O—$CH_2CH_2$), 1.74 (m, 111, $6^1H$.), 2.82 (m, 111, $^6H_b$), 3.05 (m, 1ill CH-cPr), 3.20 (m, 1H, 4'H), 3.70 (m, 1H CH-ala), 4.04 (m, 1H, NH-ala), 4.22 (i, 4H, 5'H and C-$CH_2CH_2$), 4.88 (s, 2H, $NH_2$), 5.57 (m, 1H, 1'H), 5.75 (bs, 1H, NH-cPr), 5.93 (m, 1H, 3'H), 6.12 (m, 1H, 2'H), 7.27 (m, 5H, ArH), 7.52 (d, 1H, 8H); 5c ($CDCl_3$, 75 MHz) 6.35 ($CH_2$-cPr), 19.95, 20.01 ($CH_3$-ala), 22.69 (CH-cPr), 28.52 [$C(CH_3)_3$], 28.52 [$C(CH_3)_3$], 33.49, 33.57 (6'C), 40.59, 40.63 (O$CH_2CH_2$—), 44.58, 44.68 (4'C), 49.28 (CH-ala), 57.79, 57.83 (1'C), 62.28, 62.31 (O$CH_2CH_2$—), 67.86, 67.94 (5'C), 113.81 (5C), 119.10, 119.16 (p-Ph), 123.84 (o-Ph), 128.61 (m-Ph), 130.10, 130.16 (3'C), 134.47,134.56 (8C), 135.29, 135.40 (2'C), 149.67–149.75 (6C and ipso-Ph), 155.25 (4C), 158.96 (2C), 172.55, 172.65 (C=O); m/z (FAB) 598.2896 ($MH^+$, $C_{29}H_{41}N_7O_5P$ requires 598.2907).

L-Alanine (4-methyl-1-pentyl) ester p-toluene sulfonate salt

Prepared according to Standard Procedure 2, from L-alanine (1.6 g, 18 mmol), p-TSA monohydrate (3.8 g, 20 mmol), 4-methyl pentan-1-ol (2.24 ml, 18 mmol) and toluene (100 ml). The p-toluene sulfonate salt was isolated as a white solid (6.082 g, 17.6 mmol, 98%). 8H ($d_4$-CH3OH, 300 MHz) 0.93 [d, 6H, $CH(CH_3)_2$], 127 (m, 2II, O-$CH_2CH_2CH_2$—), 1.54 (d, 3H, $CH_3$-ala), 1.59 (m, 1H, $CH(CH_3)_2$), 1.69 [m, 2H, O—$(CH_2)2C$, 2.39 (s, 3H, $CH_3$, p-TSA), 4.10 (m, 1H, CH-ala), 4.24 (m, 2H, O-$CH_2$), 7.25 (d, 2H, ArH, p-TSA), 7.72 (d, 2H, ArH, p-TSA); $\delta_C$ ($d_4$-$CH_3OH$, 75 MHz) 15.23 ($CH_3$-ala), 20.31 ($CH_3$-pTSA), 21.83 [$CH(CH_3)_2$], 26.45 (O-$CH_2CH_2CH_2$—), 27.87 [$CH(CH_3)_2$], 34.93 (O—$CH_2CH_2CH_2$—), 48.85 (CH-ala), 66.77 [O—$CH_2(CH_2)_2$], 125.93 (o-Ph, p-TSA), 128.83 (m-Ph, p-TSA), 140.75 (ipso-C-$CH_3$,p-TSA), 142.39 (ipso-C-S, p-TSA), 170.07 (C=O).

Phenyl(4-methyl-1-pentyloxy-L-alaninyl) phosphorochloridate

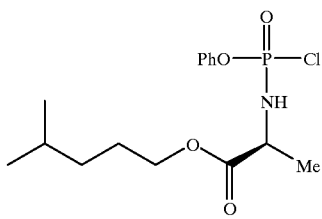

Prepared according to Standard Procedure 3, from phenyl dichlorophosphate (0.9 ml, 6.0 mmol), dry triethylamine (1.7 ml, 12.0 mmol), L-alanine (4-methyl-1-pentyl) ester p-toluene sulfonate salt 3a (2.081 g, 6.0 mmol) and dry DCM (100 ml total). The crude product was obtained as a clear, colourless oil (1.79 g, 85%).
$\delta_P$ (CDCl$_3$, 121 MHz) 8.95, 9.31
The product was redissolved in dry THF (10 ml) and used as a 0.179 g/ml solution.

(1S,4R)-4-(2-amino-6-cyclopropylamino-9H-purin-9-y))-2-cyclopentene-1-methanol O-[phenyl (4-methyl-1-pentyloxy-L-alaninyl)phosphate [Cf 1721]

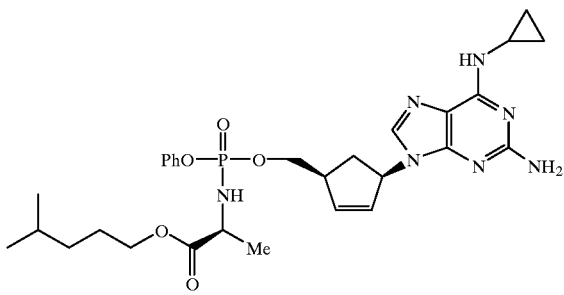

Prepared according to Standard Procedure 4, from (1S, 4R)-4-(2-amino-6-cyclopropylamino-9H-purin-9-yl)-2-cyclopentene-1-methanol (0.2 g, 0.7 mmol), $^t$BuMgCl (1.0M in THF: 1.4 ml, 1.4 mmol), phenyl(4-methyl-1-pentyloxy-L-alaninyl)phosphorochloridate 3b (4.1 ml of 0.179 g/ml solution, 2.1 mmol) and dry THF (10 ml). TLC (8% MeOH in CHCl$_3$) showed the reaction to be complete after 3 hrs. The crude residue was purified by column chromatography, using MeOH:CHCl$_3$ (4:96) as eluent, to give the product as a clear, colourless oil, which solidified to a white foam after trituration and coevaporation with diethyl ether (0.288 g, 0.5 mmol, 69%).
$\delta_P$ (CDCl$_3$, 121 M) 3.84, 3.88; $\delta_H$ (CDCl$_3$, 300 M) 0.64 (m, 2H, CH$_2$-CPr), 0.87 (m, 2H, CH$_2$CPr), 1.24 [m, 2H, CH(CH$_3$)$_2$], 1.40 (t, 3H, CH$_3$-ala), 1.60 [m, 3H, CH(Cl$_3$)CH$_3$], 1.73 [m, 3H, CH(CH$_3$)CH$_3$], 2.19 (m, 1H, 6'H$_b$), 2.80 (m, 1H, $^{6'}$H$_b$), 3.03 (m, 1H, CHCPr), 3.18 (m, 1H, 4'H), 3.88 (m, 1H, CH-ala), 4.03 (m, 3H, OCH$_2$— and NH—ala), 4.21 (m, 2H, 5'H), 4.99 (bs, 2H, NH2), 5.55 (m, 1'H, 1'H), 5.91 (m, 2H, NH-cPr and 3$^1$H), 6.10 (m, 1H, 2$^1$H), 7.29 (m, 5H, ArH), 7.51 (d, 1H, 8H); $\delta_C$ $_{(CDCl3}$, 75 MHz) 7.79 (CH$_2$-cPr), 21.55 (CH$_3$-ala), 21.61 [CH(CH$_3$)$_2$], 23.69 (CH-cPr), 25.66 (O—CH$_2$CH$_2$CH$_2$—), 29.63 [CH(CH$_3$)$_2$], 35.00 (6'C), 38.81 (O-CH$_2$CH$_2$CH$_2$—), 46.01, 46.11 (4° C.), 50.72 (CH-ala), 59.21 (1'C), 69.31 (5'C), 69.85 (O-CH$_2$CH$_2$-), 115.25 (5C), 120.52–120.62 (p-Ph), 125.25 (o-Ph), 130.04 (m-Ph), 131.59 (3'C), 135.98 (8C), 136.71, 136.79 (2'C.), 151.08, 151.17 (6C and ipso-Ph), 156.70 (4C), 160.40 (2C), 174.00, 174.10 (C=O); m/z (FAB) 598.2883 (MH$^+$, C$_{29}$H$_{41}$N$_7$O$_5$P requires 598.2907).

L-Alanine (cyclopropyl methyl) ester hydrochloride salt

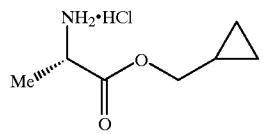

Thionyl chloride (1.2 ml, 0.017 M) was added dropwise to a stirred solution of cyclopropyl methanol (6.8 ml, 8.4 mmol) at 0° C. under nitrogen. The mixture was stirred for 30 minutes, then allowed to warm to room temperature. L-Alanine (pre-dried at 60° C. over P$_2$O$_5$ for 4 hrs: 0.75 g, 8.4 mmol) was added and the resulting suspension was heated at reflux overnight (the reaction mixture became a clear, colourless solution). The solvent was removed under reduced pressure to leave an orange/red oil which was repeatedly triturated and coevaporated with diethyl ether, to remove traces of cyclopropyl methanol. Diethyl ether (200 ml) was added and the mixture was stirred for 30 min. The resulting suspension was filtered to give the product as a cream solid (1.29 g, 7.1 mmol, 85%).

$\delta_H$(d$_4$-C:H$_3$OH, 300 MHz) 0.38 (m, 21, CH$_2$-cPr), 0.65 (m, 2H, CH$_2$-cPr), 1.24 (m, 1H, CH-cPr), 1.60 (d, 3H, CH$_3$-ala, J=7), 4.13 (m, 3H, CH-ala and O-CH$_2$); $\delta_C$ $_{(d4}$-CH$_3$OH, 75 MHz) 4.17 (CH$_2$-cPr), 10.98 (CH-cPr), 16.72 (CH$_3$-ala), 50.33 (CH-ala), 72.70 (O-CH$_2$), 171.56 (C=O).

Phenyl(cyclopropyl methoxy-L-alaninyl) phosphorochloridate

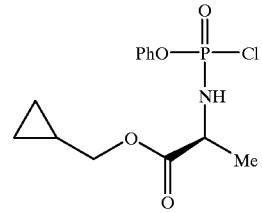

Prepared according to Standard Procedure 3, from phenyl dichlorophosphate (0.9 ml, 6.0 mmol), dry triethylamine (1.7 ml, 12.0 mmol), L-alanine (cyclopropyl methyl) ester p-toluene sulfonate salt 4a (1.082 g, 6.0 mmol) and dry DCM (100 ml total). The crude product was obtained as a clear, yellow oil (1.79 g, 94%).

$\delta_P$(CDCl$_3$, 121) 9.00, 9.36

The product was redissolved in dry THF (5 ml) and used as a 0.385 g/ml solution.

(1S,4R)-4(2-amino6-cyclopropylamino-9H-purin-9-yl)-2-cyclopeutene-1-methanol O-[phenyl(cyclopropyl methoxy-L-alaninyl)]phosphate

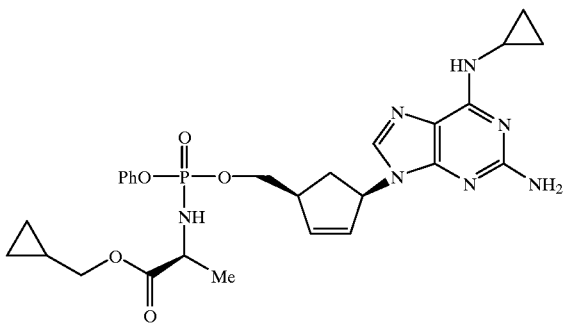

Prepared according to Standard Procedure 4, from (1S, 4R)-4-(2-amino6-cyclopropylamino-9H-purin-9-yl)-2-cyclopentene-1-methanol (0.2 g, 0.7 mmol), <sup>t</sup>BuMgCl (1.0M in THF: 1.4 ml, 1.4 mmol) phenyl(cyclopropyl methoxy-L-alaninyl) phosphorochloridate 4b (1.85 ml of 0.385 g/ml solution, 2.1 mmol) and dry THF (8 ml). TLC (8% MeOH in CHCl$_3$) showed the reaction to be complete after 3.5 hrs. The crude residue was purified twice by column chromatography, using MeOH:CHCl$_3$ (4:96) as eluent, to give the product as a clear, colourless oil which solidified to a white foam after trituration and coevaporation with diethyl ether (0.244 g, 0.4 mmol, 61%).

$\delta_P$ (CDCl$_3$, 121 MHz) 3.88, 3.94; $\delta_H$ (CDCl$_3$, 300 MHz) 0.29 (m, 2H, CH$_2$-cPr), 0.61 (m, 2H, CH$_2$-cPr), 0.87 (m, 2H, CH$_2$-cPr), 1.17 (m, 1H, CH-cPr), 1.42 (t, 3H, CH$_3$-ala), 1.69 (m, 1H, 6'H$_a$), 2.81 (m, 1H, 6'H$_b$), 3.04 (m, 1H, CH-cPr), 3.18 (m, 1H, 4'H), 4.01 (m, 4I, OCH$_2$—, CH-ala and NH-ala), 4.21 (m, 2H, 5$^1$H), 5.03 (bs, 2H, NH2), 5.56 (m, 1I, 1'H), 5.91 (m, 1H, 3$^1$H), 6.05 (bs, 1H, NH-cPr), 6.10 (m, 1H, 2$^1$H), 7.25 (m, 5H, ArH), 7.51 (d, 111H, 8H); $^5$c (CDCl$_3$, 75 MHz) 2.24 (CH$_2$-cPr), 6.33 (CH$_2$-cPr), 8.66 (CH$_2$-cPr), 20.05, 20.11 (CH$_3$-ala), 22.68 (CH-cPr), 33.55 (6'C), 44.58, 44.68 (4'C), 49.24, 49.31 (CH-ala), 57.77, 57.82 (1'C), 67.76, 67.93 (O-CH$_2$), 69.27, 69.29 (5'C), 113.74 (5C), 119.10–119.19 (p-Ph), 123.84 (o-Ph), 128.61 (m-Ph), 130.09, 130.13 (3'C), 134.42, 134.50 (8C), 135.32, 135.40 (2'C), 149.66, 149.74 (6C and ipso-Ph), 155.26 (4C), 159.00 (2C), 172.64, 172.73 (C=O).

L-Alanine (cyclobutyl methyl) ester hydrochloride salt

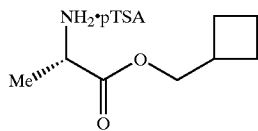

Prepared according to Standard Procedure 2, from L-alanine (1.6 g, 18 mmol), p-TSA monohydrate (3.8 g, 20 mmol), cyclobutane methanol (1.9 ml, 20 mmol) and toluene (100 ml). The p-toluene sulfonate salt was isolated as a white solid (4.249 g, 12.9 mmol, 72%).

$\delta_H$ (d$_4$-CH3OH, 300 MHz) 1.54 (d, 3H, CH$_3$-ala, J=7), 1.89 (m, 4H, cBu-2/4H), 2.08 (m, 2H, cBu-3H), 2.39 (s, 3H, CH$_3$, p-TSA), 2.69 9 m, 1H, CH-cBu), 4.11 (q, 11, CH-ala, J=7), 4.22 (m, 2H, O—CH$_2$), 7.26 (d, 2H, ArH, p-TSA), 7.73 (d, 2H, ArH, p-TSA); $\delta_C$ (d$_4$-CH$_3$OH, 75 MHz) 16.7 (CH$_3$-ala), 19.6 (CH$_2$-cBu), 21.7 (CH$_3$-pTSA), 25.9 (CH$_2$-cBu), 35.7 (CH-cBu), 48.9 (CH-ala), 71.3 (O—CH$_2$), 127.4 (o-Ph, p-TSA), 130.3 (m-Ph, p-TSA), 142.2 (ipso-C-CH$_3$,p-TSA), 143.8 (ipso-C-S, p-TSA), 171.6 (C=O).

Phenyl(cyclobutyl methoxy-L-alaninyl) phosphorochloridate

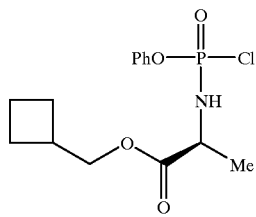

Prepared according to Standard Procedure 3, from phenyl dichlorophosphate (0.9 ml, 6.0 1 mmol), dry triethylamine (1.7 ml, 12.0 mmol), L-alanine (cyclobutyl methyl) ester p-toluene sulfonate salt 5a (1.98 g, 6.0 mmol) and dry DCM (100 ml total). The crude product was obtained as a clear, colourless oil (2.04 g, >100%).

$\delta_P$ (CDCl$_3$, 121 ) 9.00, 9.34

The product was redissolved in dry THF (5 ml) and used as a 0.408 g/ml solution.

(1S,4R)-4-(2-amino-6-cyclopropylamino-9H-purin-9-yl)-2-cyclopentene-1-methanol O-[phenyl(cyclobutyl methoxy-L-alaninyl)]phosphate [Cf 1773]

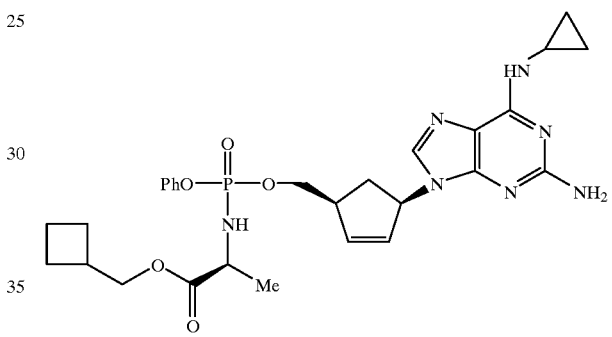

Prepared according to Standard Procedure 4, from (1S, 4R)-4-(2-amino-6-cyclopropylamino-9H-purin-9-yl)-$^2$-cyclopentene-1-methanol (0.2 g, 0.7 mmol), <sup>t</sup>BuMgCl (1.0M in TEF: 1.4 ml, 1.4 mmol) phenyl(cyclobutyl methoxy-L-alaninyl) phosphorochloridate 5b (1.7 ml of 0.408 g/ml solution, 2.1 mmol) and dry THF (8 ml). TLC (8% MeOH in CHCl$_3$) showed the reaction to be complete after 3 hrs. The crude residue was purified twice by column chromatography, using MeOH:CHCl$_3$ (4:96) as eluent, to give the product as a clear, colourless oil, which solidified to a white foam after trituration and coevaporation with diethyl ether (0.213 g, 0.4 mmol, 52%).

$\delta_P$ (CDCl$_3$, 121M ) 3.87, 3.91; $^3$H (CDCl$_3$, 300M ) 0.65 (m, 2H, CH$_2$cPr), 0.89 (m, 2H, CH$_2$-cPr), 1.41 (t, 3H, CH$_3$-ala), 1.74 (m, 3H, CH$_2$-cBu and 6$^1$H,), 2.06 (m, 2H, CH$_2$-cBu), 2.61 (m, 2H, CH$_2$-cBu), 2.81 (m, 1H, $^{61}$H$_b$), 3.04 (m, 1H, CH-cPr), 3.19 (m, 1H, 4'H), 3.90 (m, 1H, NH-ala), 4.09 (m, 3H, OCH$_2$—, and CH-ala), 4.22 (m, 2H, 5$^1$H), 4.98 (bs, 2H, NH$_2$), 5.56 (m, 1H, 1$^1$H), 5.92 (m, 2H, 3$^1$H and NH-cPr), 6.11 (m, 1H, 2'H), 7.26 (m, 5H, ArH), 7.52 (d, 1H, 8H); $\delta_C$ (CDCl$_3$, 75 MHz) 6.37 (CH$_2$-cPr), 17.33 (CH$_2$-cBu), 20.17, 20.23 (CH$_3$-ala), 22.68 (CH-cPr), 23.57 (2×CH$_2$-cBu), 32.86 (CH-cBu), 33.51, 33.55 (6'C), 44.58, 44.68 (4'C), 49.23, 49.28 (CH-ala), 57.81, 57.85 (1'C), 67.78–67.94 (5'C), 68.17, 68.20 (O-CH$_2$), 113.83 (5C), 119.09–119.19 p-Ph), 123.87 (o-Ph), 128.62 (m-Ph), 130.11, 130.15 (3'C), 134.51, 134.61 (8C), 135.30,135.39 (2'C), 149.64149.97 (6C and ipso-Ph), 155.20 (4C), 158.87 (2C), 172.64, 172.74 (C=O).

L-Alanine (cyclopentyl methyl) ester p-toluene sulfonate salt

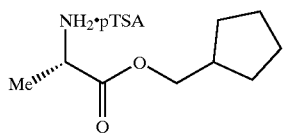

Prepared according to Standard Procedure 2, from L-alanine (1.6 g, 18 mmol), p-TSA monohydrate (3.8 g, 20 mmol), cyclopentane methanol (1.9 ml, 18 mmol) and toluene (100 ml). The p-toluene sulfonate salt was isolated as a white solid (6.21 g, 18 mmol, 100%). 5H ($d_4$-CH$_3$OH, 300 MH:) 1.22 (m, 2H, cPent 2/5H.), 1.46 (d, 3H, CH$_3$-ala), 1.56 (m, 4H, cPent 2/3/4/5H$_b$), 1.70 (m, 2H, cPent 3/4H.), 2.19 (m, 1'H, CH-cPent), 2.31 (s, 3H, CH$_3$, p-TSA), 4.06 (m, 3H, O-CH$_2$ and CH-ala), 7.18 (d, 2H, ArH, p-TSA), 7.64 (d, 2H, ArH, p-TSA);
67$\delta_C$ ($d_4$-CH$_3$OH, 75 MHz) 15.25 (CH$_3$-ala), 20.30 (CH$_3$, p-TSA), 25.27 (CH$_2$-cPent), 29.10, 29.15 (CH$_2$-cPent), 38.72 (CH-cPent), 48.84 (CH-ala), 70.12 (O-CH$_2$), 125.93 (o-Ph, p-TSA), 128.82 (m-Ph, p-TSA), 140.75 (ipso-C-CH$_3$, p-TSA), 142.40 (ipso-C-S, p-TSA), 170.09 (C=O).
Phenyl(cyclopentyl methoxy-L-alaninyl) phosphorochloridate

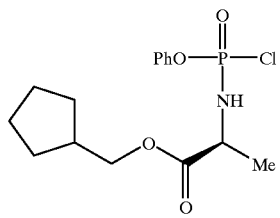

Prepared according to Standard Procedure 3, from phenyl dichlorophosphate (0.9 ml, 6.0 mmol), dry triethylamine (1.7 ml, 12.0 mmol), L-alanine (cyclopentane methyl) ester p-toluene sulfonate salt 6a (2.069 g, 6.0 mmol) and dry DCM (100 ml total). The crude product was obtained as a clear, yellow oil (1.97 g, 95%).
$\delta_P$ (CDCl$_3$, 121 M)8.94, 9.30

The product was redissolved in dry THF (IO ml) and used as a 0.197 g/ml solution.
(1S,4R)-4-(2-amino-6-cyclopropylamino-9H-purin-9-yl)-2-cyclopentene-1-methanol O-[phenyl(cyclopentyl methoxy-L-alaninyl)phosphate [Cf 1722]

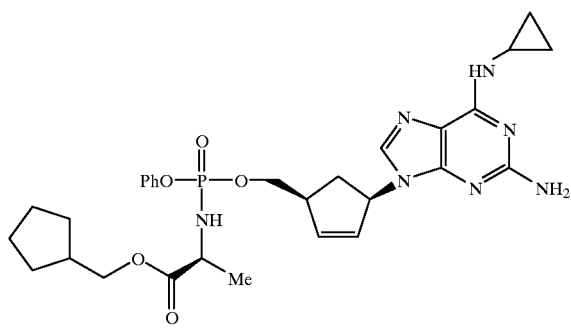

Prepared according to Standard Procedure 4, from (1S, 4R)-4-(2-amino-6-cyclopropylamino-9H-purin-9-yl)-2-cyclopentene-1-methanol (0.2 g, 0.7 mmol), $^t$BuMgCl (1.0M in THF: 1.4 ml, 1.4 mmol), phenyl (cyclopentene methoxy-L-alaninyl) phosphorochloridate 6b (3.7 ml of 0.197 g/ml solution, 2.1 mmol) and dry THF (10 ml). TLC (8% MeOH in CHCl$_3$) showed the reaction to be complete after 3 hrs. The crude residue was purified by column chromatography, using MeOH:CHCl$_3$ (4:96) as eluent, to give the product as a clear, colourless oil, which solidified to a white foam after trituration and coevaporation with diethyl ether (0.314 g, 0.5 mmol, 75%).
$\delta_P$ (CDCl$_3$, 121 MHz) 3.86, 3.87; 5H (CDCl$_3$, 300 MHz) 0.65 (m, 2H, CH$_2$-cPr), 0.89 [m, 8H, CH$_2$-cPr and (CH$_2$)3-cPent], 1.24 (m, 2H, CH$_2$-cPent), 1.41 (m, 311, CH$_3$-ala), 1.65 (m, 2H, CH-cPent and 6$^1$H.), 2.81 (m, 1H, 6'H$_b$), 3.04 (in, 1H, CH-cPr), 3.19 (m, 1H, 4$^1$H), 3.80 (in, 1H, CH-ala), 4.07 (m, 3H, OCH$_2$ and NH-ala), 4.22 (m, 2H, 5'H), 4.92 (bs, 2H, NH$_2$), 5.55 (m, 1H, 1'H), 5.81 (bs, 1H, NH-cPr), 5.92 (in, 1H, 3$^1$H), 6.11 (m, 1H, 2'H), 7.26 (m, 5H, ArH), 7.52 (d, 1H, 8H); $\delta_C$ (CDCl$_3$, 75 MHz) 6.42 (CH$_2$-cPr), 21.43 (CH$_3$-ala), 22.73 (CH-cPr), 24.59 (CH$_2$-cPent), 25.35 (CH$_2$-cPent), 26.64 (CH-cPent), 33.43, 33.51 (6'C), 44.58, 44.68 (4'C), 49.23 (CH-ala), 57.86, 57.91 (1'C), 64.69, 64.97 (O-CH$_2$—), 67.84 (5'C), 113.74 (5C), 119.09–119.18 (p-Ph), 123.88 (o-Ph), 128.62 (m-Ph), 130.05, 130.11 (3'C), 134.65, 134.76 (8C), 135.33, 135.44 (2'C), 149.63, 149.72 (6C and ipso-Ph), 154.98 (4C), 158.59 (2C), 172.50, 172.60 (C=O); nil/z (FAB) 598.2745 (MH$^+$, C$_{29}$H$_{39}$N$_7$O$_5$P requires 596.2750).

L-Alanine (cyclobutyl) ester p-toluene sulfonate salt

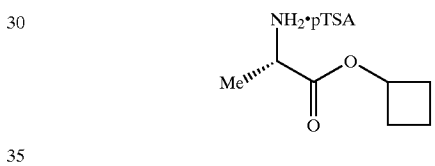

Prepared according to Standard Procedure 2, except using benzene as solvent: from L-alanine (1.0 g, 11 mmol),p-TSA monohydrate (2.35 g, 12 mmol), cyclobutanol (0.9 ml, 11 mmol) and benzene (65 ml). The p-toluene sulfonate salt was isolated as a white solid (1.73 g, 5.5 mmol, 49%). $^6$H ($d_4$-CH$_3$OH, 300 MHz) 1.51 (d, 3H, CH$_3$-ala, J =7), 1.75 (m, 2H, CH$_2$-cBu), 2.14 (m, 2H, CH$_2$-cBu), 2.37 (m, 5H, CH$_2$-c]u and CH$_3$, p-TSA), 4.05 (q, 1H, CH-ala, J=7), 5.08 (m, 1H, CH-cBu), 7.24 (d, 2H, ArH, p-TSA), 7.70 (d, 2H, ArH, p-TSA); $\delta_C$ ($_{d4}$-CH$_3$OH, 75 MHz) 14.57 (CH$_2$-cBu), 16.58 (CH$_3$-ala), 21.73 (CH$_3$-pTSA), 31.38, 31.44 (CH$_2$-cBu), 50.16 (CH-ala), 72.47 (CH-cBu), 127–35 (o-Ph, p-TSA), 130.23 (m-Ph, p-TSA), 142.13 (ipso-C-CH$_3$, p-TSA), 143.89 (ipso-C-S, p-TSA), 170.71 (C=O).
Phenyl(cyclobutoxy-L-alaninyl)phosphorochloridate

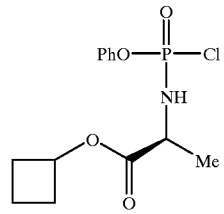

Prepared according to Standard Procedure 3, from phenyl dichlorophosphate (0.75 ml, 15.0 mmol), dry triethylamine (1.4 ml, 10.0 mmol), L-alanine (cyclopentane methyl) ester p-toluene sulfonate salt 7a (1.58 g, 5.0 mmol) and dry DCM (65 ml total). The crude product was obtained as a clear, colourless oil (1.13 g, 71%)

δ$_P$ (CDCl$_3$, 121 M)8.96, 9.33

The product was redissolved in dry THF (5 ml) and used as a 0.226 g/ml solution.

(1S,4R)-4-(2-amino-6-cyclopropylamino-911-purine-9-yl)-2-cyclopentene-1-methanol O[pheny](cyclobutoxy-L-alaninyl)]phosphate [Cf 1775]

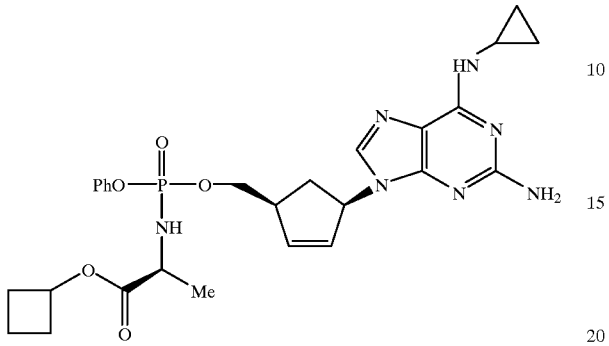

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(cyclobutyl methoxy-L-alaninyl) phosphorochloridate 7b (2.95 ml of 0.226 g/ml solution, 2.1 mmol) and dry THF (8 ml). TLC (8% MeOH in CHCl$_3$) showed the reaction to be complete after 3.5 hrs. The crude residue was purified by column chromatography, using MeOH:CHCl$_3$ (4:96) as eluent, to give the product as a pale, yellow oil, which solidified to a cream solid after trituration and coevaporation with diethyl ether (0.238 g, 0.4 mmol, 60%).

δ$_P$ (CDCl$_3$, 121 MHz) 3.89, 3.93; δ$_H$ (CDCl$_3$, 300M ) 0.63 (m, 2H, CH$_2$-cPr), 0.87 (m, 2H, CH$_2$-cPr), 1.39 (m, 3H, CH3-ala), 1.65 (m, 2H, CH$_2$-cBu), 1.81 (m, 1H, 6$^1$H,), 2.04 (m, 2H, CH$_2$-cBu), 2.36 (m, 2H, CH$_2$-cBu), 2.80 (m, 1H, 6'H$_b$), 3.03 (m, 1H, CH-cPr), 3.17 (m, 1H, 4'H), 3.97 (m, 2H, NH-ala and CH-ala), 4.18 (m, 2H, 5'H), 4.98 (m, 3H, NH$_2$ 42 and OCH), 5.55 (m, 1H, 1$^1$H), 5.91 (m, 1H, 3$^1$H), 6.01 (m, 1H, NH-cPr), 6.10 (m, 1H, 2'H), 7.25 (m, 5H, ArH), 7.51 (d, 1H, 8H); δ$_C$ (CDCl$_3$, 75 Mz) 7.80 (CH$_2$-cPr), 13.82 (CH$_2$-cBu), 21.42 (CH$_3$-ala), 22.06 (CH-cPr), 30.52–30.63 (CH$_2$-cBu), 35.01 (6'C), 46.01, 46.12 (4'C), 50.50 (CH-ala), 59.26 (1'C), 69.30 (CH-cBu), 70.19 (5'C), 115.25 (5C), 120.53, 120.59 (p-Ph), 125.28 (o-Ph), 130.05 (m-Ph), 131.53 (3'C), 135.97 (8C), 136.73, 136.85 (2'C), 151.08–151.17 (6C and ipso-Ph), 156.71 (4C), 160.44 (2C), 173.33 (C=O).

L-Alanine (cyclopentyl) ester p-toluene sulfonate salt

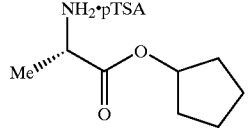

Prepared according to Standard Procedure 2, except using benzene as solvent: from L-alanine (1.6 g, 18 mmol), p-TSA monohydrate (3.8 g, 20 mmol), cyclopentanol (1.6 ml, 18 mmol) and benzene (100 ml). The p-toluene sulfonate salt was isolated as a beige solid (2.81 g, 8.5 mmol, 47%).

δ$_H$ (d$_4$-CH$_3$OH, 300M ) 1.51 (d, 3H, CH$_3$-ala, J=7), 1.71 (m, 6H, CH$_2$-cPnt), 1.92 (m, 2H, CH$_2$-cPnt), 2.39 (m. 5H, CH$_2$-cBu and CH$_3$,p-TSA), 4.04 (q, 1H, CH-ala, J=7), 5.28 (m, 1H, CH-cPnt), 7.26 (d, 2H, ArH, p-TSA), 7.73 (d, 2H, ATH, p-TSA); δ$_C$ (d$_4$-CH$_3$OH, 75 MHz) 16.59 (CH$_3$-ala), 21.72 (CH$_3$-pTSA), 24.97 (CH$_2$-cPnt), 33.81, 33.97 (CH$_2$-cPnt), 50.31 (CH-ala), 81.37 (CH-cPnt), 127.36 (o-Ph, p-TSA), 130.25 (m-Ph, p-TSA), 142.20 (ipso-C-CH$_3$, p-TSA), 143.79 (ipso-C-S, p-TSA), 171.17 (C=O).

Phenyl(cyclopentyloxy-L-alaninyl)phosphorochloridate

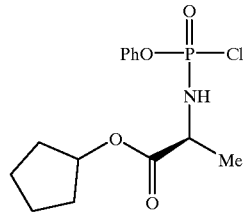

Prepared according to Standard Procedure 3, from phenyl dichlorophosphate (0.9 ml, 6.0 10 mmol), dry triethylamine (1.7 ml, 12.0 mmol), L-alanine (cyclopentane methyl) ester p-toluene sulfonate salt 8a (1.98 g, 6.0 mmol) and dry DCM (100 ml total). The crude product was obtained as a clear, colourless oil (1.8 g, 91%).

δ$_P$ (CDCl$_3$, 121 MHz) 9.01, 9.37

The product was redissolved in dry THF (5 ml) and used as a 0.361 g/ml solution. (1S,4R)-4-(2-amino-6-cyclopropylamino-9H-purin-9-yl)-2-cyclopentene-1-methanol O-[phenyl(cyclopentoxy-L-alaninyl)]phosphate [Cf 1776]

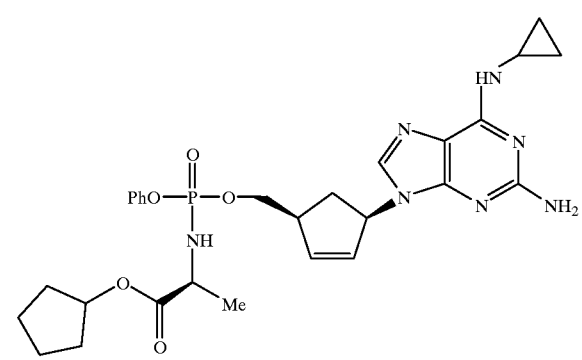

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(cyclobutyl methoxy-L-alaninyl) phosphorochloridate 8b (1.93 ml of 0.361 g/ml solution, 2.1 mmol) and dry THF (8 ml). TLC (8% MeOH in CHCl$_3$) showed the reaction to be complete after 3.5 hrs. The crude residue was purified twice by column chromatography, using MeOH:CHCl$_3$ (4:96) as eluent, to give the product as a clear, colourless oil, which solidified to a white foam after trituration and coevaporation with diethyl ether (0.254 g, 0.4 mmol, 62%).

δ$_P$ (CDCl$_3$, 121 MHz) 3.97, 3.98; SH (CDCl$_3$, 300 MHz) 0.64 (m, 2H, CH$_2$-cPr), 0.87 (m, 2H, CH$_2$-cPr), 1.38 (m, 3H, CH$_3$-ala), 1.67 (m, 7H, 3×CH$_2$-cPent and 6$^1$H.), 1.86 (m, 2H, CH$_2$-cPent), 2.81 (m, 1H, 6'H$_b$), 3.04 (m, 1H, CH-cPr), 3.18 (m, 1H, 4'H), 3.96 (m, 2H, Nil-ala and CH-ala), 4.21 (m, 2H, 5'H), 5.02 (bs, 1H, NH2), 5.18 (m, 1H, OCH), 5.56 (m, 1H, 1'H), 5.91 (m, 1H, 3$^1$H), 5.98 (bs, 1H, NH-cPr), 6.11 (m, 1H, 2'H), 7.25 (m, SH, ArH), 7.51 (d, 1H, 8H); δ$_C$ (CDCl$_3$, 75 MHz) 7.78 (CH$_2$-cPr), 21.42, 21.48 (CH$_3$-ala), 24.07 (CH-cPr), 32.91-(CH$_2$-cPent), 33.05, 33.08 (6'C), 34.97, 35.02 (CH$_2$-cPent), 46.02, 46.12 (4'C), 50.71 (CHala), 59.21, 59.25 (1'C), 69.22, 69.29 (5'C), 78.90 (OCH), 115.23 (5C), 120.55–120.61 (p-Ph), 125.28 (o-Ph), 130.05 (m-Ph), 131.53, 131.59 (3'C), 135.87, 135.97 (8C), 136.73, 136.86 (2'C), 151.09, 151.18 (6C and ipso-Ph), 156.71 (4C), 160.44 (2C), 173.71, 173.80 (C=O).

L-Alanine (phenethyl) ester p-toluene sulfonate salt

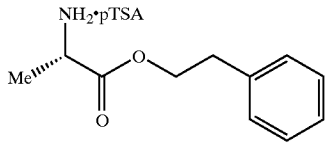

Prepared according to Standard Procedure 2, from L-alanine (1.0 g, 11 mmol), p-TSA monohydrate (2.35 g, 12 mmol), phenethyl alcohol (1.3 ml, 11 mmol) and toluene (65 ml). The p-toluene sulfonate salt was isolated as an off-white solid (4.0 g, 10.9 mmol, 97%).

$\delta_H$ (d$_4$-CH$_3$OH, 300 MHz) 1.46 (d, 3H, CH$_3$-ala, J=7), 2.32 (2, 3H, CH$_3$, p-TSA), 2.93 (t, 2H, CH$_2$Ph, J=7), 4.07 (q, 1H, CH-ala, J=7), 4.37 (m, 2H, 0-CH$_2$) 7.22 (m, 7H, ArH, p-TSA and PhH), 7.78 (d, 2H, ArH, p-TSA); $\delta_C$ $_{(d4}$-CH$_3$OH, 75 MHz) 16.80 (CH$_3$-ala), 22.06 (CH$_3$-pTSA), 36.20 (CH$_2$-Ph), 50.41 (CH-ala), 68.28 (O-CH$_2$), 127.70,127.83 (o-Ar and o-Ph,p-TSA), 129.81 (p-Ar), 130.13, 130.48 (m-Ar and m-Ph, p-TSA), 139.23 (ipso-ArC), 142.30 (ipso-C-CH$_3$, p-TSA), 143.83 (ipso-C-S, p-TSA), 171.44 (C=O).

Pheny(phenethoxy-L-alaninyl)phosphorochloridate

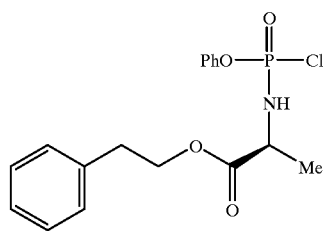

Prepared according to Standard Procedure 3, from phenyl dichlorophosphate (0.5 ml, 3.3 mmol), dry triethylamine (0.93 ml, 6.7 mmol), L-alanine (phenethyl) ester p-toluene sulfonate salt 9a (1.232 g, 3.3 mmol) and dry DCM (60 ml total). The crude product was obtained as a clear, colourless oil (1.16 g, 94%).

$\delta_P$ (CDCl$_3$, 121 MHz) 8.93, 9.25

The product was redissolved in dry THF (5 ml) and used as a 0.233 g/ml solution.

(1S,4R)-4-(2-amino-6-cyclopropylamino-9H-purin-9-yl)-2-cyclopentene-1-methanol O-[phenyl(phenethoxy-L-alaninyl)]phosphate [Cf 1777]

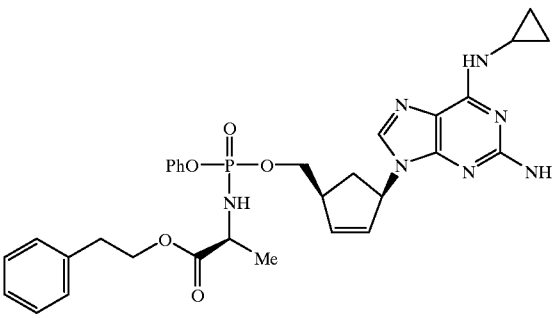

Prepared according to Standard Procedure 4, from (1S, 4R)-4(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(phenethoxy-L-alaninyl) phosphorochloridate 9b (3.3 ml of 0.233 g/ml solution, 2.1 mmol) and dry 1HF (8 ml). TLC (8% MeOH in CHCl$_3$) showed the reaction to be complete after 3 hrs. The crude residue was purified twice by column chromatography, using MeOH:CHCl$_3$ (4:96) as eluent, to give the product as a pale, yellow oil, which solidified to a cream solid after trituration and coevaporation with diethyl ether (0.181 g, 0.3 mmol, 42%).

$\delta_P$ (CDCl$_3$, 121 MHz) 3.81, 3.86; $\delta_H$ (CDCl$_3$, 300M ) 0.65 (m, 2H, CH$_2$CPr), 0.89 (m, 2H, CH$_2$-cPr), 1.35 (m, 3H, CH$_3$-ala), 1.71 (m, 1H, 6$^1$H,), 2.80 (m, 1H, $^{61}$H$_b$), 2.96 (m, 2H, CH$_2$Ph), 3.03 (m, 1H, CH-cPr), 3.17 (m, 1H, 4$^1$H), 3.91 (m, 2H, NH-ala and CH-ala), 4.18 (m, 2H, OCH), 4.36 (m, 2H, 5'H), 4.99 (bs, 1H, NH$_2$), 5.56 (m, 1H, 1'H), 5.92 (m, 2H, 3'H and NH-cPr), 6.09 (m, 1H, 2$^1$H), 7.26 (m, IOH, ArH and PhH), 7.52 (d, 1H, 8H); $\delta_C$ (CDCl$_3$, 75 MHz) 6.36 (CH$_2$-cPr), 19.98, 20.04 (CH$_3$-ala), 22.65 (CHcPr), 33.46, 33.54 (6'C), 33.90 (CH$_2$-Ph), 44.56, 44.66 (4'C), 49.21 (CH-ala), 57.79, 57.85 (1'C), 64.84 (OCH$_2$), 67,82 (5'C), 113.79 (5C), 119.11–119.17 (p-Ph), 123.87 (p-Ar), 125.68 (o-Ph), 127.53 (o-Ar), 127.83 (m-Ph), 128.62 (m-Ar), 130.07, 130.14 (3'C), 134.48 (8C), 135.30, 135.39 (2'C), 136.25 (ipso-Ar), 149.63, 149.71 (6C and ipso-Ph), 155.25 (4C), 158.94 (2C), 172.75, 172.45 (C=O).

L-Alanine (3-phenyl-1-propyl) ester p-toluene sulfonate salt

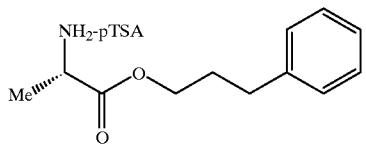

Prepared according to Standard Procedure 2, from L-alanine (1.0 g, 11 mmol), p-TSA monohydrate (2.35 g, 12 mmol), 3-phenyl-1-propanol (1.5 ml, 11 mmol) and toluene (65 ml). Removal of the solvent gave the crude product as a yellow oil. Diethyl ether was added and the mixture was cooled for 30 mins. The resulting suspension was filtered to give the p-toluene sulfonate salt as a white solid (4.24 g, 11.2 mmol, 100%).

$\delta_H$ (d$_4$-CH$_3$OH, 300 MHz) 1.53 (d, 3H, CH$_3$-ala, J =7), 1.97 (m, 2H, CH$_2$CH$_2$Ph), 2.34 (2, 3H, CH$_3$, p-TSA), 2.67 (t, 2H, CH$_2$Ph, J=7), 4.10 (q, 1H, CH-ala, J =7), 4.20 (t, 2H, O-CH$_2$, J=7) 7.22 (m, 7H, ArH, p-TSA and PhH), 7.75 (d, 2H, ArH, p-TSA); $\delta_C$ (d$_4$-CH$_3$OH, 75 Ma) 16.77 (CH$_3$-ala), 21.93 (CH$_3$-pTSA), 31.63 (CH$_2$CH$_2$-Ph), 33.37 (CH$_2$-Ph), 50.44 (CH-ala), 67.27 ()—CH$_2$), 127.26–127.58 (o-Ar and o-Ph, p-TSA), 129.66–130.00 (p-Ar), 130.41 (m-Ar and m-Ph, p-TSA), 142.31 (ipso-ArC), 142.82 (ipso-C-CH₃, p-TSA), 143.82 (ipso-C-S, p-TSA), 171.47 (C=O).

Phenyl(phenethoxy-L-alaninyl)phosphorochloridate

Prepared according to Standard Procedure 3, from phenyl dichlorophosphate (0.5 ml, 3.3 mmol), dry triethylamine (0.93 ml, 6.7 mmol), L-alanine (3-phenyl-1-propyl) ester p-toluene sulfonate salt 9a (1.27 g, 3.3 mmol) and dry DCM (60 ml total). The crude product was obtained as a clear, pale brown oil (1.16 g, 90%).

δ$_P$ (CDCl₃, 121 MHz) 8.94, 9.27

The product was redissolved in dry THF (5 ml) and used as a 0.231 g/ml solution.

(1S,4R)-4-(2-amino-6-cyclopropylamino-9H-purin-9-yl)-2-cyclopentene-1-methanol O-[phenyl(3-phenyl-1-propoxy-L-alaninyl)]phosphate [Cf 1778]

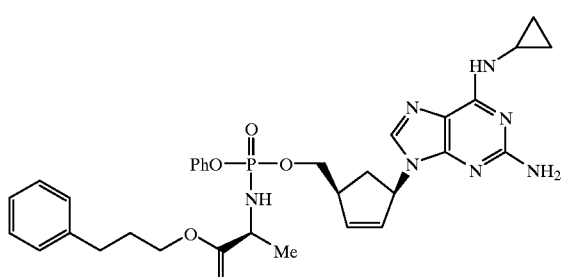

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(3-phenyl-1-propoxy-L-alaninyl) phosphorochloridate 10b (3.5 ml of 0.231 g/ml solution, 2.1 mmol) and dry THF (8 ml). TLC (8% MeOH in CHCl₃) showed the reaction to be complete after 4 hrs. The crude residue was purified three times by column chromatography, using MeOH:CHCl₃ (4:96) as eluent, to give the product as a pale, yellow oil, which solidified to an off-white foam after trituration and coevaporation with diethyl ether (0.330 g, 0.5 mmol, 75%). bp (CDCl₃, 121 MHz) 3.89, 3.91; δ$_H$ (CDCl₃, 300 MHz) 0.63 (m, 2H, CH₂-cPr), 0.88 (m, 2H, CH₂CPr), 1.42 (m, 3H, CH₃-ala), 1.72 (m, 1H, 6¹Ha), 1.98 (CH₂CH₂Ph), 2.69 (CH₂Ph), 2.80 (m, 1H, 6'H$_b$), 3.04 (m, 1H, CH-cPr), 3.18 (m, 1H, 4'H), 4.07 (m, 6H, NH-ala, CH-ala, OCH and 5'H), 5.00 (bs, 1H, NH₂), 5.56 (m, 1'H, 1'H), 5.91 (m, 2H, 3'H and NH-cPr), 6.10 (m, 1H, 2'H), 7.25 (m, 10H, ArH and Phi), 7.52 (d, 1H, 8H); δ$_C$ (CDCl₃, 75 MHz) 6.35 (CH₂-cPr), 20.06, 20.12 (CH₃-ala), 22.65 (CH-cPr), 29.02 (CH₂CH₂Ph), 30.97 (CH₂Ph), 33.48, 33.55 (6'C), 44.57, 44.67 (4'C), 49.26 (CH-ala), 57.78, 57.84 (1'C), 63.84 (OCH₂), 67.88 (5'C), 113.83 (5C), 119.10, 119.15 (p-Ph and p-Ar), 123.86 (oPh), 125.09 (o-Ar), 127.33, 127.47 (m-Ph), 128.63 (m-Ar), 130.10, 130.17 (3'C), 134.47, 134.58 (8C), 135.27, 135.37 (2'C), 139.81 (ipso-Ar), 149.65, 149.74 (6C and ipso-Ph), 155.27 (4C), 158.98 (2C), 172.49, 172.58 (C=O).

L-Alanine (4-phenyl-1-butyl) ester p-toluene sulfonate salt

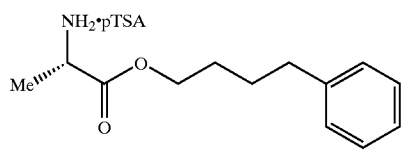

Prepared according to Standard Procedure 2, from L-alanine (1.0 g, 11 mmol), p-TSA monohydrate (2.35 g, 12 mmol), 4-phenyl-1-butanol (1.7 ml, 11 mmol) and toluene (65 ml). Removal of the solvent gave the crude product as a clear, colourless oil, which solidified to a white solid after trituration and coevaporation with petrol (60/80) (4.4 g, 11.2 mmol, 100%).

δ$_H$ (d₄-CH₃OH, 300 MHz) 1.55 (d, 3H, CH₃-ala, J=7), 1.74 (m, 4H, —(CH₂)₂CH₂Ph), 2.41 (2, 3H, CH₃,p-TSA), 2.67 (m, 2H, CH₂Ph), 4.12 (q, 1H, CH-ala, J=7), 4.28 (m, 2H, O-CH₂) 7.25 (m, 7H, ArK, p-TSA and PhH), 7.75 (d, 2H, ArR, p-TSA); δ$_C$ (d₄-CH₃OH, 75 MHz) 16.65 (CH₃-ala), 21.74 (CH₃-pTSA), 29.18, 29.50 (OCH₂(CH₂)₂CH₂-Ph), 36.72 (CH₂-Ph), 50.27 (CH-ala), 67.74 (O-CH₂), 127.31, 127.36 (o-Ar and o-Ph,p-TSA), 129.79 (p-Ar), 130.25 (m-Ar and m-Ph, p-TSA), 142.14 (ipso-ArC), 143.64, 143.87 (ipso-C-CH₃ and ipso-C-S, p-TSA), 171.47 (C=O).

Pheny)(4-phenyl-1-butoxy-L-alaninyl)phosphorochloridate

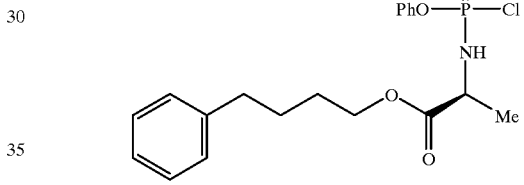

Prepared according to Standard Procedure 3, from phenyl dichlorophosphate (0.5 ml, 3.3 mmol), dry triethylamine (0.93 ml, 6.7 mmol), L-alanine (4-phenyl-1-butyl) ester p-toluene sulfonate salt 11a (1.32 g, 3.3 mmol) and dry DCM (60 ml total). The crude product was obtained as a clear, pale brown oil (1.13 g, 85%).

δ$_P$ (CDCl₃, 121 MHz) 8.89, 9.24

The product was redissolved in dry THEF (5 ml) and used as a 0.226 g/ml solution.

(1S,4R)-4-(2-amino-6-cyclopropylamino-9H-purin-9-yl)-2-cyclopentene-1-methanol O-[phenyl(4-phenyl-1-butoxy-L-alaninyl)]phosphate [Cf 11779]

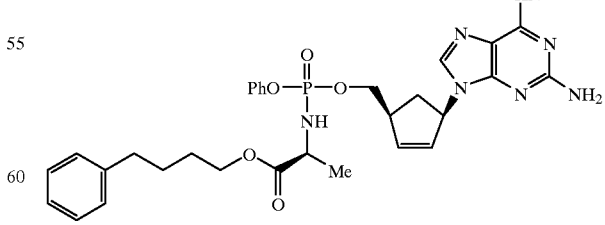

Prepared according to Standard Procedure 4, from (1S, 4R)-4-(2-amino-6-cyclopropylamino-9H-purin-9-yl)-²-cyclopentene-1-methanol (0.2 g, 0.7 mmol), 'BuMgCl (1.0M in THF: 1.4 ml, 1.4 mmol) phenyl(4-phenyl-1- butoxy-L-alaninyl) phosphorochloridate 11b (3.7 ml of 0.226 g/ml solution, 2.1 mmol) and dry THF (8 ml). TLC (8% MeOH in CHCl$_3$) showed the reaction to be complete after 4 hrs. The crude residue was purified by column chromatography, using MeOH:CHCl$_3$ (4:96) as eluent, to give the product as a clear, colourless oil, which solidified to an off-white foam after trituration and coevaporation with diethyl ether (0.314 g, 0.5 mmol, 69%).

$\delta_P$ (CDCl$_3$, 121 MHz) 3.87, 3.90; $\delta_H$ (CDCl$_3$, 300M ) 0.65 (m, 2H, CH$_2$-cPr), 0.87 (m, 2H, CH$_2$-cPr), 1.41 (m, 3H, CH$_3$-ala), 1.71 (m, SH, (CH$_2$)$_2$CH$_2$Ph and 6$^1$H$_a$), 2.65 (m, 2H, CH$_2$Ph), 2.80 (m, 1H, 6'H$_b$), 3.04 (m, 1H, CH-cPr), 3.17 (m, 1H, 4$^1$H), 4.06 (m, 6H, NH-ala, CH-ala, 5'H and OCH$_2$—) 5.02 (bs, 1H, NH$_2$), 5.56 (m, 1H, 1$^1$H), 5.90 (m, 11H, 3$^1$H), 5.98 (bs, 1H, NH-cPr), 6.10 (m, 1H, 2$^1$H), 7.25 (m, 10H, ArH and PhH), 7.52 (d, 1H, 8H); 8c (CDCl$_3$, 75 MHz) 6.35 (CH$_2$-cPr), 20.05. 20.11 (CH$_3$-ala), 22.65 (CHcPr), 26.51 (CH$_2$CH$_2$CH$_2$Ph), 27.02 (CH$_2$(CH$_2$)$_2$Ph), 33.48, 33.55 (6'C), 34.32 (CH$_2$Ph), 44.56, 44.67 (4'C), 49.22, 49.26 (CH-ala), 57.79, 57.83 (1'C), 64.40 (OCH$_2$), 67.86, 67.94 (5'C), 113.75 (5C), 119.10, 119.15 (p-Ph and p-Ar), 123.85 (o-Ph), 124.88 (o-Ar), 127.33, 127.35 (m-Ph), 128.61 (m-Ar), 130.07, 130.12 (3'C), 134.44, 134.54 (8C), 135.30, 135.39 (2'C), 140.76 (ipso-Ar), 149.64–149.87 (6C and ipso-Ph), 155.26 (4C), 158.98 (2C), 172.53, 172.63 (C=O).

L-Alanine (2-cyclohexyl ethyl) ester p-toluene sulfonate salt

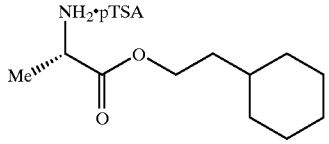

Prepared according to Standard Procedure 2, from L-alanine (1.0 g, 11 mmol), P-TSA monohydrate (2.35 g, 12 mmol), 2-cyclohexyl ethanol (1.56 ml, 11 mmol) and toluene (65 ml). Removal of the solvent gave the crude product as a clear, colourless oil, which solidified to a white solid after trituration and coevaporation with diethyl ether (2.8 g, 7.5 mmol, 67%).

$\delta_H$ (d$_4$-CH$_3$OH, 300 M) 0.97 (m, 2H, CH$_2$), 1.24 (m, 4H, 2×CH$_2$), 1.42 (m, 1H, CH-cHx), 1.54 (d, 3H, CH$_3$-ala, J =7), 1.63 (m, 2H, CHl], 1.75 (m, 4H, 2×CH$_2$), 2.39 (s, 3H, CH$_3$, p-TSA), 4.09 (q, 1H, CH-ala, J =7), 4.28 (m, 2H, O-CH$_2$), 7.25 (d, 2H, ArH, p-TSA), 7.72 (d, 2H, ArH, p-TSA); $\delta_C$ (d$_4$-CH$_3$OH, 75 MHz) 16.65 (CH$_3$-ala), 21.74 (CH$_3$-pTSA), 27.68 (CH$_2$), 27.93 (CH$_2$), 34.58 (CH$_2$), 34.62 (CH$_2$), 36.10 (CH-cHx), 50.27 (CH-ala), 66.05 [O—CH$_2$(CH$_2$)$_2$], 127.36 (o-Ph, p-TSA), 130.24 (m-Ph, p-TSA), 142.13 (ipso-C-CH$_3$, p-TSA), 143.89 (ipso-C-S, p-TSA), 171.49 (C=O).

Phenyl(2-cyclohexyl ethoxy-L-alaninyl) phosphorochloridate

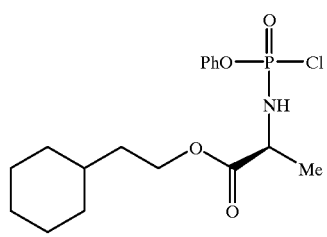

Prepared according to Standard Procedure 3, from phenyl dichlorophosphate (0.9 ml, 6.0 mmol), dry triethylamine (1.7 ml, 12.0 mmol), L-alanine (cyclohexyl ethyl) ester p-toluene sulfonate salt 12a (2.24 g, 6.0 mmol) and dry DCM (100 ml total). The crude product was obtained as a clear, colourless oil (1.86 g, 83%).

$\delta_P$ (CDCl$_3$, 121 MHz) 8.96, 9.31

The product was redissolved in dry IF (5 ml) and used as a 0.372 g/ml solution.

(1S,4R)-4-(2-amino-6-cyclopropylamino-9H-purin-9-yl)-2-cyclopentene-1-methanol O-[phenyl(2-cyclohexyl-1-ethoxy-L-alaninyl)]phosphate [Cf 1780]

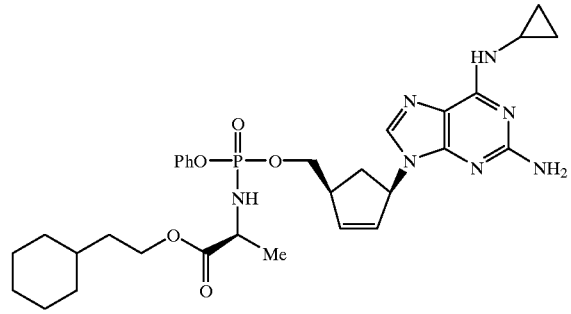

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(cyclohexyl ethoxy-L-alaninyl) phosphorochloridate 12b (2.1 ml of 0.372 g/ml solution, 2.1 mmol) and dry THF (8 ml). TLC (8% MeOH in CHCl$_3$) showed the reaction to be complete after 2.5 hrs. The crude residue was purified twice by column chromatography, using MeOH:CHCl$_3$ (4:96) as eluent, to give the product as a clear, colourless oil, which solidified to an off-white foam after trituration and coevaporation with diethyl ether (0.302 g, 0.5 mmol, 69%).

$\delta_P$ (CDCl$_3$, 121 MHz) 3.91, 3.94; SH (CDCl$_3$, 300 MHz) 0.64 (m, 2H, CH$_2$-cPr), 0.91 (m, 4H, CH$_2$ and CH$_2$-cPr), 1.21 (m, 2H, CH$_2$), 1.41 (m, 3H, CH$_3$-ala), 1.52 (m, 2H, CH-cHx and 6$^1$H$_a$), 1.70 (m, 6H, 3×CH$_2$), 2.80 (m, 1H, 6'H$_b$), 3.04 (m, 1H, CH-cPr), 3.18 (m, 1H, 4$^1$H), 4.10 (m, 6H, NH-ala, CH-ala, OCH$_2$ and 5$^1$H), 5.03 (bs, 1H, NH2), 5.56 (m, 1H, 1$^1$H), 5.96 (m, 1H, 3$^1$H), 5.98 (m, 1H, NH-cPr), 6.10 (m, 1H, 2$^1$H), 7.25 (m, 5H, Ar), 7.51 (d, 1H1, 8H); $\delta_C$ (CDCl$_3$, 75 MHz) 6–35 (Cl$_2$-cPr), 20.05, 20.12 (CH3-ala), 22.69 (CH-cPr), 25.11 (CH$_2$), 25.37 (CH$_2$), 32.04, 32.07 (6'C), 33.45, 33.58 (CHcHx), 34.76 (CH$_2$), 44.58, 44.69 (4'C), 49.28 (CH-ala), 57.78, 57.83 (1'C), 62.88 (OCH$_2$), 67.86 (5'C), 113.82 (5C), 119.10–119.19 (p-Ph), 123.85 (o-Ph), 128.61 (m-Ph), 130.12 (3∝C), 134.44, 134.54 (8C), 135.28, 135.38 (2'C), 149.66–149.94 (6C and ipso-Ph), 155.28 (4C), 155.99 (2C), 172.57, 172.66 (C=O).

L-Alanine (3-cyclohexyl-1-propyl) ester p-toluene sulfonate salt

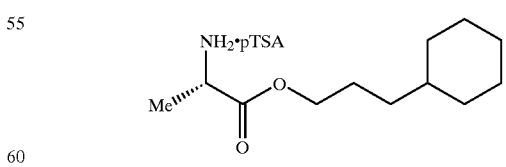

Prepared according to Standard Procedure 2, from L-alanine (1.0 g, 11 mmol), p-TSA monohydrate (2.35 g, 12 mmol), 3-cyclohexyl-1-propanol (1.7 ml, 11 mmol) and toluene (65 ml). The solvent was removed and diethyl ether was added. The resulting suspension was filtered to give the product as a white solid (3.9 g, 10.1 mmol, 90%).

$\delta_H$ (d$_4$-CH$_3$OH, 300 MHz) 0.92 (m, 2H, CH$_2$), 1.23 (m, 6H, 3×CH$_2$), 1.54 (d, 3H, CH$_3$-ala, J=7), 1.71 (m, 7H, CH-cHx and 3×CH$_2$), 2.39 (s, 3H, CH$_3$, p-TSA), 4.10 (q, 1H, CH-ala, J =7), 4.22 (m, 2H, O-CH$_2$), 7.25 (d, 2H, ArH, p-TSA), 7.72 (d, 2H, ArH, p-TSA); $\delta_C$ (d$_4$-CH$_3$OH, 75 Mz) 16.66 (CH$_3$-ala), 21.74 (CH$_3$-pTSA), 27.36 (CH$_2$), 27.83 (CH$_2$), 28.11 (CH$_2$), 34.80 (CH$_2$), 34.90 (CH$_2$), 39.03 (ICH-cHx), 50.27 (CH-ala), 68.27 (OCH$_2$), 127.36 (o-Ph, p-TSA), 130.24 (m-Ph, p-TSA), 142.12 (ipso-C-CH$_3$, p-TSA), 143.89 (ipso-C-S, p-TSA), 171.49 (C=O).

Phenyl(3-cyclobexyl-I-propoxy-L-alaninyl) phosphorochloridate

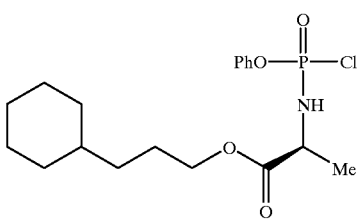

Prepared according to Standard Procedure 3, from phenyl dichlorophosphate (0.9 ml, 6.0 mmol), dry triethylamine (1.7 ml, 12.0 mmol), L-alanine (3-cyclohexyl-1-propyl) ester p-toluene sulfonate salt 13a (2.32 g, 6.0 mmol) and dry DCM (60 ml total). The crude product was obtained as a clear, pale yellow oil (2.31 g, 99%).

$\delta_P$ (CDCl$_3$, 121 MHz) 8.99, 9.35

The product was redissolved in dry THF (5 ml) and used as a 0.463 g/ml solution.

(1S,4R)-4-(2-amino-6-cyclopropylamino-9H-purin-9-yl)-2-cyclopentene-1-methanol O-[phenyl(3-cyclobexyl-]-propoxy-L-alaninyl)]phosphate [Cf 1781]

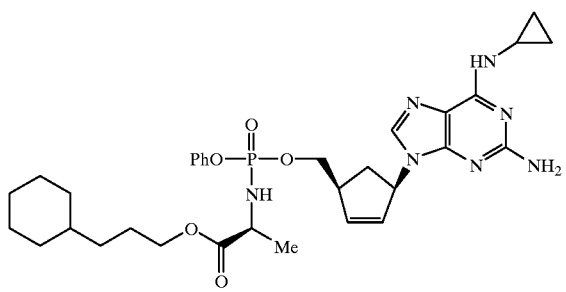

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol) phenyl(3-cyclohexyl-1-propoxy-L-alaniyl) phosphorochloridate 13b (1.8 ml of 0.463 g/ml solution, 2.1 mmol) and dry THF (8 ml). TLC (8% MeOH in CHCl$_3$) showed the reaction to be complete after 2.5 hrs. The crude residue was purified by column chromatography, using MeOH:CHCl$_3$ (4:96) as eluent, to give the product as a clear, colourless oil, which solidified to an off-white foam after trituration and coevaporation with diethyl ether (0.276 g, 0.4 mmol, 62%).

$\delta_P$ (CDCl$_3$, 121 MH) 3.89, 3.91; $\delta_H$ (CDCl$_3$, 300 Ma) 0.64 (m, 2H, CH$_2$cPr), 0.89 (m, 2H, CH$_2$-cPr), 1.21 (m, 6H, 3×CH$_2$), 1.41 (in, 3H, CH$_3$-ala), 1.66 (m, 8H, CH-cHx, 3×CH$_2$ and 6$^1$Ha), 2.81 (m, 1H, $^6$H$_b$), 3.04 (m, 1H, CH-cPr), 3.18 (in, 1H, 4$^1$H), 4.04 (m, 6H, NH-ala, CH-ala, OCH$_2$ and 5$^1$H), 4.98 (bs, 1H, NH2), 5.56 (in, 1H, 1$^1$H), 5.91 (m, 1H, 3$^1$H and NHI-cPr), 6.11 (m, 1H, 2$^1$H), 7.26 (m, 5H, Ar), 7.57 (d, 1H, 8H); $\delta_C$ $_{(CDCl_3}$, 75 M 6.37 (CH$_2$-cPr), 20.09, 20.15 (CH3-ala), 22.66 (CH-cPr), 24.85 (CH$_2$), 25.27 (CH$_2$), 25.55 (CH$_2$), 29.92 (CH$_2$), 32.20, 32.33 (6'C), 33.49, 33.57 (CH-cHx), 36.22 (CH$_2$), 44.58, 44.68 (4'C), 49.27 (CH-ala), 57.78, 57.83 (l'C), 65.01 (OCH$_2$), 67.84 (5'C), 113.86 (SC), 119.10–119.19 p-Ph), 123.85 (o-Ph), 128.61 (m-Ph), 130.12 (3'C), 134.47, 134.57 (8C), 135.28, 135.38 (2'C), 149.65–149.74 (6C and ipso-Ph), 155.27 (4C), 158.96 (2C), 172.53, 172.64 (C=O).

L-Alanine (4-cyclohexyl-1-butyl) ester p-toluene sulfonate salt

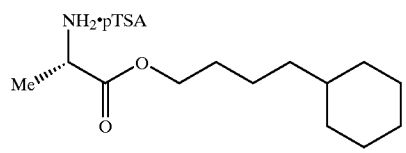

Prepared according to Standard Procedure 2, from L-alanine (0.51 g, 5.8 mmol), p-TSA monohydrate (1.21 g, 6.3 mmol), 4-cyclohexyl-1-butanol (1.0 ml, 5.8 mmol) and toluene (65 ml). The p-toluene sulfonate salt was obtained as a white crystalline solid (2.15 g, 5.4 mmol, 93%).

$\delta_H$ (d$_4$-CH$_3$OH, 300 MH) 0.92 (m, 2H, CH$_2$), 1.17 (m, 6H, 3×CH$_2$), 1.39 (m, 2H, Cl$_2$), 1.54 (d, 3H, CH$_3$-ala, J =7), 1.69 (m, 7H, CH-cHx and 3×CH$_2$), 2.39 (s, 3H, CH$_3$, p-TSA), 4.10 (q, 1H, CH-ala, J =7), 4.24 (m, 2H, O-CH$_2$), 7.25 (d, 2H, ArH, p-TSA), 7.72 (d, 2H, ArH, p-TSA); 8c (d$_4$-CH$_3$OH, 75 MHz) 16.66 (CH$_3$-ala), 21.74 (CH$_3$-pTSA), 24.51 (CH$_2$), 27.89 (CH$_2$), 28.18 (CH$_2$), 30.25 (CH$_2$), 34.90 (CH$_2$), 38.59 (CH$_2$), 39.27 (CH-cHx), 50.27 (CH-ala), 67.94 (OCH$_2$), 127.36 (o-Ph,p-TSA), 130.23 (m-Ph, p-TSA), 142.15 (ipso-C-CH$_3$, p-TSA), 143.89 (ipso-C-S, p-TSA), 171.49 (C=O).

Phenyl(4-cyclobexyl-1-butoxy-L-alaninyl) phosphorochloridate

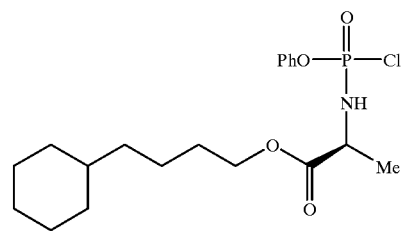

Prepared according to Standard Procedure 3, from phenyl dichlorophosphate (0.45 ml, 3.0 mmol), dry triethylamine (0.8 ml, 6.0 mmol), L-alanine (4-cyclohexyl-1-butyl) ester p-toluene sulfonate salt 14a (1.2 g, 3.0 mmol) and dry DCM (60 ml total). The crude product was obtained as a clear, brown oil (1.36 g, >100%).

$\delta_P$ (CDCl$_3$, 121 MHz) 8.91, 9.28

The product was redissolved in dry THF (5 ml) and used as a 0.272 g/ml solution.

(1S,4R)-4-(2-amino-6-cyclopropylamino-9H-purin-9-yl)-2-cyclopentene-1-methanol O-[phenyl(4-cyclohexyl-1-butoxy-L-alaninyl)]phosphate [Cf 1782]

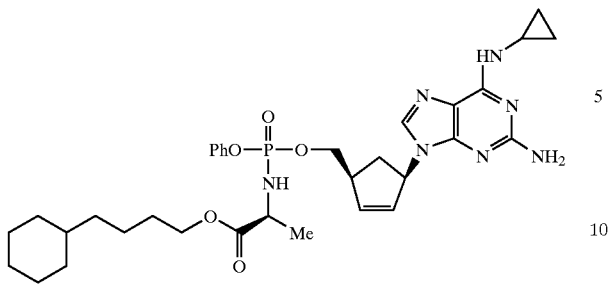

Prepared according to Standard Procedure 4, from (1S, 4R)-4-(2-amino-6-cyclopropylamino-9H-purin-9-yl)-2-cyclopentene-1-methanol 0.2 g, 0.7 mmol), 'BuMgCl (1.0M in THF: 1.4 ml, 1.4 mmol) phenyl(3-cyclo-hexyl-1-propoxy-L-alaninyl) phosphorochloridate 14b (3.1 ml of 0.272 g/ml solution, 2.1 mmol) and dry THF (8 ml). TLC (8% MeOH in CHCl$_3$) showed the reaction to be complete after 2.5 hrs. The crude residue was purified twice by column chromatography, using MeOH:CHCl$_3$ (4:96) as eluent, to give the product as a clear, colourless oil, which solidified to an off-white foam after trituration and coevaporation with diethyl ether (0.341 g, 0.5 mmol, 75%). 8p (CDCl$_3$, 121 MHz) 3.89, 3.91; $^8$H (CDCl$_3$, 300 MHz) 0.65 (m, 2H, CHz-cPr), 0.86 (m, 2H, CH$_2$-cPr), 1.21 (m, 8H, 4×CH$_2$), 1.41 (m, 3H, CH$_3$-ala), 1.65 (m, 8H, CH-cHx, 3×CH$_2$ and 6$^1$H$_b$), 2.81 (m, 1H, 6'H$_b$), 3.04 (m, 1H, CH-cPr), 3.19 (m, 1H, 4'H), 4.04 (m, 6H, NH-ala, CH-ala, OCH$_2$ and 5$^1$H), 4.96 (bs, 1H, NH$_2$), 5.56 (m, 1H, 1'H), 5.92 (m, 1H, 3'H and NH-cPr), 6.11 (m, 1H, 2$^1$H), 7.26 (m, 5H, Ar), 7.52 (d, 1H, 8H); $\delta_C$ (CDCl$_3$, 75 MHz) 6.37 (CH$_2$-cPr), 20.10, 20.16 (CH$_3$-ala), 22.00 (CH$_2$), 22.65 (CH-cPr), 25.34 (CH$_2$), 25.64 (CH$_2$), 27.77 (CH$_2$), 32.28 (CH-cHx), 33.48, 33.56 (6'C), 36.45 (CH$_2$), 44.58, 44.68 (4'C), 49.24 (CH-ala), 57.79, 57.84 (1'C), 64.69 (OCH$_2$), 67.84, 67.94 (5'C), 113.86 (5C), 119.10–119.19 p-Ph), 123.86 (o-Ph), 128.62 (m-Ph), 130.11,130.17 (3'C), 134.47,134.57 (8C), 135.28, 135.39 (2'C), 149.65–149.74 (6C and ipso-Ph), 155.26 (4C), 158.96 (2C), 172.54, 172.64 (C=O).

Phenyl(methoxy-L-valinyl)phosphorochloridate

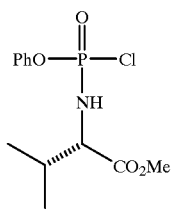

Prepared according to Standard Procedure 3, from phenyl dichlorophosphate (0.45 ml, 3.0 mmol), dry triethylamine (0.8 ml, 6.0 mmol), L-valine methyl ester hydrochloride salt (0.5 g, 3.0 mmol) and dry DCM (60 ml total). The crude product was obtained as a clear, colourless oil (0.922 g, >100%).

$\delta_P$ (CDCl$_3$, 121 MHz) 8.99, 9.37

The product was redissolved in dry TEF (5 ml) and used as a 0.184 g/ml solution.

(1S,4R)-4-(2-amino-6-cyclopropylamino-9H-purin-9-yl)-2-cyclopentene-1-methanol O-[phenyl(methoxy-L-valinyl) phosphate [Cf 1686]

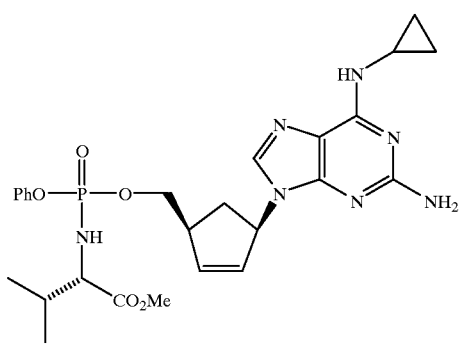

Prepared according to Standard Procedure 4, from (1S, 4R)-4-(2-amino-6-cyclopropylamino-9H-purin-9-yl)-2-cyclopentene-1-methanol (0.2 g, 0.7 mmol), 'BuMgCl (1.0M in THF: 1.4 ml, 1.4 mmol), phenyl(methoxy valinyl) phosphorochloridate 15a (3.5 ml of 0.184 g/ml solution, 2.1 mmol) and dry THF (5 ml). The reaction mixture was stirred for 16 hrs, after which time a further 1.5 ml of the solution of 15a was added. The reaction mixture was stirred for a further 4 hrs. The crude residue was purified by column chromatography, using MeOH:DCM (5:95) as eluent, to give the product as a clear, colourless oil, which solidified to a white foam after trituration and coevaporation with diethyl ether (0.161 g, 0.3 mmol, 41%).

$\delta_P$ (CDCl$_3$, 121 MHz) 4.65, 4.74; BH (CDCl$_3$, 300 MHz) 0.66 (m, 2H, CH$_2$-cPr), 0.94 [m, 8H, CH$_2$-cPr and CH(CH$_3$)$_2$], 1.71 (m, 1H, 6$^1$H.), 2.06 [m, 1H, CH(CH$_3$)$_2$], 2.81 (m, 1H, $^6$'H$_b$), 3.04 (m, 1H, CH-cPr), 3.18 (m, 1H, 4$^1$H), 3.52 (m, 1H, CH-val), 3.70 (d, 3H, OCH$_3$), 3.83 (m, 1H, NH-val), 4.22 (m, 2H, 5$^1$H), 4.86 (bs, 2H, NH$_2$), 5.56 (m, 1H, 1'H), 5.74 (bs, 1H, N1H-cPr), 5.93 (m, 1H, 3$^1$H), 6.11 (m, 1H, 2$^1$H), 7.27 (m, 5H, ArH), 7.52 (d, 1H, 8H); $\delta_C$ (CDCl$_3$, 75 MHz) 6.37 (CH$_2$-cPr), 16.36, 16.45 [CH(CH$_3$)$_2$], 22.65 (CH-cPr), 31.08, 31.16 [CH(CH$_3$)$_2$], 33.61 (6'C), 44.60, 44.70 (4'C), 51.05, 51.10 (OCH$_3$), 57.78 (1'C), 58.96, 59.01 (CH-val), 67.90 (5'C), 113.91 (5C), 119.03–119.13 (o-Ph), 123.80 (p-Ph), 128.58 (m-Ph), 130.05, 130.14 (3'C), 134.47 (8C), 135.27, 135.39 (2'C), 149.66–149.84 (6C and ipso-Ph), 155.28 (4C), 158.96 (2C), 172.10, 172.19 (C=O); m/z (FAB) 556.2428 (MH$^+$, C$_{26}$H$_{35}$N$_7$O$_5$P requires 556.2437).

Phenyl(methoxy-L-leucinyl)phosphorochloridate

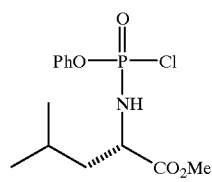

Prepared according to Standard Procedure 3, from phenyl dichlorophosphate (0.41 ml, 2.8 mmol), dry triethylamine (0.77 ml, 5.5 mmol), L-leucine methyl ester hydrochloride salt (0.5 g, 2.8 mmol) and dry DCM (60 ml total). The crude product was obtained as a clear, pale yellow oil (1.062 g, >100%).

$\delta_P$ (CDCl$_3$, 121 MHz) 9.33, 9.51

The product was redissolved in dry THF (5 ml) and used as a 0.212 g/ml solution.

(1S, 4R)-4-(2-amino-6-cyclopropylamino-9H-purin-9-yl)-2-cyclopentene-1-methanol O-[phenyl(methoxy-L-leucinyl) phosphate [Cf1718]

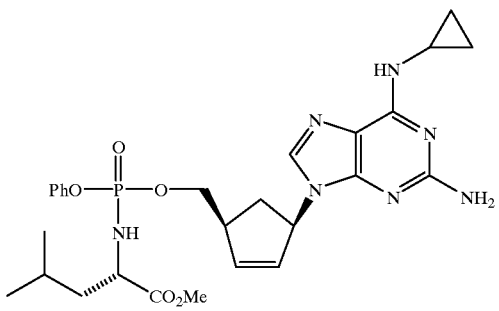

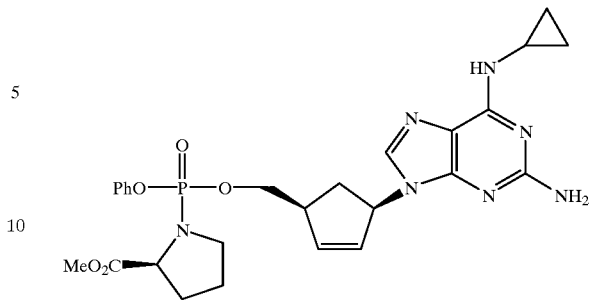

Prepared according to Standard Procedure 4, from (1S, 4R)-4-(2-amino-6-cyclopropylamino-9H-pun-9-yl)-2-cyclopentene-1-methanol 0.2 g, 0.7 mmol), 'BuMgCl (1.0M in THF: 1.4 ml, 1.4 mmol), phenyl (methoxy-L-leucinyl) phosphorochloridate 16a (3.2 ml of 0.212 g/ml solution, 2.1 mmol) and dry THF (10 ml). TLC (8% MeOH in CHCl$_3$) showed the reaction to be complete after 2 hrs. The crude residue was purified twice by column chromatography, using MeOH: CHCl$_3$ (4:96) as eluent, to give the product as a clear, colourless oil, which solidified to a white foam after trituration and coevaporation with diethyl ether (0.211 g, 0.4 mmol, 53%).

$\delta_P$ (CDCl$_3$, 121 MHz) 3.98, 4.06; 8H (CDCl$_3$, 300 MHz) 0.64 (m, 2H, CH$_2$CPr), 0.89 [m, 8H, CH$_2$-CPr and CH(CH$_3$)], 1.51 (m, 2H, CH$_2$leu), 1.69 [(m, 2H, CH(CH$_3$)$_2$ and 6'H$_a$], 2.80 (m, 1H,.6'H$_b$), 3.04 (m, 1H, CH-cPr), 3.16 (m, 1H, 4'H), 3.67 (m, 1H, CH-leu), 3.69 (d, 3H, OCH$_3$), 3.98 (m, 1H, NH-leu), 4.19 (m, 2H, 5$^1$H1), 4.97 (bs, 2H, NH$_2$), 5.55 (m, 1H, 1'H), 5.91 (m, 1H, NH-cPr and 3'H), 6.09 (m, 1H, 2'H), 7.25 (m, 5H, ArH), 7.51 (d, 1H, 8H); $\delta_C$ (CDCl$_3$, 75 Mz) 6.37 (CH$_2$Pr), 20.69, 20.82 (CH$_3$–1eu), 22.69 (CH-cPr), 23.28, 23.41 [CH(CH$_3$)$_2$], 33.54 (6'C), 42.6042.81 (CH$_2$-leu), 44.59,44.70 (4'C), 51.19, (OCH$_3$), 52.07, 52.16 (CH-leu), 57.80 (I° C), 67.91, 67.98 (5'C), 113.88 (5C), 118.99–119.14 (o-Ph), 123.80 (p-Ph), 128.58 (m-Ph), 130.06, 130.14 (3'C), 134.53 (8C), 135.27, 135.34 (2'C), 149.68–149.76 (6C and ipso-Ph), 155.28 (4C), 158.97 (2C), 173.12, 173.23 (C=O); m/z(FAB) 570.2610 (MH$^+$, C$_{27}$H$_{37}$N$_7$O$_5$P requires 570.2594).

Phenyl(methoxy-L-prolinyl)phosphorochloridate

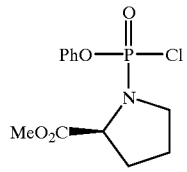

Prepared according to Standard Procedure 3, from phenyl dicllorophosphate (0.54 ml, 3.6 mmol), dry triethylamine (1.0 ml, 7.2 mmol), L-proline methyl ester hydrochloride salt (0.6 g, 3.6 mmol) and dry DCM (60 ml total). The crude product was obtained as a clear, colourless oil (1.24 g, >100%).

$\delta_P$ (CDCl$_{3,\ 121}$ MHz) 9.02, 9.22

The product was redissolved in dry THF (5 ml) and used as a 0.248 g/ml solution.

(1S4R4-(2-amino-6-cyclopropylamino-9H-purin-9-yl)-2-cyclopentene-1-methanol O-[pheny](methoxy-L-prolinyl) phosphate [Cf 1719]

Prepared according to Standard Procedure 4, from (1S, 4R)-4-(2-amino6-cyclopropylamino-9H-purin-9-yl)-2-cyclopentene-1-methanol (0.2 g, 0.7 mmol), 'BuMgCl (1.0M in TBT: 1.4 ml, 1.4 mmol), phenyl(methoxy-L-prolinyl) phosphorochloridate 17a (2.6 ml of 0.248 g/ml solution, 2.1 mmol) and dry THF (10 ml). TLC (8% MeOH in CHCl$_3$) showed the reaction to be complete after 20 hrs. The crude residue was purified twice by column chromatography, using MeOH: CHCl$_3$ (4:96) as eluent, to give the product as a clear, colourless oil, which solidified to a white foam after trituration and coevaporation with diethyl ether (0.168 g, 0.3 mmol, 44%). Bp (CDCl$_{3,\ 121}$ MHz) 2.83, 2.90; BH (CDCl$_3$, 300M ) 0.65 (m, 2H, CH$_2$-cPr), 0.90 (m, 2H, CH$_2$-cPr), 1.92 (m, 5H, CH$_2$CH$_2$-pro and 6'H$_b$), 2.83 (m, 1H, 6'H$_b$), 3.04 (m, 1H, CH-cPr), 3.17 (m, 1H, 4'H), 3.45 (m, 2H, N-CH$_2$-pro), 3.70 (d, 3H, OCH$_3$), 4.13 (m, 1H, CH-pro), 4.30 (m, 2H, 5$^1$H), 4.87 (bs, 2H, NH$_2$), 5.56 (m, 1H, 1$^1$H), 5.73 (s, 1H, NH-cPr), 5.91 (m, 1X, 3$^1$H), 6.12 (m, 1X, 2'H), 7.27 (m, 5H, ArH), 7.55 (d, 1H, 8H); $\delta_C$ (CDCl$_{3,\ 75}$ MHz) 6.42 (CH$_2$-cPr), 22.62 (CH-cPr), 23.91, 24.02 (CH$_2$-pro), 30.38, 30.49 (CH$_2$-pro), 33.54 (6'C), 44.61, 44.72 (4'C), 46.89 (N-CH$_2$), 51.07, 51.19 (OCH$_3$), 57.71, 57.80 (1'C), 58.84, 58.92 (CH-pro), 67.67, 67.75 (5'C), 113.87 (5C), 118.90–119.22 (o-Ph), 123.64, 123.73 (p-Ph), 128.55, 128.59 (m-Ph), 130.00 (3'C), 134.46 (8C), 135.42, 135.63 (2'C), 149.81, 149.90 (6C and ipso-Ph), 155.20 (4C), 158.87 (2C), 172.72, 173.23 (C=O); m/z (FAB) 554.2283 (MH$^+$, C$_{26}$H$_{33}$N$_7$O$_5$P requires 554.2281).

Phenyl(dibenzyloxy-L-aspartinyl)phosphorochloridate

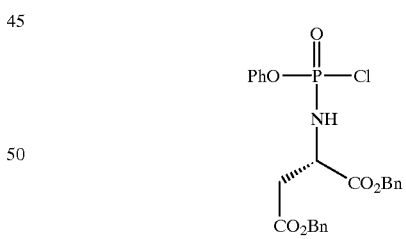

Prepared according to Standard Procedure 3, from phenyl dichlorophosphate (0.45 ml, 3.0 mmol), dry triethylamine (0.8 ml, 6.0 mmol), L-aspartate dibenzyl ester p-toluene sulfonate salt (1.46 g, 3.0 mmol) and dry DCM (60 ml total). The crude product was obtained as a clear, yellow oil (0.8024 g, 55%).

$\delta_P$ (CDCl$_3$, 121 M)9.43, 9.58

The product was redissolved in dry THF (5 ml) and used as a 0.16 g/ml solution.

(1S,4R)-4-(2-amino6-cyclopropylamino-9H-purin-9-yl)-2-cyclopentene-1-methanol O-[phenyl(dibenzyloxy-L-aspartinyl)phosphate [Cf 1720]

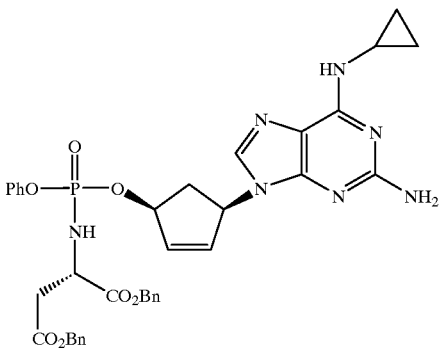

Prepared according to Standard Procedure 4, from (1S, 4R)-4-(2-amino-6-cyclopropylamino-9H-purin-9-yl)-2-cyclopentene-1-methanol (0.157 g, 0.55 mmol), 'BuMgCl (1.0M in THF: 1.1 ml, 1.1 mmol), phenyl(dibenzyloxy-1-aspartinyl) phosphorochloridate 18a (5.0 ml of 0.16 g/ml solution, 1.6 mmol) and dry THF (10 ml). TLC (8% MeOH in $CHCl_3$) showed the reaction to be complete after 1.5 hrs. The crude residue was purified twice by column chromatography, using MeOH: $CHCl_3$ (3:97) as eluent, to give the product as a clear, colourless oil, which solidified to an off-white foam after trituration and coevaporation with diethyl ether (0.284 g, 0.4 mmol, 70%). Sp ($CDCl_3$, 121 ) 3.68, 4.24; SH ($CDCl_3$, 300M ) 0.63 (in, 2H, $CH_2$-cPr), 0.85 (m, 2H, $CH_2$Pr), 1.63 (m, 1H, $6^1H$.), 2.71 (m, 1H, $6'H_b$), 3.06 (m, 2H, CH-cPr and 4'H), 4.14 (m, 2H, CH-asp, NH-asp), 4.34 (m, 2H, 5'H), 4.98 (bs, 2H, NH2), 5.06 (d, 2H, $OCH_2Ph$), 5.13 (d, 2H, $OCH_2Ph$), 5.53 (m, 1H, 1'H), 5.88 (in, 2H, NH-cPr and $3^1H$), 6.01 (m, 1H, 2'H), 7.25 (m, 1H, ArH), 7.49 (d, 1H, 8H); $\delta_C$ ($CDCl_3$, 75 MHz) 6.35 ($CH_2$-cPr), 22.64 (CH-cPr), 33.40 (6'C), 37.44, 37.60 ($CH_2$-asp), 44.50, 44.57 (4'C), 50.20, 50.33 (CH-asp), 57.79 (1'C), 65.77 ($OCH_2Ph$), 66.65 ($OCH_2Ph$), 67.86, 68.00 (5'C), 113.85 (5C), 119.09–119.34 (o-Ph), 123.92 (p-Ph), 127.34–127.55 (m-Ph and nap-Bn), 128.61 (o-Bn), 130.06 (3'C), 134.00 (ipso-Bn), 134.03 (ipso-Bn), 134.61 (8C), 135.23, 135.27 (2'C), 149.47–149.91 (6C and ipso-Ph), 155.28 (4C), 158.95 (2C), 169.22, 169.43, 170.00, 17029 (C=O).

(1S,4R)-4-(2-:amino-6-cyclopropylamino-9H-purin-9-yl-2-cyclopentene-1-methanol O-(phenyl (2-methylpropyl) oxyalaninyl phosphate) CF1672

This was prepared by Standard Procedure 4.70% yield. $\delta_P$ 3.87, 3.91.

$\delta_H$ 0.64 (2H, m, $CH_aH_b$, $CH_1$, $H_b$, cyclopropyl), 0.92 (8H, m, $CH_a$, $H_b$, $CH_a$, $H_b$, cyclopropyl, $CH(CH_3)_2$), 1.42 (3H, m, $CH_3$ alaninyl), 1.71 (1H, m, $6'-H_aH_b$), 1.92 (1H, m, $CH(CH_3)_2$), 2.81 (1H, m, $6'-H_aH_b$), 3.03 (1H, m, $CH_2$ cyclopropyl), 3.19 (1H, m, 4'-H), 3.87 (3H, m, CH alaninyl, $CH_2CH(CH_3)_2$), 4.09 (1H, m, NH alaninyl), 4.20 (2H, m, 5'-H), 4.91 (2H, br s, NH2), 5.53 (1H, br m, 1'-H), 5.80 (1H, br s, NH-cyclopropyl), 5.92 (1H, m, 3'-H), 6.12 (1H, m, 2'-H), 7.31 (5H, in, Ph-H), 7.48 (1H, br d, 8H)

$\delta_C$ 5.45 ($CH_2$cyclopropyl×2), 17.01 ($CH(CH_3)_2$), 19.23, 19.29 (Me alaninyl), 21.74 (CH-cyclopropyl), 25.72 (CH (CH3)_2), 32.58, 32.64 (6'-C), 43.66, 43.76 (4'-C), 48.35 (CH alaninyl), 56.90 (1'-C), 66.88, 66.96, 67.03 (5'-C), 69.57, 69.60 ($CH_2CH(CH_3)_2$), 118.17, 118.20, 118.24, 118.27 (o-Ph, 5-C), 122.94 (p-Ph), 127.70 (m-Ph), 129.19, 129.24 (3'-C), 134.35, 134.45 (8-C, 2'-C), 148.81, 148.72 (i-Ph), 149.62, 149.76 (6-C), 154.34 (4-C), 158.91, 158.96 (2-C), 171.68, 171.58 (C(O) alaninyl).

MS m/e 570.2505 ($M^+$, $C_{27}H_{36}N_7O_5P$ requires 570.2515). HPLC $t_R$ 33.11 min (0% $CH_3CN$ (0 min), 80% $CH_3CN$ (35 min), 80% $CH_3CN$ (45 min), 0% $CH_3CN$ (55 min)).

(1S ,4R)-442-amino6-cyclopropylamino-9H-purin-9-y)-2-cyclopentene-1-methanol O-(phenyl (2,2-dimethylpropyl) oxyalaninyl phosphate) CF1673

This was prepared by Standard Procedure 4.94% yield. $\delta_P$ 3.88, 3.94.

$\delta_H$ 0.61 (2H, m, $CH_aH_b$, $CH_a$,$H_b$, cyclopropyl), 0.85 (2H, br m, $CH_aH_b$, $CH_a$, $H_b$, cyclopropyl), 0.91 (9H, s, $C(CH_3)_3$), 1.41 (3H, m, $CH_3$ alaninyl), 1.70 (1H, m, $6'-H_aH_b$), 2.78 (1H, m, $6'-H_aH_b$), 3.03 (1H, m, CH cyclopropyl), 3.18 (1H, m, 4'-H), 3.81 (3H, m, CH alaninyl, $CH_2CH(CH_3)_2$), 4.09 (1H, m, NH alaninyl), 4.20 (2H, m, 5'-H), 4.97 (2H, br s, $NH_2$), 5.52 (1H, br m, 1'-H), 5.86 (1H, br s, NH-cyclopropyl, 3'-H), 6.08 (1H, m, 2'-H), 7.25 (5H, m, Ph-H), 7.48 (1H, br d, 8H).

$\delta_C$ 7.89 ($CH_2$-cyclopropyl×2), 21.74, 21.77 (Me alaninyl), 26.81 ($C(CH_3)_3$), 24.21 (CH-cyclopropy), 31.90 ($C(CH_3)_3$), 35.06 (6'-C), 46.10, 46.20 (4'-C), 50.79, 50.83 (CH alaninyl), 59–42 (1'-C), 66.35 (5'-C), 69.34, 69.41, 69.49 ($CH_2C(CH_3)_3$), 116.41 (5-C), 120.62,120.66, 120.68, 120.72 (o-Ph), 125.39 (p-Ph), 130.15 (7n-Ph), 131.61, 131.65 (3'-C), 136.82, 136.90 (8-C, 2'-C), 151.16, 151.25 (6-C, i-Ph), 156.78 (4-C), 158.91, 160.44 (2-C), 174.09, 174.20 (C(O) alaninyl).

$ES^+$m/e 584.2640 ($MH^+$, $C_{28}H_{39}N_7O_5P$ requires 584.2672). HPLC $t_R$ 34.97 min (0% $CH_3CN$ (0 min), 80% $CH_3CN$ (35 min), 80% $CH_3CN$ (45 min), 0% $CH_3CN$ (55 min)).

(1S,4R)-4-(2-amino-6-cyclopropylamino-9H-purin-9-yl)-2-cyclopentene-1-methanol O-(phenyl (3-methylbutyl) oxyalaninyl phosphate) CF1674

This was prepared by Standard Procedure 4.47% yield. $\delta_P$ 3.87, 3.89:

$\delta_H$ 0.57 (2H, m, $CH_aH_b$, $CH_a$,$H_b$ cyclopropyl), 0.80 (8H, m, $CH_aH_b$, $CH_a$, $H_b$, cyclopropyl, $CH(CH_3)_2$ ), 1.30 (3H, m, $CH_3$ alaninyl), 1.42 (2H, m, $OCH_2CH_2$), 1.62 (2H, m, $6'-H_aH_b$, $CH(CH_3)_2$), 2.70 (1H, m, $6'-H_3H_b$), 2.92 (1H, br s, CH cyclopropyl), 3.07 (1H, m, 4'-H), 3.88 (3H, m, CH alaninyl, $OCH_2CH_2$), 4.07 (3H, m, NE alaninyl, 5'-H), 4.91 (2H, br s, $NH_2$), 5.48 (1H, br m, 1'-H), 5.83 (2H, br s, NH-cyclopropyl, 3'-H), 6.03 (1H, m, 2'-H3, 7.18 (5H, m, Ph-H), 7.42 (1H, br d, 8H).

$\delta_C$ 7.81 ($CH_2$-cyclopropyl×2), 21.49, 21.56 (Me alaninyl), 22.79, 22.83 ($CH(CH_3)_2$), 24.10 ($CH(CH_3)_2$), 25.38 (CH-cyclopropyl), 34.91, 34.99 ($OCH_2CH_2$), 37.54 (6'-C), 46.01, 46.11 (4'-C), 50.70 (CH alaninyl), 59.25, 59.29 (1'-C), 64.63, 64.66 ($OCH_2CH_2$), 69.22, 69.30, 69.38 (5'-C), 116.17 (5-C), 120.53, 120.55, 120.59, 120.61 (o-Ph), 125.28 (p-Ph), 130.05 (m-Ph), 131.54, 131.60 (3'-C), 135.96 (8-C), 136.70, 136.81 (2'-C), 151.09, 151.17 (6-C, i-Ph), 156.68 (4-C), 160.34 (2-C), 173.94, 174.05 (C(O) alaninyl).

ES+m/e 584.2664 ($MH^+$, $C_{28}H_{39}N_7O_5P$ requires 584.2672). HPLC $t_R$ 38.51 min (0% $CH_3CN$ (0 min), 80% CH3CN (35 min), 80% $CH_3CN$ (45 min), 0% $CH_3CN$ (55 min)).

(1S,4R)-4-(2-amino-6-cyclopropylamino-9-H-purin-9-yl)2-cyclopentene-1-methanol O-(phenyl (cycloheptanyl) oxyalaninyl phosphate) CF1752

This was prepared by Standard Procedure 4.41% yield. $\delta_P$ 3.96, 3.98.

$\delta_H$ 0.68 (2H, m, $CH_aH_b$, $CH_a$,$H_b$, cyclopropyl), 0.99 (2H, m, $CH_aH_b$, $CH_a$, $H_b$, cyclopropyl), 1.36 (5H, m, $CH_3$ alaninyl, $5"-H_aH_b$,$6"-H_aH_b$), 1.80 (1 1H, m, $6'-H_aH_b$, 2"-H, 3"-H, 4"-H, 7"-H, $5"-H_aH_b$, $6"-H_aH_b$), 2.80 (1H, m, $6'-H_a,H_b$), 3.12 (1H, br s, CH cyclopropyl), 3.22 (1H, m, 4'-H), 3.97 (2H, m, CH alaninyl, NH alaninyl), 4.20 (2H, m, 5'-H), 4.95 (1H, m, O-CH), 5.18 (2H, br s, $NH_2$), 5.57 (1'H, br m, 1'-H), 5.90 (1H, m, 3'-H), 6.12 (1H, m, 2'-H), 6.25 (1'H, br s, NH cyclopropyl), 7.25 (5H, m, Ph-H), 7.51 (1H, br d, 8H).

$\delta_C$ 15.08 (CH$_2$-cyclopropyl×2), 28.76, 28.82 (Me alaninyl), 30.40, 30.44 (3"-C, 6"-C), 24.10 (CH(CH$_3$)$_2$), 31.57 (CH-cyclopropyl), 35.87 (4"-C, 5"-C), 41.26, 41.29, 41.31, 41.36 (6'-C), 42.24 (2"-C, 7"-C), 53.32, 53.42 (4'-C), 58.08 (CH alaninyl), 61.15 (1'-C), 66.62 (5'-C), 116.17 (5-C), 127.81, 127.85, 127.88, 127.91 (o-Ph), 132.54 (p-Ph), 137.32, 137.49 (m-Ph), 138.75 (3'-C), 143.21 (8-C), 144.13, 144.22 (2'-C), 158.40, 158.49 (6-C, i-Ph), 164.42 (4-C), 167.41 (2-C), 180.47, 180.51,180.59 (C(O) alaninyl).
ES+m/e 632.2719 (M[Na]$^+$, C$_{30}$H$_{40}$N$_7$O$_5$Nap requires 632.2726).
HPLC $t_R$ 41.92 min (0% CH$_3$CN (0 min), 80% CH$_3$CN (35 min), 80% CH$_3$CN (45 min), 0% CH$_3$CN (55 min)).
(1S,4R)-4-(2-amino-6-cyclopropylamino-9H-purin-9-yl)-2-cyclopeutene-1-methanol O-(phenyl diethoxy-L-aspartyl phosphate) CF1714
This was prepared by Standard Procedure 4.54% yield.
$\delta_P$ 3.76,4.19.
$\delta_H$ 0.62 (2H, m, CH$_a$H$_b$, CH$_a$,H$_b$, cyclopropyl), 0.88 (2H, m, CH$_a$H$_b$, CH$_a$, H$_b$, cyclopropyl), 1.25 (6H, m, CH$_3$—CH$_2$—O aspartyl×2), 1.68 (1H, m, 6'-H$_a$H$_b$), 2.75 (2H, m, —(CO)—CH$_a$H$_b$, aspartyl, 61-H$_a$H$_b$), 2.97 (2H, m, CH cyclopropyl, —(CO)-CH$_a$H$_b$ aspartyl), 3.16 (1H, m, 4'-H), 4.15 (8H, m, CH aspartyl, CH$_2$—O aspartyl×2, NH aspartyl, 5'-H), 4.90 (2H, br s, NH$_2$), 5.52 (1H, br m, 1'-H), 5.80 (1H, br s, NH-cyclopropyl), 5.90 (1H, m, 3'-H), 6.08 (1H, m, 2'-H), 7.21 (5H, m, Ph-H), 7.48 (1H, br d, 8H).
$\delta_C$ 8.65 (CH$_2$-cyclopropyl×2), 15.31 (CH$_3$-CH$_2$-O aspartyl× 2), 24.92 (CH-cyclopropyl), 35.72 ((CO)-CH$_2$ aspartyl), 39.74, 39.91 (6'-C), 46.82, 46.90 (4'-C), 52.41, 52.47 (CH aspartyl), 60.11 (1'-C), 62.22 (CH$_3$—CH$_2$—O(CO)CH$_2$ aspartyl), 63.15 (CH$_3$—CH$_2$—C(CO)CH 15 aspartyl), 70.14, 70.27, 70.35 (5'-C), 116.12 (5-C), 121.33, 121.40, 121.49, 121.55 (o-Ph), 126.15 p-Ph), 130.86 (m-Ph), 132.36 (3'-C), 136.90 (8-C), 137.54 (2'-C), 151.81, 151.85 (6-C, i-Ph), 157.39 (4-C), 161–01 (2-C), 171.67, 171.81 (C(O) CH$_2$ aspartyl), 172.38, 1172.48, 172.52, 172.62 (C(O) aspartyl).
ES+m/e 614.2393 (MH$^+$, C$_{28}$H$_{37}$N$_7$O$_7$P requires 614.2492).
HPLC IR 30.37 mn (0% CH$_3$CN (0 min), 80% CH$_3$CN (35 min), 80% CH$_3$CN (45 min), 0% CH$_3$CN (55 min)).
(1S,4R)-4-(2-amino-6-cyclopropylamino-9H-purin-9-yl)-2-cyclopentene-1-methanol O-(phenyl methoxy-L-methionyl phosphate) CF1715
This was prepared by Standard Procedure 4.49% yield.
$\delta_P$ 3.90, 4.03.
$\delta_H$ 0.61 (2H, m, CH$_a$H$_b$, CH$_a$, H$_b$, cyclopropyl), 0.86 (2H, m, CH$_a$H$_b$, CH$_a$,H$_b$, cyclopropyl), 1.71 (1H, m, CH-CH$_a$CH$_b$ methioninyl), 1.90 (1H, m, CH-C$_a$,CH$_b$ methioninyl), 2.01 (3H, d, CH$_3$—S—), 2.30 (1H, m, $^{6'}$-H$_a$H$_b$), 2.47 (2H, m, 5'-CH$_2$), 2.78 (1'H, m, $^{6'}$-H$_a$H$_b$), 2397 (1H, br m, CH cyclopropyl), 3.14 (1H, m, 4'-H), 3.70 (3H, d, CH$_3$—O—), 3.80 (1H, m, CH methioninyl) 4.17 (31H, m, NH methioninyl, 5'-H), 4.89 (2H, br s, NH2), 5.49 (1H, m1'-H), 5.80 (1H, br s, NH-cyclopropyl), 5.90 (1H, m, 3$^1$H), 6.08 (1H, ma, 2-H), 7.24 (5H, m, Ph-H), 7.43 (1H, br d, 8H).
$\delta_C$ 6.52 (CH$_2$-cyclopropyl×2), 14–42, 14.47 (CH$_3$—S-), 22.81 (CH-cyclopropyl), 28,63, 28.78 (S-CH$_2$), 32.62, 32.73,32.81 (CH-CH$_2$-methioninyl), 33.65 (67-C), 44.73, 44.83 (4'-C), 51.67 (CH methioninyl), 57.99 (1'-C), 68.13, 68.20,68.27 (5'-C), 114.03 (5-C), 119.15, 119.22, 119.24, 119.30 (o-Ph), 124.05, 124.10 (p-Ph), 128.80 (m-Ph), 130.26, 130.30 (3'-C), 134.72 (8-C), 135.42, 135.47 (2'-C), 149.76, 149.80, 149.84, 149.89 (i-Ph), 150.08 (6-C), 155.38 (4-C), 159.06 (2-C), 172.25, 172.28, 172.32, 172.36 (C(O)).
ES+m/e 588.2053 (0% C$_{26}$H$_{34}$N$_7$O$_5$PS requires 588.2080).

HPLC $t_R$ 29.64 min (0% CH$_3$CN (0 min), 80% CH$_3$CN (35 min), 80% CH$_3$CN (45 min), 0% CH3CN (55 min)).
(1S,4R)-4-(2-amino-6-cyclopropylamino-9H-purin-9-yl)-2cyclopentene-1-methanol O-(phenyl methoxy-L-tryptophanyl phosphate) CF1750
This was prepared by Standard Procedure 4.70% yield.
$\delta_P$ 3.88,4.01.
$\delta_H$ 0.68 (2H, m, CH$_a$H$_b$, CH$_a$,H$_b$ cyclopropyl), 0.92 (2H, m, CH$_a$H$_b$, CH$_a$, H$_b$,cyclopropyl), 1.53 (1H, m, 6'-H$_a$H$_b$), 2.68 (1H, m, 6'-H$_a$H$_b$), 2.99 (2H, br m, CH cyclopropyl, 4'-H), 3.22 (2H, m, CH$_2$-Trp), 3.66 (3H, d, CH$_3$-O-), 3.93 (3H, m, NH Tip, 5'-H), 4.35 (1H, m, CH Trp), 4.94 (2H, br s, NH2), 5.49 (1H, m, 1'-H), 5.87 (2H, m, NH-cyclopropyl, 3'-H), 5.97 (1H, m, 2'-H), 7.01 (1H, m, 6"-H), 7.26 (7H, m, Ph-H, 4"-H, 5"-H), 7.46 (1H, m, 7"-H), 7.52 (1H, m, 2"-H), 8.63 (1H, br d, 8H).
$\delta_C$ 7.81 (CH$_2$-cyclopropyl×2), 24.10 (CH-cyclopropyl), 34.86, 34.91 (6'-C), 45.81, 45.90, 46.00 (4'-C), 52.97 (CH Trp), 59.24, 59.29 (1'-C), 69.14, 69.20 (5'-C), 109.86, 110.11 (3"-C), 111.72 (7"-C), 118.91 (5-C), 119.95, 120.04 (4"-C, 5"-C), 120.40, 120.47, 120.57, 120.63 (o-Ph), 122.49, 122.56 (6"-H), 123.70 (2"-C), 125.23, 125.29 (P-Ph), 127.79, 127.98 (9"-C), 130.04 (m-Ph), 131.27 (3'-C), 136.08 (8-C), 136.50, 136.55, 136.76, 136.87 (2'-C, 8"-C), 151.05, 151.14, 151.17, 151.26 (i-Ph, 6-C), 156.68 (4-C), 160.35 (2-C), 173.58, 173.66 (C(O)).
ES+m/e 643.2432 (MH$^+$, C$_{32}$H$_{36}$N$_8$O$_5$P requires 643.2546).
HPLC $t_R$ 31.46 min (0% CH$_3$CN (0 min), 80% CH$_3$CN (35 mm), 80% CH$_3$CN (45 ), 0% CH$_3$CN (5 min)).
(1S,4R)-4-(2-amino-6-cyclpropylamino-9H purin-9-yl)-2-cyclopentene-1-methanol O-(phenyl methoxy-L-isoleucinyl phosphate) CF1751
This was prepared by Standard Procedure 4.60% yield. ps
$\delta_P$ 4.48, 4.54.
$\delta$0.68 (2H, m, CH$_a$H$_b$, CH$_a$, H$_b$,cyclopropyl), 0.91 (8H, m, CH$_a$, H$_b$, CH$_a$,H$_b$, cyclopropyl, CH$_3$×2 isoleucinyl), 1.15 (1H, m, CH$_a$CH$_b$ isoleucinyl), 1.45 (1H, m, CH$_a$CH$_b$ isoleucinyl), 1.75 (2H, m, 6'-H$_a$H$_b$, CH$_3$CH), 2.83 (JH, m, 6'-H$_a$H$_b$), 3.05 (1H, br m, CH cyclopropyl), 3.19 (1H, m, 4'-H), 3.62 (1H, m, NH isoleucinyl), 3.71 (3H, d, CH$_3$—O—), 3.88 (1H, m, CH isoleucinyl), 4.21 (2H, m, 5'-H), 4.91 (2H, br s, NH$_2$), 5.55 (1H, m, 1'-H), 5.81 (1H, br s, NH-cyclopropyl), 5.93 (1H, m, 3'-H), 6.12 (1H, m, 2'-H), 7.28 (5H, m, Ph-H), 7.52 (1H, br d, 8H).
$\delta_C$ 7.82 (CH$_2$-cyclopropyl×2), 11–89 (CH$_3$CH$_2$), 15.72 (CH$_3$CH), 24.08 (CH-cyclopropyl), 25.04, 25.13 (CH$_3$CH$_2$), 34.99 (6'-C), 39.49, 39.56, 39.64 (CH$_2$CH), 46.04, 46.14 (4'-C), 52.46, 52.50 (CH isoleucinyl), 59.24, 59.44, 59.54 (1'-C), 69.34 (5S-C), 116.12 (5-C), 120.47, 120.53, 120.58 (o-Ph), 125.27 (p-Ph), 130.03 (m-Ph), 131.50, 131.57 (3'-C), 136.04 (8-C), 136.84, 136.74 (2'-C), 151.10, 151.18, 151.27 (i-Ph, 6-C), 156.69 (4-C), 161.06, 161.09, 161.35, 161.41 (2-C), 173.48, 173.53 (C(O)).
ES+m/e 570.2496 (MH$^+$, C$_{27}$H$_{37}$N$_7$O$_5$P requires 570.2594).
HPLC IR 32.83, 33.14 min (0% CH$_3$CN (0 min), 80% CH$_3$CN (35 min), 80% CH$_3$CN (45 min), 0% Cl$_3$CN (55 min)).
(1S,4R)-4-(2-amino6-cyclopropylamino-9H-purin-9-yl)-2-cyclopentene-1-methanol O-(phenyl dimethoxy-L-glutamyl phosphate) CF1749
This was prepared by Standard Procedure 4.38% yield.
$\delta_P$ 3.99.
$\delta_H$ 0.68 (2H, m, CH$_a$H$_b$, CH$_a$,H$_b$, cyclopropyl), 0.91 (2H, m, CH$_a$H$_b$, C CH$_a$,H$_b$, cyclopropyl), 1.73 (1H, m, $^{6'}$-H$_a$, H$_b$), 2.12 (1H, m, C(O)CH$_2$CH$_a$H$_b$), 2.38 (2H, m, C(O)CH$_2$), 2.82 (1H, m, 6'-H$_a$H$_b$), 3.05 (1H, m, CH cyclopropyl), 3.18 (1H, n, 4'-H), 3.68 (3H, s, MeOC(O)CH$_2$), 3.72 (3H, s, MeOC(O)CH), 3.85 (1H, m, NH glutyl), 4.10 (1H, m, CH glutyl), 4.21 (2H, m, 5'-H), 4.95 (2H, br s, NH2), 5.57 (1H, br m, 1'-), 5.88 (1H, br s, NH-cyclopropyl), 5.95 (1H, m, 3'-H), 6.10 (1H, m, 2'-H), 7.25 (5H, m, Ph-H), 7.54 (1H, br s, 8H).

$\delta_C$ 7.82 ($CH_2$-cyclopropyl×2), 24.12 (CH-cyclopropyl), 29.66, 29.73, 29.88 (C(O)$CH_2CH_2$), C(O)$CH_2CH_2$), 34.91 (6'-C), 46.02, 46.12 (4'-C), 52.19 ($CH_3OC(O)CH_2CH_2$), 54.17, 54.28 ($CH_3OC(O)CH_2$), 54.17 (CH glutyl), 59.31 (1'-C), 69.50 (5'-C), 115.42 (5-C), 120.48, 120.51, 120.55, 120.58 (o-Ph), 125.39 (p-Ph), 130.09, 130.22 (m-Ph), 131.55, 131.60 (3'-C), 136.13 (8-C), 1136.68, 136.77 (2'-C), 150.98, 151.05, 151.13 (6-C), 151.76 (i-Ph), 156.65 (4-C), 160.99, 161.02, 161.08, 161.12 (2-C), 173.33, 173.43 (C(O)×2 glutyl).

ES+m/e 600.2216 (MH$^+$, $C_{27}H_{35}N_7O7P$ requires 600.2335).

HPLC tR 27.25 min (0% $CH_3CN$ (0 min), 80% $CH_3CN$ (35 min), 80% $CH_3CN$ (45 min), 0% $CH_3CN$ (55 min)).

(1S,4R)-4-(2-amino-6-cyclopropylamino-9H-purin-9-yl)-2-cyclopentene-1-methanol O-(phenyl (methoxy-α-ethyl-L-glycinyl phosphate) CF1783

This was prepared by Standard Procedure 4.44% yield.
$\delta_P$ 4.10.

$\delta_H$ 0.59 (2H, m, $CH_aH_b$, $CH_a$, $H_b$, cyclopropyl), 0.83 (5H, br m, $CH_aH_b$, $CH_aH_b$, cyclopropyl, $CH_3$-$CH_2$), 1.68 (3H, m, $CH_3$—$CH_2$, 6'-H.), 2.69 (1H, m, $^{6'}$-$H_aH_b$), 2.91 (1H, m, 4'-H), 3.06 (1H, m, CH cyclopropyl), 3.58 (3H, d, J 3.0, MeO), 3.90 (211, m, NH glycinyl, CH glycinyl), 4.07 (2H, m, 5'-H), 5.02 (2H, br s, NH2), 5.42 (1H, m, 1'-H), 5.75 (1H, m, 3'-H), 5.98 (1H, m, 2'-H), 6.03 (1H, m, NH cyclopropyl), 7.18 (5H, m, Ph-H), 7.41 (1H, br d, 8H).

$\delta_C$ 7.76 ($CH_2$-cyclopropyl×2), 9.68, 9.76 ($CH_3CH_2$), 24.12 (CH-cyclopropyl), 28.05 20 ($CH_3CH_2$), 35.01 (6'-C), 46.02, 46.13 (4'-C), 52.70, 52.73 ($CH_3O$), 56.02 (1'-C), 59.25 (CH-ala), 69.38 (5'-C), 116.10 (5-C), 120.48, 120.50, 120.55, 120.57 (o-Ph), 125.27 (p-Ph), 130.04 (m-Ph), 131.51 (3'-C), 135.86 (8-C), 136.86 (2'-C), 151.08, 151.13, 151.22 (6-C, i-Ph), 156.67 (4-C), 160.40 (2-C), 173.84, 173.87, 173.92 (C(O) alaninyl).

ES+m/e 564.2094 (M[Na]$^+$, $C_{25}H_{32}N_7O_5NaP$ requires 564.2100).

HPLC $t_R$ 16.82, 16.84 min (0% $CH_3CN$ (0 min), 80% $CH_3CN$ (15 mm), 80% $CH_3CN$ (25 min), 0% $CH_3CN$ (35 min)).

(1S S4R)-4-(2-amino-6-cyclopropylamino-9H-purin-9-yl)-2-cyclopentene-1-methanol O-(phenyl (methoxy-a-phenyl (RS)glycinyl phosphate) CF1784

This was prepared by Standard Procedure 4.46% yield.
$\delta_P$ 3.18,3.28,3.42,4.29.

Proton and Carbon NMR gave complex spectra, consistent with the racemised product.

ES+nm/e 612.2086 (M[Na$^+$, $C_{29}H_{32}N_7O_5NaP$ requires 612.2100).

HPLC $t_R$ 17.63, 18.50 min (0% $CH_3CN$ (0 min), 80% $CH_3CN$ (15 min), 80% $CH_3CN$ (25 min), 0% $CH_3CN$ (35 min)). (1:1.08 racemisation by HPLC)

(1S,4R)-4-(2-amino-6-cyclopropylamino-9H-purin-9-yl)-2-cyclopentene-1-methanol O-(phenyl (methoxy-α-butyl-L-glycinyl phosphate) CF1786

This was prepared by Standard Procedure 4.51% yield*.
Note: compound isolated as 6:1 (S:R) stereoisomeric mixture at the amino acid residue α-carbon. Additional resonances in the 31P NMR spectra are noted at 4.35 and 5.18, corresponding to the minor configuration (R) amino acid residue containing diastereoisomers.
$\delta_P$ 4.10, 4.16.

$\delta_H$ 0.51 (2H, m, $CH_a$, $H_b$, $CH_a$, $H_b$, cyclopropyl), 0.72 (5H, br m, $CH_aH_b$, $CH_a$, $H_b$. cyclopropyl, $CH_3$-$CH_2$), 1.18 (4H, m, $CH_3$-$CH_2$-$CH_2$-), 1.54 (3H, m, $CH_2$-$CH_2$-O, 6'-$H_aH_b$), 2.73 (1H, m, 6'-$H_aH_b$), 2.93 (111 m, 4'-H), 3.09 (]H, m, CH cyclopropyl), 3.52 (1H, m, CH glycinyl), 3.62 (3H, s, MeO), 3.87 (1H, m, NH glycinyl), 4.12 (2H, m, 5'-H), 4.75 (2H, br S, NH2), 5.45 (1H, m, 1'-H), 5.79 (2H, br s, NH-cyclopropyl, 3'-H), 6.00 (1H, m, 2'-H), 7.20 (5H, m, Ph-H), 7.42 (1H, br d, 8H).

$\delta_C$ 7.76 ($CH_2$-cyclopropyl×2), 14.23 ($CH_3CH_2$), 22.56 ($CH_3CH_2$), 24.14 (CH-cyclopropyl), 27.43, 27.50 ($CH_3CH_2CH_2$), 34.50, 34.58 ($CH_2CH_{2O}$), 35.01 (6'-C), 46.02, 46.12 (4-C), 52.66, 52.68 ($CH_3O$), 54.87, 54.94 (1'-C), 59.20 (CH-ala), 69.30, 69.37 (5'-C), 115.18 (5-C), 120.29, 120.42, 120.50, 120.57 (o-Ph), 125.21 ip-Ph), 130.00 (m-Ph), 131.51, 131.54 (3'-C), 135.86 (8-C), 136.71, 136.76 (2'-C), 151.12, 151.16, 151.20, 151.25 (6-C, i-Ph), 156.73 (4-C), 160.49, 160.96 (2-C), 174.19, 174.26 (C(O) glycinyl).

ES+m/e 592.2428 (M[Na]$^+$, $C_{27}H_3N_7O_5NaP$ requires 592–2413).

HPLC tR 18.34, 18.41, min and 16.64 min (6:1) (0% $CH_3CN$ (0 min), 80% $CH_3CN$ (35 min), 80% $CH_3CN$ (45 min), 0% $CH_3CN$ (55 min)).

(1S,4R)-4-2-amino6-cyclopropylamino-9H-purin-9-yl)-2-cyclopentene-1-methanol O-(phenyl (methoxy-α-propyl-L-glycinyl phosphate) CF1785

This was prepared by Standard Procedure 4.50% yield.
$\delta_P$ 4.14,4.21.

$\delta_H$ 0.62 (211, m, $CH_aH_b$, $CH_a$,$H_b$, cyclopropyl), 0.86 (5H3, br m, $CH_aH_b$, $CH_a$, $H_b$, cyclopropy], $CH_3$—$CH_2$), 1.32 (2H, m, $CH_3$-$CH_2$-), 1.63 (3H, m, $CH_3$-$CH_2$, 6'-$H_aH_b$), 2.79 (1H, m, 6'-$H_aH_b$), 3.03 (1H, m, 4'-H, 3.18 (1H, m, CH cyclopropyl), 3.71 (3H, d, J 3.0, MeO), 3.97 (1H, m, CH glycinyl), 4.15 (3H, m, 5'-H, NH glycinyl), 5.09 (2H, br s, NH$_2$), 5.55 (1H, m, 1'-H), 5.90 (1H, m, 3'-H), 6.08 (2H, m, 2'-H, NH cyclopropyl), 7.23 (5H, m, Ph-H), 7.52 (1H, br d, 8H).

$\delta_C$ 7.55 ($CH_2$-cyclopropyl×2), 13.98 (C1$H_3CH_2$), 18.62, 18.70 ($CH_3CH_2$), 24.15 (CH-cyclopropyl), 35.00 (6'-C), 36.89, 36.96 ($CH_2CH_2O$), 46.02, 46.12 (4'-C), 52.68 (CH3O), 54.70, 54.77 (1'-C), 59.21 (CH-ala), 69.38 (5'-C), 115.24 (5-C), 120.45, 120.51; 120.57 (o-Ph), 125.22 (p-Ph), 130.01 (m-Ph), 131.54 (3'-C), 135.89 (8-C), 136.72, 136.78 (2'-C), 151.11, 151.16, 151.20, 15125 (6-C, i-Ph), 156.72 (4-C), 160.45, 160.95 (2-C), 174.18, 174.25 (C(O) alaninyl).

ES+m/e 578.2259 (M[Na]$^+$, $C_{26}H_{34}N_7O_5NaP$ requires 578.2257).

HPLC tR 17.57 ml (0% $CH_3CN$ (0 min), 80% $CH_3CN$ (35 mL), 80% $CH_3CN$ (45 min), 0% $CH_3CN$ (55 ml)).

(1S,4R)-4-(2-amino6cyclopropyl-2 -amino-9H-purin-9-yl)-2-cyclopentene-1-methanol O-((P-(2 2-dimethoxy-L-propionic acid methyl ester)-phenyl)methoxyalaninyl phosphate) CF1671

This was prepared by Standard Procedure 4.24% yield.
$\delta_P$ 3.72, 3.84.

$\delta_H$ 0.56 (2H, m, $CH_a$, $H_b$, $CH_a$,$H_b$, cyclopropyl), 0.79 (2H, m, $CH_a$,$H_b$, $CH_a$, $H_b$, cyclopropyl), 1.30 (3H, m, $CH_3$ alaninyl), 1.63 (1H, m, 6'-$H_aH_b$), 2.70 (1H, m, 6'-$H_aH_b$), 2.95 (1H, br s, 4'-H), 3.07 (3H, m, CH cyclopropyl, Ph-$CH_2$-), 3.26 (6H, S, (OMe)$_2$), 3.52 (3H, s, C(OMe)$_2COOMe$), 3.61 (3H, s, COOMe alaninyl), 3.84–4.08 (4H, m, CH alaninyl, NH alaninyl, 5'-H), 4.99 (2H, br s, NH$_2$), 5.46 (1H, br m, 1'-H), 5.81 (1H, br s, 3'-H), 6.02 (2H, m,3'-H, NH-cyclopropyl), 6.02 (1H, m, 2'-H), 7.02 (4H, m, Ph-H), 7.45 (1H, br d, 8H).

$\delta_C$ 7.77 ($CH_2$cyclopropyl×2), 21.37 (Me alaninyl), 24.01 (CH-cyclopropyl), 34.89 (6'-C), 39.55 (Ph-$CH_2$), 45.97, 46.09 (4'-C), 50.53 ((MeO)$_2$, $CH_3OO$ alaninyl), 52.65

(C(OMe)₂COOMe), 59.28 (1'-C), 69.29 (5'-C), 103.27 (C(OMe)₂),120.31, 120.38 (o-Ph), 122.94 p-Ph), 131.35 (m-Ph), 131.39 (3'-C), 136.79 (8-C, 2'-C), 150.14,150.05 (i-Ph, 6-C), 152.12 (4-C), 160.24 (2-C), 169.08 (C(OMe)₂COOMC), 174.36, 174.46 (C(O) alaninyl).

ES+m/e 696.2531 ([M]⁺, C₃₀H₄₀N₇O₉NaP requires 696.2523).

HPLC IR 29.02 min (0% CH₃CN (0 min), 80% CH₃CN (35 min), 80% CH3CN (45 min), 0% CH₃CN (55 min)).

(1'S,4R)-4-(2-amino-6cyclopropylamino-9H-purin-9-yl)-2-cyclopentene-1-methanol O-((p-methoxyphenyl) methoxyalaninyl phosphate) CF1815

This was prepared by Standard Procedure 4.23% yield.

$\delta_P$ 4.23, 4.28.

$\delta_H$ 0.72 (2H, m, $CH_aH_b$, $CH_a,H_b$, cyclopropyl), 1.0 (2H, m, $CH_aH_b$, $CH_a$, $H_b$ cyclopropyl), 1.48 (3H, m, CH₃ alaninyl), 1.82 (1H, in, 6–1H$_a$H$_b$), 2.80 (1H, m, 6'-H$_a$H$_b$), 3.11 (1H, br s, 4'-H), 3.25 (1H, m, CH cyclopropyl), 3.67 (1H, m, NH alaninyl), 3.77 (3H, s, COOMe alaninyl), 3.89 (3H, s, MeO-Ar), 4.14 (1H, m, CH alaninyl), 4.30 (2H, m, 5'-H), 4.94 (2H, br S, NH₂), 5.65 (1H, br m, 1'-H), 5.83 (1H, br s, NH-cyclopropyl), 6.00 (1H, m, 3'-H), 6.17 (1H, m, 2'-H), 6.92 (2H, m, m-Ar), 7.23 (2H, m, o-Ar), 7.63 (1H, s, 8H).

$\delta_C$ 7.81 (CH₂-cyclopropyl×2), 21.46, 21.52 (Me alaninyl), 24.00 (CH-cyclopropyl), 34.96 (6'-C), 46.04, 46.14 (4'-C), 50.64 (CH300 alaninyl), 52.89 (CH-alaninyl), 56.02 (CH₃O-Ar), 59.28 (1'-C), 69.30 (5'-C), 114.98 (m-Ph, 5-C), 121.42, 121.46, 121.52 (o-Ph), 131.52, 131.56 (3'-C), 135.98, (2'-C), 136.76, 136.87 (i-Ph), 144.61 (8-C), 156.71 (4-C), 157.01 (p-Ar), 161.40, 160.99 (2-C), 174.39, 174.50 (C(O) alaninyl).

HPLC IR 16.28 (0% CH₃CN (0 min), 80% CH3CN (15 min), 80% CH₃CN (25 min), 0% CH₃CN (35 min)).

(1S,4R)-4-(2-amino-6-cyclopropylamino-9H-purin-9-yl)-2-cyclopentene-1-methanol O-((p-propoxyphenyl) methoxyalaninyl phosphate) CF1816

This was prepared by Standard Procedure 4.56% yield.

$\delta_P$ 4.33, 4.41.

$\delta_H$ 0.62 (2H, m, $CH_a,H_b$, $CH_a,H_b$, cyclopropyl), 0.82 (2H, m, $CH_aH_b$, $CH_a,H_b$, cyclopropyl), 1.03 (311, t, J 6.0, CH₃-CH₂), 1.39 (311, m, CH₃ alaninyl), 1.66 (1H, m, $^{6'}$-H$_a$H$_b$), 1.80 (2H, h, J 6.0, CH₃-CH9₂), 2.79 (1H, m, $^{6'}$-H$_a$H$_b$), 3.01 (1H, br s, 4'-H), 3.12 (1H, m, CH cyclopropyl), 3.72 (3H, s, COOMe alaninyl), 3.89 (2H, t, J 6.0, CH₂-O), 4.04 (2H1, m, CH alaninyl, NH alaninyl), 4.17 (211, m, 5'-H), 5.10 (21H, br s, NH2), 5.52 (1H, br m, 1'-H), 5.51 (1H, br s, NH-cyclopropyl), 5.89 (11H, m, 3'-H), 6.04 (1H, m, 2'-H), 6.81 (21 m, m-Ar), 7.11 (2H, m, o-Ar), 7.51 (1H, s, 8H).

$\delta_C$ 7.77 (CH₂-cyclopropyl×2), 10.91 (CH₃-CH₂), 21.39, 21.46 (Me alaninyl), 22.97 (CH₃-CH₂), 24.14 (CH-cyclopropyl), 34.96 (6'-C), 46.02, 46.13 (4'-C), 50.57, 50.65 (CH₃OO alaninyl), 52.85, 52.87 (CH-alaninyl), 53.89 0 59.25 (1'-C), 69.16, 69.24, 69.33 (5'-C), 70.30 (CH₂-O), 115.24,115.26 (5-C), 115.57 (m-Ph), 121.37, 121.40, 121.43,121.46 (o-Ph), 131.51, 131.57 (3'-C), 135.93, (2'-C), 136.77, 136.85 (i-Ph), 144.47, 144.55 (8-C), 156.54, 156.73 (4-C), 160.45 (p-Ar), 160.91 (2-C), 174.48, 174.59 (C(O) alaninyl).

HPLC $t_R$ min (0% CH₃CN (0 min), 80% CH₃CN (15 min), 80% CH3CN (25 min), 0% CH₃CN (35 min)).

(1S,4R)-4-(2-amino-6-cyclopropylamino-9H-purin-9-yl)-2-cyclopentene-1-methanol O-[4-hydroxyacetophenone (methoxy-L-alaninyl)]-phosphoramidate Cf 1794

This was prepared by Standard procedure 4. The crude residue was purified twice by column chromatography, using MeOH:CHCl₃ (3%:97) and MeOH:EtOAc (5:95) as eluent, to give the product as a white foam (30 mg, 17 mmol, 15%).

$\delta_P$ 3.496.

$\delta_{SH}$ 0.66 (m,2H,CH₂-cPr), 0.85 (m,2H,CH₂-cPr), 1.33 (m, 3H, CH3-CH), 1.7 (m, 1H, H'6), 2.53 (s, 3H, CH3-COPh), 2.8 (m, 1H, H'6), 2.9 (m, 1H, CH-cPr), 3.1 (m, 1H1, H'4), 3.6 (s, 3H, CH₃-O), 3.9 (m, 1H, CH3-CH), 4.1 (m, 2H, H'5), 4.9 (m, 2H, NH₂), 5.5 (m, 1H,'1), 5.85 (m, 1H, H'3), 6.1 (m, 2H, H'2,NHcPr) 7.2 (dd, 2H, o-Ar), 7.5 (m, 1H, H8), 7.8 (dd, 2H, p-Ar)

$\delta_C$ 6.371 (CH₂cPr), 20 (CH-CH₃aa), 21.671 (NHCH3), 25 (CH3CO), 33.458 (C'6), 44.55 (C'4),49.5 (CHaa), 51.4 (OCH3), 57.9 (C'1), 67.9 (C'5), 113.787 (C5), 120 (o-Ar), 122.22 (p-Ar), 128.743 (m-Ar), 130 (C'3), 134.53 (C'2), 135.31 (C8), 150.31 (i-Ar), 155.18 (C6), 156.342 (C2), 158.8 (C4), 173.004 (COOCH3), 198 (CO-Ar).

HPLC $t_r$: 15.976 min (0% CH₃CN (0 min), 80% CH₃CN (15 min), 80% CH₃CN (25 min), 0% CH₃CN (35 min)).

(1S,4R)-4-(2-amino-6cyclopropylamino-9H-purin-9-yl)-2-cyclopentene-1-methanol O-[4D-butylphenyl-(methoxy-L-alaninyl)-phosphate Cf 1795

The crude residue was purified twice by column chromatography, using MeOH:CHCl₃ (3%:97) and MeOH:CH₂Cl₂ (5:95) as eluent, to give the product as a white foam (15 mg, 0.025 mmol, 4%), $\delta_P$ 3.934.00.

$\delta_H$ 0.66 (m,2H,CH₂-cPr), 0.85 (m,2H,CH₂-cPr), 1.1 (m,3H, CH₃-CH₂),1.2 (m,4H, CH₂-CH₂), 1.33 (m, 3H, CH3-CH), 1.7 (m, 1H, H'6),2.5 (m, 2H, CH₂-Ar), 2.8 (m, 1H, H'6),2.9 (m, 1H, CH-cPr), 3.1 (m, 1H, H'4),3.6 (s, 3H, CH3-O),3.9 (m, 1H, CH3—CH), 4.1 (m, 2, H'5),4.9 (m, 2H, NH2),5.5 (m, 1H'1), 5.85 (m, 1H, H'3), 6.1 (m, 2H, H'2,NHcPr), 7.2

$\delta_C$ (dd, 211, o-Ar), 7.5 (m, 1H, H8),7.8 (dd, 2H,p-Ar). $^6c$ 6.371 (CH₂cPr), 14.345 (CH₃—CH₂), 21.49 (CH-CH3aa), 22.66 (CH₂-CH₃), 21.671 (NHCH3), 30.127 (CH₂-CH₂-CH12), 33.458 (C'6), 34.047.(CH₂-Ar), 44.55 (C'4), 49.5 (CHaa), 51.4 (OCH3), 57.9 (C'1), 67.9 (C'5), 113.787 (C5), 120 (o-Ar), 122.22 (p-Ar), 128.743 (m-A), 130 (C'3),134.53 (C2),135.31 (C8),146.58 (i-Ax) 155.18 (C6),156.342 (C2), 158.8 (C4),173.004 (COOCH)

HPLC $t_r$: 19.591 mn (0% CH₃CN (0 mm), 80% CH₃CN (15 inn), 80% CH₃CN (25 min), 0% CH₃CN (35 min)).

(1S,4R)-4i(2-amino6-cyclopropylamino-9H-purin-9-yl)-2-cyclopentene-1-methanol O-[phenylphenyl-(methoxy-L-alaninyl)]-phosphate Cf 1788

The crude residue was purified three times by column chromatography, using MeOH:CHCl₃ (3:97) and MeOH:CH₂Cl₂ (5:95) and MeOH:AcOEt (3:97) as eluent, to give the product as a yellow foam (35 mg, 0.058 mmol, 8%).

$\delta_P$ 3.94–3.96.

$\delta_H$ 0.66 (m,2H,CH2-cPr), 0.85 (m,2H,CH₂Pr), 1.33 (m, 3H, CH3—CH), 1.7 (m, 1H, H'6), 2.8 (m, 11H, H'6), 2.9 (m, 1H, CH-cPr), 3.25 (m, 1H, H'4), 3.6 (s, 3H, CH3-O), 4.1 (m, 1H, CH3-CH), 4.25 (m, 2H, H'5), 4.9 (m, 2H, N1H2), 5.5 (m, 1H,H'1), 5.85 (m, 1H, H'3), 6.15 (m, 2H, H'2,NHcPr), 7.35 (m, 9H, Ar), 7.6 (m, 1H, H8).

$\delta_C$ 6.371 (CH₂cPr), 21.49 (CH-CH3aa), 21.671 (NHCH3), 33.458 (C'6), 46.14 (C4), 50.671 (CHaa), 52.9 (OCH3),59.9 (C'1), 65.9 (C'5),115.787 (C5),120 (o-Ar), 122.22 (p-Ar), 128.743 (m-Ar), 130 (C'3), 134.53 (C'2), 135.31 (C8), 145.25 (i-Ar), 155.18 (C6), 156.342 (C2),158.8 (C4), 173.004 (COOCH3).

HPLC $t_r$: 19.147 min (0% CH₃CN (0 mn), 80% CH₃CN (15 min), 80% CH₃CN (25 min), 0% CH₃CN (35 min)).

(1S,4R)-4-(2-amino-$^6$-cyclopropylamino-9H-purin-9-yl)-2-cyclopentene-1-methanol O-[phenoxyphenyl-(methoxy-L-alaninyl)]-phosphate Cf 1787

The crude residue was purified twice by column chromatography, using MeOH:CHCl3 (3:97) and MeOH:CH$_2$Cl$_2$ (5:95) as eluent, to give the product as a yellow foam (35 mg, 0.058 mmol, 8%).

$\delta_P$ 4.2124.184.

$\delta_H$ 0.66 (m,2H,CH$_2$-cPr), 0.85 (m,2H,CH$_2$-cPr), 1.33 (m, 3H, CH3-CH), 1.7 (m, 1H, H'6), 2.8 (m, 1H, H'6), 2.9 (m, 1H, CH-cPr), 3.25 (m, 1H, H4), 3.6 (s, 3H, CH3-O), 4.1 (m, 1H, CH3-CH), 4.25 (m, 2H, H'5), 4.9 (m, 2H, NH2), 5.5 (m, 1H,H'1), 5.85 (m, 1'H, H'3), 6.15 (m, 2H, H'2,NHcPr), 7.35 (m, 9H, Ar), 7.6 (m, 1H, H8).

$\delta_C$ 6.371 (CH$_2$cPr), 21.49 (CH-CH3aa), 21.671 (NHCH3), 33.458 (C'6), 46.14 (C'4), 50.671 (CHaa), 52.9 (OCH3), 59.9 (C'1), 65.9 (C'5), 115.787 (CS), 120 (o-Ar), 122.22 p-Ar$_2$), 128.743 (m-Ar), 130 (C'3), 134.53 (C'2), 135.31 (C8), 153.83 (i-Ar$_2$, m-Ar$_1$), 155.18 (C6), 156.342 (C2), 158.8 (C4), 173.004 (COOCH3).

HPLC t$_r$: 18.830 min (0% CH$_3$CN (0 Min), 80% CH$_3$CN (15 min), 80% CH$_3$CN (25 min), 0% CH$_3$CN (35 min))

(1S,4R)-4-(2-amino-6cyclopropy]amino9H-purin-9-yl)-2-cyclopentene-1-methanol O-phenyl methoxy-α,α-cyclopentylglycinyl]phosphate Cf1763

This was prepared by Standard procedure 4 in 77% yield.

$^{31}$p (CDCl$_3$) 3.02, 3.09

$^1$H (CDCl$_3$) 0.56–0.61 (2H,m, CH$_2$ (cpro)), 0.81–0.89 (2H, m, CH$_2$ (cpro)), 1.58–1.78 (SH, m, CCH$_2$CH$_2$CH$_2$CH$_2$C, and H6'), 1.87–2.18 (4H, m, CCH$_2$CH$_2$CH$_2$CH$_2$C), 2.64–2.74 (1H, m, H6'), 2.83–3.09 (2H, m, CH(cpro), H4'), 3.60–3.62 (3H, s, OCH$_3$(ala)), 4.044.19 (2H, m, H5'), 5.20 (2H, bs, NH2), 5.42–5.47 (1H, n, HI'), 5.77–5.83 (1H, m, H3'), 5.98–6.02 (1H, m, H2'), 6.20 (NH(cpro)), 7.06–7.27 (SH, m, Ar), 7.42–7.48 (1H, s, H8). $^{13}$C (CDCl$_3$) 8.02 (CH$_2$(cpro)), 24.37, 24.41 (CCH$_2$CH$_2$CH$_2$CH$_2$C), 34.73 (C6'), 38.48, 38.68,38.79, 38.87 (CCH$_2$CH$_2$CH$_2$CH$_2$C), 46.05, 46.15 (C'4), 52.99 (OCH$_3$(ala)), 59.56, 59.60 (Cl'), 67.16 (C (aa), 69.28, 69.37 (C5'), 114.76 (CS), 120.46, 120.52 (o-Ph), 125.22 (p-Ph),130.04 (m-Ph), 131.19 (C3'), 136.72 (C8), 137.13, 137.20 (C2'), 151.27, 151.31, 151.36, 151.40 (C6), 155.56 (C4), 158.95 (C2),175.96, 176,00 (CO).

(1S,4R)-4-(2-amino-6-cyclopropylamino-9H-purin-9-yl)-2-cyclopentene-1-methanol O-[phenyl methoxy-α,α-cylohexylglycinyl] phosphate Cf1764

This was prepared by Standard procedure 4 in 15% yield.

$^{31}$p (CDCl$_3$) 2.89, 3.00

$^1$H (CDCl$_3$) 0.74 (2H,m, CH$_2$ (cpro)), 1.01–1.03 (2H, m, CH$_2$ (cpro)), 1.29–2.23 (11H, m, CCH$_2$CH$_2$CH$_2$CH$_2$CH$_2$C, and H6'), 2.72–2.83 (1H, m, H6'), 3.17 (1H, bs, CH(cpro)), 3.35–3.43 (1H, m, H4'), 3.69–3.70 (3H, s, OCH$_3$(aa)), 4.164.29 (2H, m, H5'), 5.52–5.66 (1H, m3 HI'), 5.79 (1H, bs, NH(cpro)), 5.85–5.90 (1H, m, H3'), 6.08–6.10 (1H, m, H2'), 7.15–7.35 (5H, m, Ar), 7.37–7.63 (1H, d, H8).

¯C (CDCl$_3$) 8.30 (CH$_2$(cpro)), 21.49, 21.68, 21.84, 22.02, 22.11 (CCH$_2$CH 2CH$_2$CH$_2$C), 25.14, 25.47, 25.72 (CCH$_2$CH$_2$CH$_2$CH$_2$C ), 34.37, 34.59 (C'6), 46.06, 46.16 (C'4), 52.75, 53.12 (OCH$_3$(aa)), 59.95, 60.19 (Cl'), 69.22 (CS'), 120.41, 120.47 (o-Ph), 125.22 (p-Ph), 130.04 (m-Ph), 130.72, 130.82 (C3'), 137.41 (C8), 137.56 (C2'), 151.33, 151.43 (C6), 175.37 (CO).

(1S,4R)-4-(2-amino-6-cyclopropylamino-9H-purin-9-yl)-2-cyclopentenel-methanol O-[phenyl methoxy-α,α-cylopropylglycinyl] phosphate Cf 1762

This was prepared by Standard procedure 4 in 69% yield.

$^{31}$ P (CDCl$_3$) 3.84

$^1$H (CDCl$_3$) 0.68(2H,m, CH$_2$ (cpro)), 0.90–0.92 (2H, m, CH$_2$ (cpro)), 1.16–1.49 (4H3 m, CCH$_2$CH7C(aa)), 1.66–1.72 (1H, m, H6'), 2.72–2.82 (1H, m, H6'), 3.08–3.15 (2H, m, CH(cpro), H4'), 3.61–3.63 (3H, d, OCH$_3$(aa)), 4.244.26 (2H, m, H5'), 5.24 (2H, bs, NH2), 5.53 (1H, bs, H1'), 5.87(1H, m, H3'), 6.07 (1H, m, H2'), 6.42–6.45 (1H, bs, NH(cpro)), 7.15–7.35 (SH, m, Ar), 7.56–7.61 (1H, d, HB).

$^{13}$C (CDCl$_3$) 7.92 (CH$_2$(cpro)), 18.38 (CH$_2$ (aa)), 35.20 (C6'), 52.88 (OCH3(aa)), 59.45 (Cl'), 69.32 (C5'), 120.52 (o-Ph), 125.29 (p-Ph), 130.04 (m-Ph),137.03 (C2'), 151.13 (C6),160.96, 160.98 (C2), 174.35 (CO).

(1S,4R)-4-(2-amino-6-cyclopropylamino-9H-purin-9-yl)-2-cyclopentene-1-methanol O-[p-(methoxycarbonyl)phenyl methboxy-L-alaninyl] phosphate Cf1766

This was prepared by Standard procedure 4 in 37% yield.

31P (CDCl$_3$) 3.54, 3.58

$^1$H (CDCl$_3$) 0.66–0.69 (2H,m, CH$_2$ (cpro)), 0.88–0.94 (2H, m, CH$_2$ (cpro)), 1.38–1.43 (3H, t, CH$_3$(ala)), 1.70–1.81 (1H, m, H6'), 2.76–2.89 (1H, m, H6'), 3.07 (1H, m, CH(cpro)), 3.21 (1H, mn, H4'), 3.71–3.73 (3H, d, OCH$_3$(ala)), 3.94 (3H, s, COOCH$_3$), 3.98–4.12 (1H, m, CH(ala)), 4.20–4.31 (2H, m, H5'), 5.19 (2H, bs, NH2), 5.54–5.57 (1H, m, H1'), 5.91–5.96 (1H, in, H3'), 6.09–6.14 (1H, m, H2'), 6.21 (1H, bs, NH(cpro)), 7.27–7.32 (2H, m, ArO,2H), 7.53–7.54 (1H, d, H8), 8.02–8.06 (2H, m, COAr,2H).

$^{13}$C (CDCl$_3$) 7.75 (CH$_2$(cpro)), 21.22, 21.29, 21.46 (CH$_3$ (ala)),24.16 (NHCH), 34.83 (C6'), 45.97, 46.07 (C'4), 50.59 (CH(ala)), 52.57, 59.32 (OCH$_3$ (ala), OCH$_3$(Ph)), 59.27, 59.32 (Cl'), 69.43 (C5'), 115.07, 115.11 (C5), 120.28, 120.31, 120.34, 120.38 (o-Ph), 127.07 (p-Ph), 131.58, 131.66 (m-Ph), 131.88 (C3'), 135.94, 136.04 (C2'), 136.61, 136.73 (C8), 151.31 (C6), 156.52 (C2), 160.97 (C4), 171.57 (CO), 174.30,174.39 (CO).

(1S,4R)-4-(2-amino-6-cyclopropylamino-9H-purin-9-yl)-2-cyclopentene-1-methanol O-[p-(trifluoromethylthio)phenyl methoxy-L-alaninyl]phosphate Cf 1769

This was prepared by Standard procedure 4 in 34% yield.

$^{31}$ P (CDCl$_3$) 3.67, 3.88

$^1$H (CDCl$_3$) 0.81 (2H,bs, CH$_2$ (cpro)), 1.06–1.08 (2H, m, CH$_2$ (cpro)), 1.50–1.54 (3H, t, CH$_3$(ala)), 1.83–1.93 (1I1, m, H6'), 2.87–2.99 (1H, m, H6'), 3.23–3.31 (1H, m, CH(cpro)), 3.82–3.84 (3H, d, OCH$_3$(ala)), 4.1 44.15 (1H, mi, CH(ala)), 4.32–4.40 (2H, m, H5'), 5.65 (3H, bs, H1', NH$_2$), 6.01–6.04 (11, m, H3'), 6.19–6.23 (1H, m, H2'), 6.64 (1H, bs, NH(cpro)), 7.37–7.43(2H, m, Ar), 7.67 (1H, d, H8), 7.73–7.76 (2H, m, Ar). 7C (CDC)$_3$) 8.16 (CH$_2$(cpro)), 21.39, 21.45 (CH$_3$(ala)), 34.45 (C6'), 46.09 (C4'), 50.66 (CH(ala)), 53.01 (OCH$_3$ (ala)), 59.87 (Cl'), 69.34 (C5'), 77.47, 77.67 (CF$_3$S ?), 121.64, 121.69 (o-Ph), 127.07 (p-Ph), 136.99, 137.14 (C2'), 138.56 (C8), 153.36, 153.45 (C6), 160.93 (C4), 174.27 (CO).

(1S,4R)-4-(2-aminotcyclopropy]2 amino9H-purin-9-yl)2-cyclopentene-1-methano O-[p-(2-methoxyvinyl)phenyl methoxy-L-alaninyl] phosphate Cf 1767

This was prepared by Standard procedure 4 in 38% yield.

31p (CDCl$_3$) 3.70, 3.74

$^1$H (CDCl$_3$) 0.58–0.61 (2H,bs, CH$_2$ (cpro)), 0.81–0.85 (2H, m, CH$_2$ (cpro)), 1.30–1.36 (3H, t, CH$_3$(ala)), 1.61–1.72 (1H, m, H6'), 2.33 (31H, s, CH$_3$CO), 2.70–2.79 (1H, m, H6'), 2.99 (1H, bs, CH(cpro)), 3.13(1H, bs, 1H4'), 3.64–3.65 (3H, d, OCH$_3$(ala)), 3.924.01 (1H, m, CH(ala)), 4.114.21 (2H, m, H5'), 5.14 (3H, bs, H1', NH2), 5.47–5.49 (1H, m, HI'), 5.82–5.87 (1H, m, H3'), 6.01–6.06 (1H, m, H12'), 6.12 (1H, bs, NH(cpro)), 6.57–6.63 (1H, dd, CH3COCH=C$\underline{H}$), 7.14–7.46 (6H, m, H8, Ar, CH$_3$COC$\underline{H}$=).

$^{13}$C (CDC)$_3$) 7.95 (CH$_2$(cpro)), 21.45 (CH$_3$(ala)), 28.02 ($\underline{C}$H$_3$CO), 34.69 (C6'), 46.11 (C4'), 50.64 (CH(ala)), 52.99 (OCH$_3$ (ala)), 59.53 (Cl'), 121.03, 121.10, 121.17 (o-Ph), 127.39 (p-Ph), 130.13 (CH$_3$COCH=$\underline{C}$H), 131.44, 131.55 (C3'), 136.76 (C2'), 142.59 (CH$_3$CO$\underline{C}$H=CH), 152.72 (C6), 174.26,174.36 (CO(ala)), 198.70 (COCH$_3$).

(1S,4R)-4-(2-amino-6cyclopropylamin o-$^9$H-purin-9-yl)-2-cyclopentene-1-methanol O-[p-(2-phenylcarbonylvinyl) phenyl methoxy-L-alaninyl] phosphate Cf 1771

This was prepared by Standard procedure 4 in 26% yield.
$^{31}$P (CDCl$_3$) 3.75, 3.79
$^1$H (CDCl$_3$) 0.61–0.66 (2H,m, CH$_2$ (cpro)), 0.85–0.91 (2H, m, CH$_2$ (cpro)), 1.39–1.44 (3H, m, CH3(ala)), 1.67–1.86 (1H, m, H6'), 2.77–2.87 (1H, m, H6'), 3.04–3.05 (1H, bs, CH(cpro)), 3.19–3.21 (1H, bs, H4'), 3.72–3.73 (3H, d, OCH$_3$(ala)), 4.02 4.13 (1H, m, CH(ala)), 4.19 4.29 (2H, m, H5'), 5.17 (3H, bs, H1', NH$_2$), 5.53–5.58 (1H, n, H1'), 5.90–5.95 (11H, m, H3'), 6.09–6.15 (2H, m, H12', NH(cpro)), 7.24–8.08 (12H, m, Ar-, CH=C H, —Ar—, H8).
$^{13}$C (CDCl$_3$) 7.85 (CH$_2$(cpro)), 21.35, 21.41, 21.48 (CH$_3$ (ala)), 24.22 (CH(NH)), 34.80 (C6'), 46.01 (C4'), 50.67 (CH(ala)), 52.97 (OCH$_3$ (ala)), 59.37 (C1'), 69.40 (C5'), 115.07 (C5), 121.01, 121.07, 121.14 (o-Ph), 128.92, 129.06 (p-Ph), 133.27 (C3'), 136.13, 136.23 (C2'), 138.53 (C8), 152.77, 152.86 (C6), 156.31 (C2), 160.97, 160.99 (C4), 174.31, 174.41 (CO(ala)), 190.76 (CO (Ar)).

(1S,4R)-4-(2-amino6-cyclopropylamin o-9H-purin-9-yl)-2-cyclopentene-1-methanol O[p-(2,2-dicyanovinyl)phenyl methoxy-L-alaninyl] phosphate Cf 1768

This was prepared by Standard procedure 4 in 10% yield.
$^{31}$P (CDCl$_3$) 4.54, 4.65
$^1$H (CDCl$_3$) 0.61–0.66 (2H,m, CH$_2$ (cpro)), 0.85–0.91 (2H, m, CH$_2$ (cpro)), 1.34–1.41 (3H, CH$_3$(ala)), 1.67–1.83 (1H, m, H6'), 2.77–2.88 (1H, m, H6'), 2.95–2.97 (1H, m, H(cpro)), 3.23 (1H, bs, H4'), 3.68–3.70 (3H, d, OCH$_3$(ala)), 3.99–4.03 (1H, m, CH(ala)), 4.22–4.32 (2H, m, H5'), 5.49–5.53 (11H, m, H1'), 5.99–6.03 (1H, m, H3'), 6.16 6.22 (1H, m, H2'), 6.94–6.97 (1H, dd, Ar-CH=CH), 7.36–7.41 (Ar), 7.64–7.65 (1H, d, H8), 7.92–8.16 (Ar).
$^{13}$C (CDCl$_3$) 6.56 (CH$_2$(cpro)), 19.85 (CH$_3$(ala)), 23.33 (CH(cpro)), 34.23 (C6'), 46.07 (C4'), 50.47, 50.53 (OCH$_3$ (ala)), 51.78 (CH(ala)), 59.51 (C1'), 69.19, 69.29 (C5'), 113.84, 114.08 (C5), 121.14, 121.21, 121.27 (o-Ph), 128.49 (p-Ph), 130.74, 130.85 (m-Ph), 132.84 (C3'), 136.01 (C2'), 136.88, 136.99 (C8), 156.47 (C2), 160.99, 161.03 (C4), 174.27 (CO).

(1 S,4R)-4-(2-amino-$^6$-cyclopropylamino-9H-purin-9-yl)-2-cyclopentene-1-methanol O-[o(carboxylate ethyl ester) phenyl methoxy-L-alaninyl]phosphate Cf1798

This was prepared by Standard procedure 4 in 24% yield.
$^{31}$P (CDCl$_3$) 4.03, 4.16
$^1$H (CDCl$_3$) 0.64–0.70 (2H,m, CH$_2$ (cpro)), 0.92–0.93 (2H, d, CH$_2$ (cpro)), 1.38–1.47 (6H, m, CH$_3$(ala), CH$_3$CH$_2$O), 1.73–1.83 (1H, m, H6'), 2.78–3.24 (3H, m, H6', H4', CH(cyclo)), 3.64–3.72 (3H, s, OCH$_3$(ala)), 4.08 4.20 (1H, m, CH(ala)), 4.23 4.45 (4H, m, H5', CH$_2$CH$_3$), 5.21 (2H, bs, NH2), 5.55–560 (1H, m, H1'), 5.89–5.93 (1H, m, H3'), 6.13–6.18 (1H, m, H2'), 7.23–7.61 (1H, m, H8), 7.88–7.92 (1H, d, Ar).
$^{31}$C (CDCl$_3$) 7.95 (CH$_2$(cpro)), 14.65 (CH$_3$CH$_2$), 21.33, 21.39, 21.68, 21.74 (CH$_3$(ala)), 24.30 (NHCH), 34.80 (C6'), 46.04, 46.14 (C4'), 50.49 (CH(ala)), 52.74, 52.83 (OCH$_3$ (ala)), 59.45 (C1'), 61.76, 61.82 (CH$_2$CH$_3$), 69.43, 69.51, 69.64 (C5'), 114.92 (C5), 122.93, 123.09, 123.60, 123.67 125.26 (Ar), 131.34 (Ar), 131.77, 131.86 (C3'), 134.00 (Ar), 136.48 (C2'), 137.05 (C8), 150.20, 150.28 (C6), 155.88 (C2), 160.78, 160.86 (C4), 174.28, 174.39, 174.55, 174.65 (CO).

EXAMPLE A (1R, 4S)-9-14-(hydroxymethyl)-2-cyclopenten-2-yl]guanine-5'-[phenyl-(methoxy-L-alaninyl)]-phosphate.
C$_{21}$H$_{25}$O$_6$N$_6$P$_1$, MW=488.45.

R. Vince and M. Hua, J. Med. Chem. 1990, 33, 17–21, which is hereby incorporated by reference, describes a procedure for the sysnthesis of (1R, 4S)-9-{4-(hydroxymethyl)-2-cyclopenten-1-yl]guanine.

(1R,4S)-9-[4-(hydroxymethyl)-2-cyclopenten 1-yl]guanine (400 mg, 1.618mmol) was dried by azeotroping with anhydrous pyridine (4×10 ml), kept under N$_2$(g), and suspended in anhydrous THF (30 m1l). tBuMgCl (1.0M solution in THF) (1.6 ml, 1.618mmol) was added dropwise and the resulting darker suspension vigorously stirred for 10 min. Phosphorochloridate (4.79 ml, 2.43mmol) was added dropwise, and the reaction mixture stirred at room temperature for 69 hrs. After this time, the suspended solid was partially in solution but a solid was still observed on the sides of the flask. More phosphorochloridate was added (4.79 ml, 2.43 mmol), and the reaction mixture stirred for a further 55 hrs before being quenched by the addition of sat.NH$_4$Cl solution (0.25 m). After stirring for a further 10 mins, the solvent was removed under reduced pressure to give the crude product as a yellow gum which was solubilised in MeOH, dried over MgSO$_4$ (s), filtered and the filtrate reduced to dryness. The residue was solubilised in MeOH, silica added, and then the solvent removed to give the product preabsorbed onto silica which was loaded onto a silica column and eluted with 8% MeOH in CHCl$_3$. The product was further purified by gradient elution from 5→9 MeOH in DCM on a biotage flash-40 column, and after evaporation of the appropriate fractions, the product was obtained as a white foam (70 mg, 8.6%).

The compound had the formula

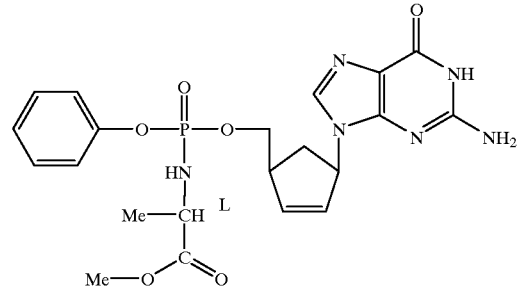

$^{31}$ P NMR (MeOH-d$_4$): δ5.18, 4.86 (1:1).
$^1$H NMR: δ7.67 (1H), 7.37–7.30 (2H), 7.21–7.14 (3H), 6.17–6.10 (1H), 5.97–5.94 (1H), 5.53–5.48 (1H), 4.28–4.15 (2H), 4.00–3.87 (1'H), 3.66 (3H), 3.18 (1H), 2.83–2.71 (1H), 1.82–1.66 (1H), 1.36–1.29 (3H).
$^{13}$C NMR: δ174.4*, 158.5, 154.1, 151.7, 151.1*, 136.9*, 136.5, 130.7, 129.7, 125.0, 120.4*, 116.8, 68.9*, 59.8, 51.7, 50.5*, 46.0*, 34.2,19.3*.
MS ES$^+$: m/z 488.86 (100%) (M)$^+$, 500.04 (12%)(M+Na)$^+$, 507.96 (25%)(M+K)$^+$.
MS FAB: calculated m/z 489.165146, found m/z 489.164677.

In Vitro Testing

Cells were infected with HIV-1 as previously described [Balzarini et al. AIDS (1991), 5, 21–28]. Briefly, 5×10$^5$ cells per milliliter were infected with HIV-1 or HV-2 at 100 CCID$_{50}$ (50% cell culture infective dose) per milliliter of cell suspension. Then 100 μL of the infected cell suspension was transferred to microtiter plate wells and mixed with 100 μL of the appropriate dilutions of the test compounds. After 4 days giant cell formation was recorded microscopically in the HIV-infected cell cultures [CEM]. The 50% effective concentration (EC$_{50}$) and 50% cytoxic concentration (CCso) were defined as the compound concentrations required to reduce by 50% the number of giant cells or viable cells in the virus-infected and mock-infected cell cultures, respectively.

In the following Tables data columns are, in order:
HIV1 CEM: $EC_{50}$ in $\mu M$ for inhibition of HIV-1 in CEM cells.
HIV1 CEM: $EC_{50}$ in $\mu M$ for inhibition of HIV-2 in CEM cells.
CC50 CEM: $CC_{50}$ in $\mu M$ for toxicity to CEM cells.

Table I below contains in vitro data comparing the biological activity of compound cf1490 with its non-phosphorarmidated counterpart, Abacavir, and with the compound of comparative Example A and its non-phosphoramidated counterpart. Abacavir is currently used in the treatment of patients with HIV infection.

TABLE I

| Compound | $EC_{50}/\mu M$ HIV-1 CEM | $EC_{50}/\mu M$ HIV-2 CEM | $CC_{50}/\mu M$ CEM | Fold Improvement |
|---|---|---|---|---|
| 1490 | 0.07 | 0.09 | 13.1 | 30.2 |
| Abacavir | 1.9 | 3 | 78 | |
| Example A | 1.3 | 0.85 | 123 | 1.9 |
| Nonphosphoramidated counterpart of Example A | 2 | 2.3 | 157 | |

As can be seen in Table I compound cf1490 embodying the present invention shows a much enhanced potency (27 to 33 fold) with respect to HIV in vitro than the known non-phosphoraridated Abacavir. The fold improvement in Table I is the mean increase in potency of the phosphoramidate compound versus its parent nucleoside for HIV 1 and HIV 2.

The surprising nature of this result is demonstrated having regard to Comparative Example A and its non-phosphoramidated counterpart. The structure of the non-phosphoramidated counterpart of Example A is prima facie similar to that of Abacavir. The phosphoramidate of Example A, however, shows a potency with respect to HIV which is merely comparable to that of its nonphosphoramidated counterpart, whose structural formula is:

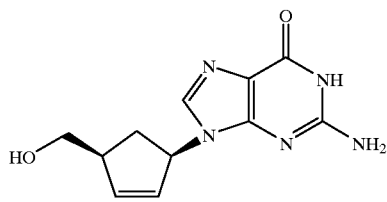

Table II below compares the in vitro potency data of the compound 1490 with known equivalent data disclosed in PCT/GB96/00580 for known phosphoramidated compounds. The data in each case were obtained by the in vitro assay descibed above under "In vitro testing"

TABLE II

| Compound | $EC_{50}/\mu M$ HIV-1 CEM | $EC_{50}/\mu M$ HIV-2 CEM | $CC_{50}/\mu M$ CEM |
|---|---|---|---|
| 1490 | 0.07 | 0.09 | 13.1 |
| 951 | 0.1 | 0.07 | 5.5 |
| 1078 | 0.55 | 0.65 | 209 |
| 1093 | 0.016 | 0.035 | 2.57 |

Each of compounds 951, 1078 and 1093 is a phosphoramidate of a nucleoside analogue.

Compound 951 is 2', 3'-dideoxy-2', 3'-didehydrothymidine 5'-(phenyl exthoxyalaninyl) phosphoramidate.

Compound 1078 is 2', 3'-dideoxy-2', 3'-didehydrothymidine 5'-(phenyl dimethoxyaspartyl) phosphoramidate.

Compound 1093 is 2', 3'-dideoxy adenosine 5'-(phenyl methoxyalaninyl) phosphoramidate.

As can be seen from Table II the compound 1490 demonstrates a high degree of potency with respect to HIV.

Potency and toxicity data on an expanded range of compounds is presented in Table III, in which:
Cpd and Init refer to the compound reference numbers;
X refers to the aryl (phosphate) moiety;
Y refers to the group;

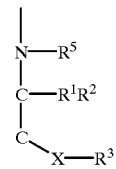

Z refers to the bonding in the five membered sugar ring:=is unsaturated pentene; H is saturated.

B in each case is "1592" which refers to the base present in Abacavir.

The data columns are, in order:
HIV 1 CEM: $EC_{50}$ in $\mu M$ for inhibition of HIV1 in CEM cells
HIV2 CEM: $EC_{50}$ in $\mu M$ for inhibition of HIV-2 in CEM cells
HIV2CEM.TK- $EC_{50}$ $\mu M$ for inhibition of IV-2 in CEM= cells
CC50 CEM: $CC_{50}$ $\mu M$ for toxicity to CEM cells
EC50 MSV: $EC_{50}$ $\mu M$ for inhibition of MSV
MCC MSV: minimum cytotoxic concentration in MSV essay.

TABLE III

| Cpd | Init | X | Y | Z | B | HIV1 CBM | HIV2 CBM | HIV2 CEM. TK. | CC50 CEN | EC50 MSV | MCCMSV |
|---|---|---|---|---|---|---|---|---|---|---|---|
| 1490 | SH | PhO | MaAlaNH | = | 1592 | 0.05 | 0.05 | | 13.1 | 1.6 | >4 |
| 1540 | SH | CH | AlaNH | = | 1592 | 1.2 | 0.95 | | 115 | | |
| 1582 | SH | PhO | BzAlaNH | = | 1592 | 0.083 | 0.11 | — | 12.5 | | |
| 1583 | SH | PhO | Me-D-AlaNH | = | 1592 | 1.38 | 4.5 | — | 64.3 | | |
| 1584 | SH | PhO | Me(Me2Gly)NH | = | 1592 | 0.067 | 0.06 | — | 8.91 | | |
| 1585 | SH | PhO | MePheNH | = | 1592 | 1.42 | 2.13 | — | 36.1 | | |
| 1587 | SH | PhO | EtAlaNH | = | 1592 | 0.07 | 0.06 | — | 12.1 | | |

TABLE III-continued

| Cpd | Init | X | Y | Z | B | HIV1 CBM | HIV2 CBM | HIV2 CEM. TK. | CC50 CEN | EC50 MSV | MCCMSV |
|---|---|---|---|---|---|---|---|---|---|---|---|
| 1588 | SH | PhO | MeGlyNH | = | 1592 | 1.78 | 2 | — | ≥100 | | |
| 1589 | SH | PhO | Me2AspNH | = | 1592 | 1.42 | 1.9 | — | 44.2 | | |
| 1595 | SH | HO | D-AlaNH | = | 1592 | 1.2 | 1.2 | 0.8 | 213 | | |
| 1620 | SH | p-ClPhO | MeAlaNH | = | 1592 | 0.014 | 0.063 | 0.013 | 4.7 | | |
| 1645 | SH | PhO | tBuAlaNH | = | 1592 | 3.7 | 6 | | 33 | 11.7 | >20 |
| 1646 | SH | PhO | PrAlaNH | = | 1592 | 0.093 | 0.12 | | 9 | 2 | >4 |
| 1647 | SH | PhO | BuAlaNH | = | 1592 | 0.085 | 0.17 | | 8.23 | 0.62 | >4 |
| 1661 | SH | PhO | IPrOAlaNh | = | 1592 | 0.5 | 0.85 | | 9.18 | 2.75 | ≥20 |
| 1671 | AS | p-MeOCOC(OMe2)CPh | MeAlaNH | = | 1592 | 0.1 | 0.12 | | 12.1 | 9.2 | >20 |
| 1672 | AS | PhO | IPrCH2AlaNH | = | 1592 | 0.09 | 0.1 | | 14.4 | 1.98 | >4 |
| 1673 | AS | PhO | tBuCH2AlaNH | = | 1592 | 0.15 | 0.18 | | 8.07 | 2.92 | >4 |
| 1674 | AS | PhO | IPrCH2CH2AlaNH | = | 1592 | 0.25 | 0.25 | | 10.7 | 2.04 | >4 |
| 1880 | AHA | PhO | MeAlaNH | H | 1592 | 12.5 | 17.5 | | 237 | ≥100 | >100 |
| 1685 | SS | PhO | 3-pentyl Ala NH | = | 1592 | 1.6 | 2 | 12.5 | 19.7 | 10.1 | >20 |
| 1666 | SS | PhO | Meval NH | = | 1592 | 3.5 | 4 | 3.5 | 54.1 | 11.8 | >20 |
| 1687 | SS | PhO | tBuCH2CH2AlaNH | = | 1592 | 0.2 | 0.2 | 0.14 | 10.2 | 2.22 | >4 |
| 1702 | AHA | — | — | H | 1592 | ≥50 | ≥50 | | 179 | ≥100 | >100 |
| 1706 | SH | PhO | nPnAlaNH | = | 1592 | 0.065 | 0.08 | | 16.4 | 1.45 | >4 |
| 1707 | SH | PhO | cHxAlaNH | = | 1592 | 0.33 | 0.25 | | 10.2 | 2.84 | >4 |
| 1708 | SH | PhO | cHxCH2AlaNH | = | 1592 | 0.15 | 0.16 | | 15.1 | 1.3 | >4 |
| 1709 | SH | PhO | Me(CHxCH2Gly)NH | = | 1592 | 1.2 | 2 | | 16 | 1.72 | >4 |
| 1710 | SH | 4-Br-PhO | MeAlaNH | = | 1592 | 0.0055 | 0.049 | | 5.78 | 0.51 | >0.8 |
| 1713 | AS | 4MOOC(MeO)2CCH2 | MeAlaNH | = | 1592 | 0.053 | 0.065 | | 14 | 10.8 | >20 |
| 1714 | AS | PhO | dIEtASP | = | 1592 | 0.55 | 2.1 | | 23.1 | 7.18 | >20 |
| 1715 | AS | PhO | MeMET | = | 1592 | 1.15 | 2.73 | | 48.9 | 10.2 | >20 |
| 1718 | SS | PhO | MeLeuNH | = | 1592 | 0.85 | 1.48 | | 22 | 8.84 | >20 |
| 1719 | SS | PhO | MeProN | = | 1592 | 4 | 5.5 | | 19.4 | 11.6 | ≥100 |
| 1720 | SS | PhO | Bn2AspNH | = | 1592 | | | | | | |
| 1721 | SS | PhO | IPr(CH2)3AlaNH | = | 1592 | 0.05 | 0.14 | | 12.5 | 2.2 | >4 |
| 1722 | SS | PhO | cPentCH2AlaNH | = | 1592 | 0.13 | 0.48 | | 15.2 | | |
| 1737 | SH | p-F-PhO | MeAlaNH | = | 1592 | | | | | | |
| 1738 | SH | p-I-PhO | MeAlaNH | = | 1592 | | | | | | |
| 1739 | SH | PhO | nHxAlaNH | = | 1592 | | | | | | |
| 1749 | AS | PhO | Me2GluNH | = | 1592 | 3.5 | 5.33 | | 36.9 | | |
| 1750 | AS | PhO | MeTrpNH | = | 1592 | 3 | 3.67 | | 18.3 | | |
| 1751 | AS | PhO | MeIleNH | = | 1592 | 7 | 5.33 | | 24.2 | | |
| 1752 | AS | PhO | cHeptAlaNH | = | 1592 | 1.3 | 1.05 | | 6.32 | | |

Acid stability

Compounds were tested for their stability towards acid-mediated hydrolytic decomposition employing a test designed to simulate stomach conditions. Each compound was incubated in dilute HCl of pH1 for 24 hours at 25° C. 0.3 mg of compound were added to 1 mL of 0.1N HCl at 25° C. HPLC was run immediately for time=0 and at intervals up to approximately 24 hours.

The results for compound 1587, and for comparative compounds labelled 1001 and 1093 and described in PCT/GB96/00580, are given in table IV below.

TABLE IV

| Compound | Time (hr) | Compound left (%) |
|---|---|---|
| 1587 | 0 | 100 |
| | 22 | 77 |
| 1001 | 0 | 0 |
| | 17 | 0 |
| 1093 | 0 | 100 |
| | 13 | 0 |

Compound 1001 disappeared immediately (<1 min). Compound 1093 degraded after less than 13 hours. The majority of compound 1587 remained in tact after 22 hours.

Each of compounds 1001 and 1093 is a phosporamidate of an adenosine analogue. 20 Compound 1001 is 2', 3'-dideoxy-2', 3'-didehydroadenosine-5'-(phenylmethoxyalaninyl) phosphate. Compound 1093 is 2', 3'-dideoxy adenosine 5'-(phenyl methoxyalaninyl) phosphate.

The results given in Table V above demonstrate the acid stability of a compound embodying the present invention compared to known compounds.

Biological stability

Compound 1587 of the present invention and the two comparative compounds 1001 and 1093 identified above were tested for their stability towards biological decomposition. Each compound was incubated in normal heparinised human plasma at 37° C. for 4 hours. At selected time points (0, 15, 30 min, and 1, 2, 4 hours) duplicate samples were removed and deproteinated by acetonitrile extraction. Drug concentrations were then determined by LC/MS/MS analysis using standard methods. The results are shown in Table V below.

TABLE V

| Compound | % Remaining at 4 hours | Half-life (hours) |
|---|---|---|
| 1587 | 91 | 26 |
| 1001 | 52 | 4.6 |
| 1093 | 50 | 4.2 |

Under the conditions of the test the data in Table V shows a 6-fold stability advantage of compound 1587 over each of compounds 1001 and 1093.

EXAMPLE 1

(1S,4R)-442-Amino-6-cyclopropylamino-9(purin-9-yl)-2-cyclopentene-1-methanol O-(phenyl ethoxy-L-alaninyl) phosphate Succinate Salt (a) Phenylethoxy-L-alaninyl phosphorochloridate L-alanine ethyl ester hydrochloride (3.0 g, 0.02 moles) was suspended in dry methylene chloride (40 mL). To this suspension was added phenyl phosphorodichloridate (2.9 ml, 0.02 mol) and the mixture was cooled to −80° C. N,N-Diisopropylethylamine (Aldrich, 6.8 mL, 0.04 mol) was added to the reaction in aliquots (1–2 mL) over a 1 h time period. Reaction allowed to warm slowly to room temperature while stirring for 2 h. Organic solvent was removed in vacuo and the residue treated with diethyl ether (100 mL). The diethyl ether solution was filtered to remove insoluble inorganics and concentrated in vacuo to give the product as a colourless syrup. This product was used without further purification in part b.

(b) (1S,4R)-4-(2-amino-6-cycloironylamino-9(H)-purin-9-yl)-2-cyclopentene-1-methanol O-(phenl ethoxy-L-alaninyl) phosphate (1S4R)-4-(2-amino-6-cyclopropylamino-9(H)-purin-9-yl)-2-cyclopentene-1-methanol (1.5 g, 5.2 mmol) was dried by addition of dioxane and concentration in vacuo. To the dried nucleoside was added anhydrous pyridine (10 mL) and tetrahydrofuran (20 mL). Subsequently, tert-butyl magnesium chloride (6 mL, 1M solution in tetrahydrofuran, 6 mmol) was added slowly. The reaction was stirred for 20 min and a solution of phenyl ethoxy-L-alaninyl phosphorochloridate (part a, 3 g, 0.01 mol in 20 mL tetrahydrofuran) was added. The reaction was stirred at room temperature for 10 h and subsequently concentrated in vacuo to a brown syrup. This syrup was dissolved in methylene chloride (100 mL) the methylene chloride extracted with water (2×100 mL), dried MgSO$_4$), filtered and concentrated to a brown solid foam. This solid foam was purified by flash chromatography using 5% methanol in chloroform as eluent to give 1.7 g (60%) of, after purification, a 4:6 mixture of the phosphate isomers as a white solid foam. $^1$H-NMR (CDCl$_3$): δ7.47 (2 x s, 1H), 7.10–7–46 (m, 5H), 6.07 (m, 1H), 5.9 (m, 1H), 5.78 (s, 1H), 5.5 (m, 1H), 4.84 (s, 2H), 4.1 (m, 4H), 4.00 (m, 1H), 3.64 (m, 1H), 3.14 (m, 1H), 3.0 (m, 1), 2.78 (m, 1H), 1.68 (m, 1H), 1.36 (2xd, 3H), 1.22 (2xt, 3H), 0.86 (m, 2H), 0.6 (m, 2H); $^{31}$P-NMR (CDCl$_3$): δ3.05, 3.02. Anal. Calcd. for C$_{25}$H$_{32}$N$_7$O$_5$P×1/4CHCl$_3$: C, 53.07; H, 5.70; N, 17.15. Found: C, 52.81; H, 5.95; N, 16.91.

(c) (1S,4R)-4-(2-Amino-6-cyclopropylamino-9(H)-,purin-9-yl)-2-cyclopentene-1-methanol O-(phenyl ethoxy-L-alaninyl) phosphate Succinate Salt (1S,4R)-4-(2-amino-6-cyclopropylamino-9(H)-purin-9-yl)-2-cyclopentene-1-methanol O-(phenyl ethoxy-L-alaninyl)phosphate (part 1b, 376 mg, 0.7 mmol) was dissolved in ethanol. To this solution was added succinic acid (82 mg, 0.7 mmol) and the resulting solution evaporated to dryness. The residue was dissolved in acetonitrile (10–20 mL) with heating. Precipitate formed upon cooling. The mixture was stored in the refrigerator overnight and solid collected by filtration to give 330 mg (72%) of a 4:6 mixture of the phosphate isomers as a solid; $^1$H-NMR (DMSO-d$_6$): δ12.14 (s, 2H), 7.58 (s, 1H), 7.1–7.4 (m, 6H), 5.9–6.1 (m, 3H), 5.85 (broad s, 2H), 5.42 (m, 1H), 3.95–4.15 (m, 4H), 3.8 (m, 1H), 3.05 (m, 2H), 2.65 (m, 1H), 2.4 (s, 4H), 1.63 (m, 1H), 1.4 (2xd, 3H), 1.12 (t, 3H), 0.5–0.7 (m, 4H); 3P-NMR (DMSO-d,6): 5; 4.00 and 3.68; high resolution mass spectrum: calcd for C$_{25}$H$_{32}$N$_7$O$_5$P (M+H)$^+$(m/z) 542.2281, found 542.2282. Anal. Calcd. for C$_{25}$H$_{32}$N$_7$O$_5$P C$_4$H$_6$O$_4$1/2H$_2$O: C, 52.09; H, 5.87; N, 14.66. Found: C, 52.13; H, 5.72; N, 14.61.

EXAMPLE 2

(1S,4R)-4-(2-amino-6cyclopropylamino-9(H)-purin-9-yl)-2-cyclopentene-1-methanol O-(phenyl methoxy-L-alaninyl) phosphate Succinate Salt (a) Phenylmethoxy-L-alaninyl phosphorochloridate.

L-alanine methyl ester hydrochloride (10 g, 0.072 mol) was suspended in dry methylene chloride (100 mL). To this suspension was added phenyl phosphorodichloridate (10.7 g; 7.6 mL) and the mixture was cooled to −80° C. Subsequently N,N-Diisopropylethylamine (Aldrich, 25 ml) was added to the reaction in aliquots (1–2 mL) over a 1 h time period. The solution was stirred for 30 min at −80° C., then allowed to warm slowly to room temperature while stirring for 2 h. Organic solvent was removed in vacuo and the residue treated with diethyl ether (100 mL). The diethyl ether solution was filtered to remove insoluble inorganics and concentrated in vacuo to give the product as a colorless syrup:

$^{31}$P-NMR (CDCl$_3$) 8 8.61; 8.37 ppm. This product was used without further purification in

EXAMPLE 2b (b) (1S,4R)S-(2-amino-6-cyclopropylamino-9M-purin-9-yl-2-cyclopentee-1-methanol O-(phenyl methoxy-L-alaninyl) phosphate (1S4R)-4(2-amino-6-cyclopropylamino-9H)-purin-9-yl)-2-cyclopentene-1-methanol (5.5 g, 0.018 moles) was dried by addition of dioxane and concentration in vacuo. To the dried nucleoside was added anhydrous tetrahydrofuran (30 mL) and pyridine (40 mL). Subsequently tert-butyl magnesium chloride (23 mL, 1M solution in tetrahydrofuran, 1.3 equivalents) was added slowly. The reaction was stirred for 20 min and a solution of phenylmethoxy-L-alaninyl phosphorochloridate (12 g, 0.043 moles, 2.5 equivalents in 20 mL THF) was added. The reaction was stirred at room temperature for 12 h and subsequently concentrated in vacuo to a brown syrup. This syrup was dissolved in methylene chloride (100 mL) the methylene chloride extracted with water (2×100 mL), dried (MgSO$_4$), filtered and concentrated to a brown foam. This foam was purified by flash chromatography using 5% methanol in chloroform as eluent to give 6.9 g (75%) of a mixture of the phosphate isomers of the title compound as a white solid foam. $^1$H-NMR (CDCl$_3$): δ7.5 (2 x s, 1H), 7.1–7.4 (m, 5H), 6.1 (m, 1H) 5.9 (m, 2H), 5.5–5.6 (m, 1H), 4.9 (bs, 2H), 4.2 (m, 2H), 4.05 (m, 1H), 3.7 (s, 3H), 3.6–3.8 (m, 1H) 3.17 (m, 1H), 3.0 (a, 1H), 2.8 (m, 1H), 1.7 (m, 11 ), 1.4 (2 x d, 3H), 0.9 (m, 2H), 0.6 (m, 2H); 3NMR (CDl$_3$): δ3.07, 3.02. Anal. Calcd. for C$_{24}$H$_{30}$N$_7$O$_5$P×2/5 CHCl$_3$: C, 50.94; H, 5.33; N, 17.00. Found: C, 50.83; H, 5.39; N, 16.94.

(c) (1S,4R)-4-(2-amino-6-cyclopropyamino-9(H)-purin-9-yl)-2-cyclopentne-1-methanol O-(phenyl methoxy-L-alaninyl)phosphate Succinate Salt (1S,4R) 4–2-amino-6-cyclopropylamino-9(H)-purin-9-yl)-2-cyclopentene-1-methanol O-(phenyl methoxy-L-alaninyl)phosphate (part b, 100 mg, 0.19 mmol) was dissolved in methanol. To this solution was added succinic acid (22 mg, 0.19 mmol) and the resulting solution evaporated to dryness. The residue was dissolved in acetonitrile (GOEL) with heating. Precipitate formed upon cooling. The mixture was stored in the refrigerator overnight and solid collected by filtration to give 70 mg (57%) of a mixture of the phosphate isomers as a solid; $^1$H-NMR (DMSO-di): 6 12.15 (s, 2H, D$_2$O exchangeable), 7.61 (s, 1H), 7.36 (3H, becomes 2H on D$_2$O exchange), 7.20 (3H), 5.9–6.1 (m, 3H), 5.88 (broad s, 2H, D$_2$O exchangeable), 5.44 (m, 1H), 4.0–4.2 (m, 2H), 3.85 (m, 1H), 3.60 (s, 3H), 3.05 (2H), 2.65 (m, 1H), 2.44 (s, 4H), 1.64 (m, 1H), 1.23 (m, 3H), 0.5–0.7 (m, 4H); $^{31}$ P-NMR (DMSO-d$_6$): δ3.99 and 3.66;
Anal. Calcd. for $C_{24}H_{30}N_7O_5P \cdot C_4H_6O_4 \cdot 1/2H_2O$: C, 51.38; H, 5.70; N, 14.98. Found: C, 51.36; H, 5.66; N, 14.99.

EXAMPLE 3

(1S,4R)-4-(2-Amino-6cyclopropylamino-9(H)-purin-9-yl)-2-cyclopentene-1-methanol O-(phenyl ethoxy-L-alaninyl) phosphate Fumarate Salt (1S,4R)-4-(2-amino-6-cyclopropylamino-9(H)-purin-9-yl)-2-cyclopentene-1-methanol O-(phenyl ethoxy-L-alaninyl)phosphate (198 mg, 0.37 mmol) was dissolved in ethanol. To this solution was added fumaric acid (43 mg, 0.37 mmol) and the resulting solution evaporated to dryness. The residue was dissolved in acetonitrile (10 mL) with heating. Precipitate formed upon cooling. The mixture was stored in the refrigerator overnight and solid collected by filtration to give 185 mg (75%) of a 4:6 mixture of the phosphate isomers as a solid; $^1$H-NMR (DMSO-d$_6$): δ7.6 (s, 1H), 7.1–7.4 (m, 6H), 6.64 (s, 2H), 5.9–6.1 (m, 3H), 5.87 (broad s, 2H), 5.44 (m, 1H), 3.95–4.15 (m, 4H), 3.84 (m, 1H), 3.05 (m, 2H), 2.65 (m, 1H), 1.63 (m, 1H), 1.23 (in, 3H), 1.15 (t, 3H), 0.5–0.7 (m, 411); $^{31}$ P-NMR (DMSO-d$_6$): δ; 4.00 and 3.67.
Anal. Calcd. for $C_{25}H_{32}N_7O_5P \cdot C_4H_4O_4 \cdot 1/2H_2O$: C, 52.25; H, 5.59; N, 14.71. Found: C, 52.25; H, 5.51; N, 14.49.

EXAMPLE 4

(1S,4R)-4-(2-Amino-6-cyclopropylamino-9(H)-purin-9-yl)-2-cyclopenten-1-methanol O-(phenyl ethoxy-L-alaninyl) phosphate Glutarate Salt (S,4R)-4-(2-amino-6-cyclopropylamino-9(H)-purin-9-yl)-2-cyclopentene-1-methanol O-(phenyl ethoxy-L-alaninyl)phosphate (part 1b, 200 mg, 0.38 mmol) was dissolved in ethanol. To this solution was added glutaric acid (50 mg, 0.38 mmol) and the resulting solution evaporated to dryness. The residue was dissolved in acetonitrile (10 mL) with heating. The mixture was stored in the refrigerator overnight and solid collected by filtration to give 130 mg (50%) of a 67:33 mixture of the phosphate isomers as a solid; $^1$H-NMR (DMSO-d$_6$): δ7.6 (s, 1H), 7.1–7.4 (m, 6H), 5.9–6.1 (m, 3H), 5.87 (broad s, 21), 5.44 (m, 1H), 3.95–4.2 (m, 4H), 3.8 (m, 1H), 3.1 (m, 2H), 2.65 (m, 1H), 2.25 (t, 4H), 1.7 (m, 3H), 1.23 (m, 3H), 1.15 (t, 3H), 0.5–0.7 (m, 4H); $^{31}$ P-NMR (DMSO-d$_6$): δ; 4.00 and 3.68.
Anal. Calcd. for $C_{25}H_{32}N_7O_5P \ C_5HBO_4$–$1/2H_2O$: C, 52.78; H, 6.05; N, 14.36. Found: C, 52.97; H, 6.07; N, 14.33.

EXAMPLE 5

(1S,4R)-4-(2-Amino-6-cyclopropylamino-9(H)-purin-9-yl)-2-cyclopentene-1-methanol O-(phenyl ethoxy-L-alaninyl) phosphate D-Tartrate Salt (1S,4R)-4-(2-amino-6-cyclopropylamino-9(H)purin-9-yl)-2-cyclopentene-1-methanol O-(phenyl ethoxy-L-alaninyl)phosphate (157 mg, 0.29 mmol) was dissolved in ethanol. To this solution was added D-tartaric acid (44 mg, 0.29 mmol) and the resulting solution evaporated to dryness. The residue was dissolved in acetonitrile (10 mL) with heating. The mixture was stored in the refrigerator overnight and solid collected by filtration to give 112 mg of a 53:47 mixture of the phosphate isomers as a solid; $^1$H-NMR (DMSO-d$_6$): δ7.6 (s, 1H), 7.1–7.4 (m, 6H), 5.8–6.2 (i 5H), 5.44 (m, 1H), 4.3 (s, 2H), 3.95–4.2 (in, 4H), 3.8 (m, 1H), 3.35 (broad s, 2H), 3.1 (m, 2H), 2.65 (m, 1H), 1.7 (m, 1H), 1.23 (m, 3H), 1.15 (t, 3H), 0.5–0.7 (m, 4H); $^{31}$ P-NMR (DMSO-d$_6$): δ; 4.00 and 3.67.

EXAMPLE 6

(1S,4R)-4-(2-amino6-cyclopropylamino-9(H)-purin-9-yl)-2-cyclopentene-1-methanol O-(phenyl methoxy-L-alaninyl) phosphate Diastereomers An approximately 1:1 mixture of diastereomers of (1S,4R)-4-(2-Amino-6-cyclopropylamino-9(H)-purin-9-yl)-2-cyclopentene-1-methanol O-(phenyl methoxy-L-alaninyl) phosphate was prepared using similar methodology as above: $^1$H-NMR (CDCl$_3$): δ7.5 (2 x s, 1H), 7.1–7.4 (m, 5H), 6.1 (m, 1H), 5.9 (m, 2H), 5.5–5.6 (m, 1H), 4.9 (bs, 2H), 4.2 (m, 2H), 4.05 (m, 1H), 3.7 (s, 3H), 3.6–3.8 (m, 1H) 3.17 (m, 1H), 3.0 (m, 1H), 2.8 (m, 1H), 1.7 (m, 1H), 1.4 (2 x d, 3H), 0.9 (m, 2H), 0.6 (m, 2H); $^{31}$ P-NMR (CDCl$_3$): δ3.07, 3.02.
Anal. Calcd. for $C_{24}H_{30}N_7O_5P \times 2/5$ CHCl$_3$: C, 50.94; H, 5.33; N, 17.00. Found: C, 50.83; H, 5.39; N, 16.94.

The phosphate isomers were separated with Supercritical Fluid Chromatography using a Chiralpak AS column, 25% methanol in carbon dioxide as the eluent, flow rate 2 mL/min, temperature 40° C., and pressure 3000psi. The first isomer to elute had a RT of 2.9 min and was 100% enantiopure; evaporation of solvents gave the isomer as a white solid foam: $^1$H-NMR (CDCl$_3$): δ7.50 (s, 1H), 7.3–7.4 (m, 2H), 7.15–7.25 (m, 3H), 6.11 (m, 1H), 5.91 (m, 1H), 5.86 (s, 1H), 5.55 (m, 1H), 4.89 (s, 2H), 4.24 (m, 2H), 4.05 (m, 1H), 3.72 (s, 3H), 3.65 (m, 1H), 3.20 (m, 1H), 3.02 (m, 1H), 2.83 (m, 1H), 1.72 (m, 1H), 1.37 (d, 3H), 0.89 (m, 2H), 0.62 (m, 2; $^{31}$ p-NMR (CDCl$_3$): 3 3.07.
Anal. Calcd. for $C_{24}H_{30}N_7O_5P \times 1/7CHCl_3$: C, 53.25; H, 5.58; N, 18.00. Found: C, 53.27; H, 5.69; N, 17.72.

The second isomer to elute had a RT of 6.7 min and was 100% enantiopure; evaporation of solvents gave the isomer as a white solid foam: $^1$H-NMR (CDCl$_3$): 3 7.52 (s, 1H), 725–7.4 (m, 2H), 7.15–7.22 (m, 3H), 6.11 (m, 1H), 5.94 (m, 1H), 5.85 (s, 1H), 5.55 (m, 1H), 4.88 (s, 2H), 4.22 (m, 2H), 4.04 (m, 1H), 3.75 (s, 3H), 3.7–3.75 (m, 1H), 3.17 (m, 1H), 3.04 (m, 1H), 2.80 (m, 1H), 1.73 (m, 1H), 1.42 (d, 3H), 0.89 (m, 2H), 0.67 (m, 2H); $^{31}$ P-NMR (CDCl$_3$): δ3.0.
Anal. Calcd. for $C_{24}H_{30}N_7O_5P \times 1/5$ CHCl$_3$: C, 52.71; H, 5.52; N, 17.78. Found: C, 52.61; H, 5.67; N, 17.53.

EXAMPLE 7

(1S,4R)-4-(2-Amino-6-cyclopropylamino-9(H)-purin-9-yl)-2-cyclopentene-1-methanol O-(phenyl N-methylamino-L-alaninyl) phosphate Sodium Salt (1S,4R)-4-(2-Amino-6-cyclopropylamino-9(H)-purin-9-yl)-2-cyclopentene-1-methanol O-(phenyl methoxy-L-alaninyl)phosphate (0.060 g, 0.11 mmoles) was suspended in solution of 40% aqueous methylamine (60 ml) and stirred at room temperature for 18 hours. The volatiles were removed by spin evaporation in vacuo and the residue was dissolved in water (50 ml), extracted with dichloromethane (2×50 ml) and purified by anion exchange chromatography on a Sep-Pak® Vac 35cc Accell™ Plus QMA cartridge (Waters Corp., P/N WAT054725) (HCO3-form) with an aqueous ammonium bicarbonate buffer (0–0.5M gradient, 1 L). The appropriate fractions were combined and the volatiles were remove by spin evaporation in vacuo. The residue was twice dissolved in deionized water and spin evaporated in vacuo to give (1S,4R)-4-(2-amino-6-cyclopropylamino-9(H), purin-9-yl)-2-cyclopentene-1-methanol O-(phenyl N-methylamino-L-alaninyl) phosphate as the ammonium salt. This salt was dissolved in deionized water and passed through a Sep-Pak®Vac 20 cc Accell™ Plus CM cartridge (Waters Corp., PIN WAT054675) (Na$^+$ form) using deionized water. The appropriate fractions were combined and lyophilized to give 0.026 g (46% yield) of (1S,4R)-4-(2-amino-6-cyclopropylamino-9(H)-purin-9-yl)2 cyclopentene-1-methanol O-(phenyl N-methylamino-L- alaninyl) phosphate sodium salt 2.2 hydrate as a white solid::
MS (ES) m/e 449 (MH⁻).
Anal. Calcd. for $C_{18}H_{26}N_8NaO_4P \cdot 2.2\ H_2O$: C, 42.22; H, 5.98; N, 21.88. Found: C, 42.36; H, 5.77; N, 21.66.

EXAMPLE 8

(1S,4R)-4-(2-Amino-6-cyclopropylamino-9(M-purin-9-yi)-2-cyclopentene-1-methanol O-(phenyl N-cyclopropylamino-L-alaninyl) phosphate Sodium Salt

(1S,4R)-4-(2-Amino-6-cyclopropylamino-9(H)-purin-9-yl)-2-cyclopentene-1-methanol O-(phenyl N-cyclopropylamino-L-alaninyl) phosphate sodium salt was prepared by a method analogous to that used to prepare (1S,4R)-4-(2-amino-6-cyclopropylamino 9(H)-purin-9-yl)-2-cyclopentene-1-methanol O-(phenyl N-methylamino-L-alaninyl) phosphate sodium salt except that the 40% aqueous methylamine solution was replaced by a solution of cyclopropylamine (5 ml, 72 mmoles) in deionized water (50 ml). Lyophilization of the combined fractions gave 35 mg (58% yield) of (1S,4R)-4-(2-amino-6-cyclopropylamino-9(H)-purin-9-yl)-2-cyclopentene-1-methanol O-(phenyl N-cyclopropylamino-L-alaninyl) phosphate sodium salt 2.5 hydrate as a white solid: MS (ES⁻) m/e 475 (MH⁻).
Anal. Calcd. for $C_{20}H_{28}N_8NaO_4P \cdot 2.5\ H_2O$: C, 44.20; H, 6.12; N, 20.61. Found: C, 44.27; H, 5.81; N, 20.49.

EXAMPLE 9

(1S,4R)-4-(2-Amino-6-cyclopropylamino-9(H)-purin-9-yl) 2-cyclopentene-1-methanol O-(phenyl N,N-dimethylamino-L-alaninyl) phosphate Sodium Salt

(1S,4R)-4 -(2 -Amino-6-cyclopropylamino-9(H)-purin-9-yl)-2cyclopentene-1-methanol O-(phenyl N-dimethylamino-L-alaninyl) phosphate sodium salt was prepared by a method analogous to that used to prepare (1S,⁴R)-4(2-amino-6-cyclopropylamino-9(H)-purin-9-yl)-2-cyclopentene-1-methanol O-(phenyl N-methylamino-L-alaninyl) phosphate sodium salt except that the 40% aqueous methylamine solution was replaced by a 40% aqueous dimethylamine solution (50 ml). Lyophilization of the combined fractions gave 39 mg (59% yield) of (1S,4R)-4-(2-amino-6-cyclopropylamino-9(H)-purin-9-yl)-2-cyclopentene-1-methanol O-(phenyl N,N-dimethylamino-L-alaninyl) phosphate sodium salt trihydrate as a white solid: MS (ES⁻) m/e 463 M).
Anal. Calcd. for $C_{19}H_{28}N_8NaO_4P \cdot 3.0\ H_2O$: C, 42.22; H, 6.34; N, 20.73. Found: C, 42.40; H, 6.01; N, 20.51

EXAMPLE 10

(1S,4R)-4-(2-Amino-6-cyclopropylamino-9(-purin-9-yl)-2-cyclopentene-1-methanol O-(L-alaninyl) phosphate Disodium Salt

(1S,4R)-4-(2-Amino-6-cyclopropylamino-9H)-purin9-yl)-2-cyclopentene-1-methanol O-(phenyl methoxy-L-alaninyl)phosphate (0.5 g, 0.95 mmoles) was suspended in solution of triethylamine (30 ml) and deionized water (30 ml) and stirred at room temperature for 18 hours. The volatiles Were removed by spin evaporation in vacuo and the residue was dissolved in water (50 ml), extracted with dichloromethane (2×50 ml) and purified by anion exchange chromatography on a Sep-Pak® Vac 35 cc Accell™ Plus QMA cartridge (Waters Corp., P/N WAT054725) (HCO₃⁻ form) with an aqueous ammonium bicarbonate buffer (0–0.5M gradient, 1 L). The appropriate fractions were combined and the volatiles were remove by spin evaporation in vacuo. The residue was twice dissolved in deionized water and spin evaporated in vacuo to give (1S,4R)-4–2-amino6-cyclopropylamino-9(H)-purin-9-yl)-2cyclopentene-1-methanol O-(L-alaninyl) phosphate as the ammonium salt. This salt was dissolved in deionized water and passed through a Sep-Pak® Vac 20 cc Accell™ Plus CM cartridge (Waters Corp., P/N WAT054675) (Na⁺ form) using deionized water. The appropriate fractions were combined and lyophilized to give 0.430 g (86% yield) of (1S,4R)-4-(2-amino-6-cyclopropylamino-9(H)-purin-9-yl)-2-cyclopentene-1-methanol O-(L-alaninyl) phosphate disodium salt 2.5 hydrate as a white solid: MS (ES⁻) m/e 436 M⁻)
Anal. Calcd. for $C_{17}H_{22}N_7Na_2O_5P$ 2.5 $H_2O$: C, 38.79; H, 5.17; N, 18.63. Found: C, 38.62; H, 5.11; N, 18.43.

Anti-Hepatitis B Virus Activity

Compounds of Example 1 to 10 were tested for anti-Hepatitis B Virus activity according to the method described by Jansen, R. et al., *Antimicrobial Agents and Chemotherapy*, Vol.37, No. 3, pp.441–447, 1993. Representative IC₅₀ values were in the range of 0.017 μM-3.0 μM.

The solubility and solution/solid state stability of three salt forms of (1S, 4R)-4-[2-amino-5(cyclopropylamino)-9(H)-purin-9-yl]-2-cyclopentene-1-methanol O-(phenyl ethoxy-L-alaninyl) phosphate The salts have handling and formulation advantages in that they are stable, free-flowing crystalline solids that do not change composition, even at elevated temperature and humidity. The free base of (1S, 4R)-4-[2-amino-6-(cyclopropylamino)-9(H)-purin-9-yl]-2-cyclopentene-1-methanol O-(phenyl ethoxy-L-alaninyl) phosphate in contrast, is a hygroscopic, amorphous solid foam that could not be crystallized.

| Form | Solid Type* | 0.1 N HCl | | PBS | | HPMC/Tween | | Solid State |
|---|---|---|---|---|---|---|---|---|
| | | Solubility (mg/mL) | Stability (%) | Solubility (mg/mL) | Stability (%) | Solubility (mg/mL) | Stability (%) | Stability (%) |
| Free Base | Amorphous Hygroscopic | >5 | 69.1 | 0.054 | 98.5 | 0.04 | 97.6 | 93.7 |
| Glutarate | crystals | >5 | 69.3 | 0.084 | 99.9 | >0.25, <1 | 98.6 | 98.9 |
| Fumarate | crystals | >5 | 70.0 | 0.086 | 98.5 | 0.22 | 98.3 | 97.1 |
| Succinate | crystals | >5 | 66.0 | 0.069 | 99.8 | >0.25, <1 | 98.8 | 99.6 |

Solution stability = % of parent (AUC) after 27 hr at room temperature, normalized to initial AUC.
Solid state stability = % of parent (AUC) after two weeks at 60° C., normalized to initial AUC.

The free bases of the phosphoramidates of 2', 3'-dideoxy adenosine and 2',3'-dideoxy-2', 3'-didehydroadenosine are hygroscopic amorphous foams or gums. However, their instability to acid prevents advantageous utilization of complexes with acids to form salts with improved physical properties; exposure to acids degrades these compounds rapidly. (1S, 4R)-4-[2-amino-6-(cyclopropylamino)-9H-purin-9-yl]-2-cyclopentene-1-methanol (abacavir) has enhanced stability to acid, compared to nucleosides containing labile glycosidic bonds between heterocycle and sugar. Thus phosphoramidate protides of abacavir form stable salts that have been found to have advantageous physical properties suitable for pharmaceutical development.

What is claimed is:

1. A compound of the formula:

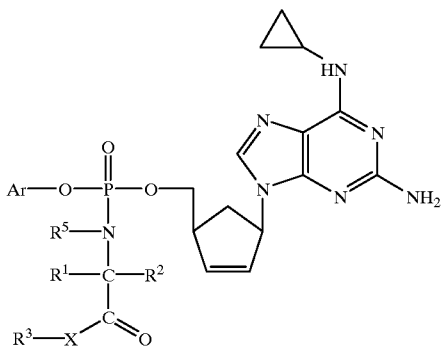

wherein
Ar is an aryl group
each of $R^1$ and $R^2$ independently of the other is hydrogen, alkyl, alkyl substituted with phenyl, or aryl,
X is O, NH, $NR^4$ or S wherein $R^4$ is alkyl or aryl;
$R^5$ when taken independently of $R^1$ is hydrogen, alkyl or aryl, or $R^5$ and $R^1$ taken together are alkylene of 3 or 4 carbon atoms so as to form a 5- or 6-membered ring;
and $R^3$ is
  (i) hydrogen,
  (ii) alkyl,
  (iii) alkyl substituted with phenyl,
  (iv) aryl,
  (v) an unsubstituted or substituted heterocyclic group comprising (i) a saturated or unsaturated heterocyclic ring having up to 12 atoms, one or two of which atoms independently is O, S, or N, said ring being optionally bridged, or (ii) said ring fused to a benzo group or to another heterocyclic ring as herein defined; or
  (vi) an unsubstituted or substituted polycyclic group comprising (i) at least one saturated or unsaturated nonaromatic carbocyclic ring of up to 12 atoms and (ii) a second fused or unfused ring which is (a) a saturated or unsaturated nonaromatic carbocyclic ring as herein defined or (b) a heterocyclic group as herein defined,
or a pharmaceutically acceptable salt, ester, or salt of said ester of said compound, which salt, ester, or salt of said ester is operable to provide in vivo either said compound or an antiviral metabolite thereof.

2. A compound according to claim 1 wherein Ar is phenyl or phenyl substituted with from 1 to 3 substituents selected from the group consisting of halo, halomethyl, oxo, hydroxy, carboxy, carboxyalkyl, alkoxy, alkoyl, alkoyloxy, aryloxy, aryloyl, aryloyloxy, amino, alkylamino, dialkylamino, cyano, azide, nitro, thiol, alkylthiol, sulphonyl, sulphoxide, optionally substituted heterocyclic, optionally substituted alkyl, and optionally substituted aryl.

3. A compound according to claim 1 wherein $R^3$ is selected from the group comprising —$CH_3$, —$C_2H_5$ and —$CH_2Ph$.

4. A compound of the formula:

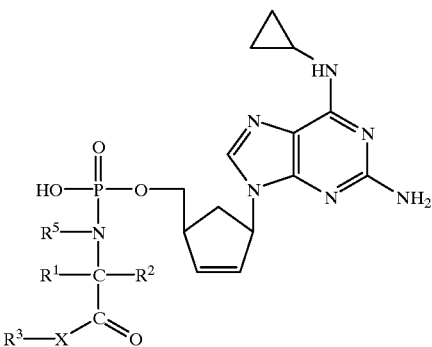

wherein $R^1$ and $R^2$ are each independently selected from the group consisting of hydrogen alkyl, alkyl substituted with phenyl, and aryl,
X is selected from the group consisting of O, NH, $NR^4$ and S wherein $R^4$ is selected from the group comprising alkyl and aryl;
$R^5$ when taken independently of $R^1$ is selected from the group consisting of hydrogen, alkyl and aryl, or $R^5$ and $R^1$ taken together are alkylene of 3 or 4 carbon atoms so as to form a 5- or 6-membered ring;
and $R^3$ is selected from the group consisting of
hydrogen,
alkyl,
alkyl substituted with phenyl,
aryl,
an unsubstituted or substituted heterocyclic group comprising (i) a saturated or unsaturated ring having up to 12 atoms, one or two of which atoms consists of heteroatoms independently selected from the group consisting of O, S, and N, said ring being optionally bridged, or (ii) said ring fused to a benzo group or to another heterocyclic ring as herein defined; and an unsubstituted or substituted polycyclic group comprising (i) at least one saturated or unsaturated nonaromatic carbocyclic ring of up to 12 atoms and (ii) a second fused or unfused ring selected from the group consisting of (a) a saturated or unsaturated nonaromatic carbocyclic ring as herein defined and (b) a heterocyclic group as herein defined,
or a pharmaceutically acceptable salt, ester, or salt of said ester thereof operable to provide said compound in vivo.

5. A compound according to claim 4 wherein $R^1$ and $R^2$ are the same or different and are H, —$CH_3$ or —$CH_2CH_3$.

6. A compound according to claim 4 wherein $R^1$ is H and $R^2$ is —$CH_3$ or —$CH_2$—Ph.

7. A compound according to claim 6 wherein the C atom bearing $R^1$ and $R^2$ is chiral.

8. A compound according to claim 6 wherein the compound has L chirality with respect to the C atom bearing $R^1$ and $R^2$.

9. A compound according to any one of claims 1 to 8 wherein X is O.

10. A compound selected from:
(1S,4R)-4-[2-amino-6cyclopropylamino)-9H-purin-9-yl]-2-cyclopentene-1-methanol O-[phenyl methoxy-L-alaninyl] phosphate
(1S14R)-4-[2-amino-6-(cyclopropylamino)-9H-purin-9-yl]-2-cyclopentene-1-methanol O-[L-alannyl] phosphate diammonium salt (1S,4R)-4-[2-amino-6-(cyclopropylamino)-9H-purin-9-yl]-2-cyclopentene-1-methanol O-[phenyl benzyloxy-L-alaiinyl]phosphate (1S,4R)-4-[2-anino-⁶-(cyclopropylamino)-9H-purin-9-yl]-2-cyclopentene-1-methanol O-[phenyl methoxy-D-alaninyl]phosphate (1S,4R)-4 2-amino-6-(cyclopropylamino)-9H-purin-9-yl]-2-cyclopentene-1-methanol O-[phenyl methoxy-α,α-dimethylglycinyl]phosphate (1S,4R)-4-[2-amino-6(cyclopropylamino)-9H-purin-9-yl]-2-cyclopentene-1-methanol O-[phenyl methoxy-L-phenylalaninyl]phosphate (1S,4R)-4-[2-amino-6-(cyclopropylamino)-9H-purin-9-yl]-2-cyclopentene 1-methanol O-[phenyl ethoxy-L-alaninyl]phosphate (1S,4R)-4-[2-amino-6-(cyclopropylamino)-9H-purin-9-yl]-2-cyclopentene-1-methanol O-[phenyl methoxyglycinyl]phosphate (1S,4R)-4-[2-amino-6-(cyclopropylamino)-9H-purin-9-yl]-2-cyclopentene-1-metanol-O-[phenyl L-aspartyl dimethyl ester]phosphate, (1S,4R)-4-[2-amino-6-(cyclopropylamino)-9H-purin-9-yl]-2-cyclopentene-1-methanol O-[4-chlorophenyl methoxy-L-alaninyl]phosphate (1S,4R)-4-[2-amino-6-(cyclopropylamino)-9H-purin-9-y]-2-cyclopentene-1-methanol O-[phenyl tertbutyloxy-L-alaninyl]phosphate (1S,4R)-4-[2-amino-6-(cyclopropyamino)-9H-purin-9-yl]-2-cyclopentene-S-metanol-O-[phenyl n-propoxy-L-alaninyl]phosphate (1S,4R)-4-[2-amino-6-(cyclopropylamino)-9H-purin-9-yl]-2-cyclopentene-1-methanol O-[Phenyl n-butyloxy-L-alaninyl]phosphate (1S,4R)-4-[2-amino-6-(cyclopropylamino)-9H-purin-9-yl]-2-cyclopentene-1-methanol O-[Phenyl 1-propoxy-L-alaninyl]phosphate (1S,4R)-4-[2-amino-6-(cyclopropylamino)-9H-purin-9-yl]-2cyclopentene-1-methanol O-[(p-(2",2"-dimethoxypropionic acid methyl ester) phenyl) methoxy-L-alaninyl]phosphate (1S,4R)-4-[2-amino-6-(cyclopropylamino)-9H-purin-9-yl]-2-cyclopentene-1-methanol O-[phenyl (2-methylpropyl)oxy-L-alaninyl]phosphate (1S,4R)-4-[2-amino-6-(cyclopropylamino)-9H-purin-9-yl]-2-cyclopentene 1-methanol O-[phenyl (2,2-dimethylpropyl)oxy-L-alaninyl]phosphate (1S,4R)-4-amino-6-(cyclopropylamino)-9H-purin-9-yl] 2-cyclopentene-1-methanol O-[phenyl 3-methylbutyloxy-L-alaninyl]phosphate (1S,4R)-4-[2-amino-6-(cyclopropylamino)-9H-purin-9-yl]-2-cyclopentene-1-methanol O-[phenyl 3-pentyloxy-L-alaninyl]phosphate (1S,4R)-4–2-amino-6-(cyclopropylamino)-9H-purin-9-yl],-2-cyclopentene-1-methanol O-[phenyl methoxy-L-valinyl]phosphate (1S,4R)-4–12-amino-6-(cyclopropylamino)-9H-purin-9-yl]-2-cyclopentene-1-methanol O-[phenyl 3,3-dimethyl-1-butyloxy-L-alaninyl]phosphate (1S,4R)-4-[2-amino-6-(cyclopropylamino)-9H-purin-9-yl]-2-cyclopentene-1-methanol O-[Phenyl n-pentyloxy-L-alaninyl]phosphate (1S,4R)-4-[2-amino-6(cyclopropylamino)-9H-purin-9-yl]-2-cyclopentene-1-methanol O-[Phenyl cyclohexyloxy-L-alaninyl]phosphate (1S,4R)-4-[2-amino-6-(cyclopropylamino)-9H-purin-9-yl]-2-cyclopentene-1-methanol O-[Phenyl cyclohexanemethoxy-L-alaninyl]phosphate (1S,4R)-4-[2-amino-6-(cyclopropylamino)-9H-purin-9-yl]-2-cyclopentene-1-methanol O-[Phenyl methoxy-3-cyclohexane-L-alaninyl]phosphate (1S,4R)-4-[2-amino-6-(cyclopropylamino)-9H-purin-9-yl]-2-cyclopentene-1-methanol O-[4-bromophenyl methoxy-L-alaninyl]phosphate (1S,4R)-4-[2-amino-6-(cyclopropylamino)-9H-purin-9-yl]-2-cyclopentene-1-methanol O-[phenyl diethoxy-L-aspartyl]phosphate (1S,4R)-4-[2-amino-6-(cyclopropylamino)-9H-purin-9-yl]-2-cyclopentene-1-methanol O-[phenyl methoxy-L-methionyl]phosphate (1S,4R)-4-[2-amino6-(cyclopropylamino)-9H-purin-9-yl]-2-cyclopentene-1-methanol O-[phenyl methoxy-L-leucinyl]phosphate (1s,4R)-4-[2-amino-6-(cyclopropylamino)-9H-purin-9-yl]-2-cyclopentene-1-methanol O-[phenyl methoxy-L-prolinyl]phosphate.

(1S,4R)-4-[2-amino-6(cyclopropylamino)-9H-purin-9-yl]-2-cyclopentene-1-methylene-[phenyl dibenzyloxy-L-aspartinyl]phosphate (1S,4R)-4-[2-amino-6-(cyclopropylamino)-9H-purin-9-yl]-2-cyclopentene-1-methanol O-[phenyl 4-methyl-1-pentyloxy-L-alaninyl]phosphate (1S,4R)-4-[2-amino-(cyclopropylamino)-9H-purin-9-yl-2-cyclopentene-1-methanol O-[phenyl cyclopentylmethoxy-L-alaninyl]phosphate (1S,4R)-4-[2-amino-6-(cyclopropylamino)-9H-purin-9-yl]-2-cyclopentene-1-methanol O-[4-fluorophenyl methoxy-L-alaninyl]phosphate (1S,4R)-4-[2-amino-6-(cyclopropylamino)-9H-purin-9-yl]-2-cyclopentene-1-methanol O-[4-iodophenyl methoxy-L-alaninyl]phosphate (1S,4R)-4-[2-amino-6-(cyclopropylamino)-9H-purin-9-yl]-2-cyclopentene-1-methanol O-[phenyl dimethoxy-L-glutamyl]phosphate (1s,4R)-4-[2-amino6-(cyclopropylamino)-9H-purin-9-yl)-2-cyclopentene-1-methanol O-(phenyl methoxy-L-tryptophanyl]phosphate (1S,4R) 4-[2-amino-6-(cyclopropylamino)-9H-purin-9-yl]--cyclopentene-1-methanol O-(phenyl methoxy-L-isoleucinyl]phosphate (1S (1S,4R)-4-[2-amino6-(cyclopropylamino)-9H-purin-9-yl]-2-cyclopentene-1-methanol O-[phenyl cycloheptanyloxy-L-alaninyl]phosphate (1S,4R)-4-[2-amino-6-(cyclopropylamino)-9H-purin-9-yl]-2-cyclopentene-1-methanol O-[phenyl cyclobutylmethoxy-L-alaninyl]phosphate (1S,4R)-4-[2-amino-6-(cyclopropylamino)-9H-purin-9-yl]-2-cyclopentene-1-methanol O-[phenyl cyclopropylmethoxy-L-alaninyl]phosphate (1S,4R)$[-amino-6cyclopropylamino)-9H-purin-9-yl]-2 cyclopentene-1-methanol O-[phenyl cyclobutyloxy-L-alaninyl]phosphate (1S,4R)-4-[2-amino-6-(cyclopropylamino)-9H-purin-9-yl]-2-cyclopentene-1-methanol O-[phenyl cyclopentyloxy-L-alaninyl]phosphate (1S,4R)-4-[2-amino-6-(cyclopropylamino)-9H-purin-9-yl]-2-cyclopentene-i-methanol O-[phenyl phenethoxy-L-alaninyl]phosphate (1S,4R)-4-[2-amino-6-(cyclopropylamino)-9H-purin-9-yl]-2-cyclopentene-1-methanol O-[phenyl 3-phenyl-1-propoxy-L-alaninyl]phosphate (1S,4R)-4-m2-amino-6-(cyclopropylamino)-9H-purin-9-yl]-2 cyclopentene-1-methanol O-[phenyl 4-phenyl-1-butoxy-L-alaninyl]phosphate (1S4R)-4-[2-amino-6-(cyclopropylamino)-9H-purin-9-yl]-2-cyclopentene-1-methanol O-[phenyl 2-cyclohexyl-1-ethoxy-L-alaninyl]phosphate (1S,4R)-4-[2-amino-6-(cyclopropylamino)-9H-purin-9-yl]-2-cyclopentene-1-methanol O-[phenyl 3-cyclohexyl-1-propoxy-L-alaninyl]phosphate (1S,4R)-4-[2-amino-6-(cyclopropylamino)-9H-purin-9yl]-2-cyclopentene-1-methanol O-[phenyl 4cyclohexyl-1-butoxy-L-alaninyl]phosphate (1S,4R)-4-[2-amino-6-(cyclopropylamino)-9H-purin-9-yl]-2-cyclopentene-1-methanol O-[phenyl methoxy-α-ethyl-L-glycinyl]phosphate (1S,4R)-4-[2-amino-6-cyclopropylamino)-9H-purin-9-yl]-2-cyclopentene-1-methanol O[phenyl methoxy-α-phenyl(RS)glycinyl]phosphate (1S,4R)-4-[2-amino-6-(cyclopropylamino)-9H-purin-9yl]-2-cyclopentene-1-methanol O-[phenyl methoxy-α-propyl-L-glycinyl]phosphate)

(1S,4R)-4–12-amino6-(cyclopropylamino)-9H-purin-9-yl]-2-cyclopentene-1-methanol O-([phenyl methoxy-α-butyl-L-glycinyl]phosphate (1S,4R)-4-[2-amino-6-(cyclopropylamino)-9H-purin-9-yl]-2-cyclopentene-1-methanol O-[p-phenoxyphenyl methoxy-L-alaninyl]phosphate (1S,4R)-4-[2-amino-6-(cyclopropylamino)-9H-purin-9-yl]-2-cyclopentene-1-methanol O-[p-phenylphenyl methoxy-L-alaninyl)]phosphate (1S,4R)-4-[2-amino-6-(cyclopropylamino)-9H-purin-9-yl]-2-cyclopentene-1-methanol O-[4-hydroxyacetophenone methoxy-L-alaninyl]phosphate (1S,4R)-4-[2-amino-6-(cyclopropylamino)-9H-purin-9-yl]-2-cyclopentene-1-methanol O-[4-butylphenyl methoxy-L-alaninyl]phosphate (1S,4R)-4-[2-amino-6-(cyclopropylamino)-9H-purin-9-yl]-2-cyclopentene-1-methanol O-[p-methoxyphenyl methoxy-L-alaniyl]phosphate (1S,4R)-4-[2-amino-6-(cyclopropylamino)-9H-purin-9-yl]-2cyclopentene-1-methanol O-[p-propoxyphenyl methoxy-L-alaninyl]phosphate (1S,4R)-4-[2-amino-6(cyclopropylamino)-9H-purin-9-yl]-2-cyclopentene-1-methanol O-[phenyl methoxy-α,α-cyclopentylglycinyl]phosphate (1S,4R)-4-[2amino-6-(cyclopropylamino)-9H-purin-9-yl]-2Cyclopentene-1-methanol O-[phenyl methoxy-α,α-cylohexylglycinyl]phosphate (1S,4R)-[4-[2-amino-6-(cyclopropylamino)-9H-purin-9-yl]-2-cyclopentene-1-methanol O-[phenyl methoxy-α,α-cyclopropylglycinyl)]phosphate (1S,4R)-4-[2-amino-6-(cyclopropylamino)-9H-purin-9-yl]-2-cyclopentene-1-methanol O-[phenyl (methoxycarbonyl)phenyl methoxy-L-alaninyl]phosphate (1S,4R)-4-[2-amino-6-(cyclopropylamino)-9H-purin-9-yl]-2-cyclopentene-1-methanol O-[p-(trifluoromethylthio)phenyl methoxy-L-alaninyl]phosphate (1S,4R)-4-[2-amino-&(cyclopropylamino)-9H-purin-9-yl]-2-cyclopentene-1-methanol O-[p-(2-methoxyvinyl)phenyl methoxy-L-alaninyl]phosphate (1S,4R)-4-[2-amino-6-(cyclopropylamino)-9H-purin-9-yl]-2-cyclopentene-1-methanol O-[p-(2-phenylcarbonylvinyl)phenyl methoxy-L-alaninyl]phosphate (1S,4R)-4-[2-amino-64cyclopropylamino)-9H-purin-9-yl]-2-cyclopentene-1-methanol O-[p-(2,2-dicyanovinyl)phenyl methoxy-L-alaninyl]phosphate (1S,4R)-4-[2-amino-6-(cyclopropylamino)-9H-purin-9-yl]-2-cyclopentene-1-methanol O-[o-(carboxylate ethyl ester)phenyl methoxy-L-alaninyl]phosphate (1S,4R)-4-(2-amino-6-(cyclopropylamino-9(H)-purin-9-yl)-2-cyclopentene-1-methanol O-(phenyl ethoxy-L-alaninyl) phosphate succinate salt (1S,4R)-4-(2-amino6-cyclopropylamino-9(H)-purin-9yl)-2-cyclopentene-1-methanol O-(phenyl methoxy-L-alaninyl) phosphate succinate salt (1S,4R)-4-(2-amino-6-cyclopropylamino-9(H)-purin-9-yl)-2-cyclopentene-1-methanol O-(phenyl ethoxy-L-alaniyl) phosphate fumarate salt (1S,4R)-4(2-amino-6-cyclopropylamino-9(H)-purin-9-yl)-2-cyclopentene-1-methanol O-(phenyl ethoxy-L-alaninyl) phophate glutarate salt (1S,4R)-4-(2-amino-6-cyclopropylamino-9(H)-purin-9-yl)-2-cyclopentene-1-methanol O-(phenyl ethoxy-L-alaninyl) phosphate D-tartrate salt (1S,4R)-4-(2-amino-6-cyclopropylamino-9(H)-purin-9-yl)-2-cyclopentene-1-methanol O-(phenyl methoxy-L-alaninyl) phophate diastereoisomers (1S,4R)-4-(2-amino6-cyclopropylamino-9(H)-purin-9-y1)-2-cyclopentene-1-methanol O-(phenyl N-methylamino-L-alaninyl) phosphate sodium salt (1S,4R)-4-(2-amino-6-cyclopropylamino-9(H)-purin-9-yl)-2-cyclopentene-1-methanol O-(phenyl N-cyclopropylamino-L-alaninyl) phosphate sodium salt (1S,4R)-4(2-amino-6-cyclopropylamino-9(H)-purin-9-yl)-2-cyclopentene-1-methanol O-(phenyl N,N-dimethylamino-L-alaninyl) phosphate sodium salt (1S,4R)-4-(2-amino-6-cyclopropylamino-9(H)-purin-9-yl)-2-cyclopentene-1-methanol O-(L-alaninyl) phosphate disodium salt.

11. A pharmaceutical composition comprising a compound according to claim 4 in combination with a pharmaceutically acceptable excipient.

12. A composition according to claim 11 in a form for oral administration.

13. A process for the preparation of a compound according to claim 1 comprising allowing a compound having the formula:

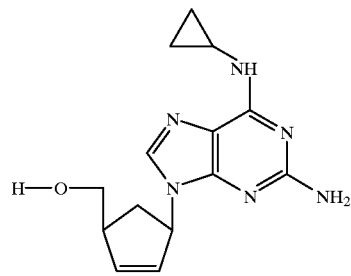

to react with a compound of formula:

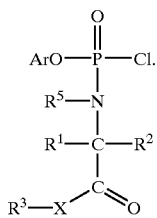

14. A pharmaceutical composition comprising a compound according to claim 1 in combination with a pharmaceutically acceptable excipient.

15. A method of prophylaxis or treatment of an HIV or HBV viral infection comprising administration to a patient in need of such treatment an effective dose of a compound according to claim 1.

16. A method of prophylaxis or treatment of an HIV or HBV viral infection comprising administration to a patient in need of such treatment an effective dose of a compound according to claim 4.

17. A method according to claim 15 comprising administering orally to a patient an effective dose of the compound.

18. A method according to claim 16 comprising administering orally to a patient an effective dose of the compound.

19. A composition according to claim 14 in a form for oral administration.

* * * * *